(12) United States Patent
Panescu et al.

(10) Patent No.: US 10,350,009 B2
(45) Date of Patent: Jul. 16, 2019

(54) QUANTITATIVE THREE-DIMENSIONAL IMAGING AND PRINTING OF SURGICAL IMPLANTS

(71) Applicant: Intuitive Surgical Operations, Inc., Sunnyvale, CA (US)

(72) Inventors: Dorin Panescu, San Jose, CA (US); Daniel H Jones, Alexandria, VA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 109 days.

(21) Appl. No.: 15/300,262

(22) PCT Filed: Mar. 28, 2015

(86) PCT No.: PCT/US2015/023213
§ 371 (c)(1),
(2) Date: Sep. 28, 2016

(87) PCT Pub. No.: WO2015/149043
PCT Pub. Date: Oct. 1, 2015

(65) Prior Publication Data
US 2017/0181798 A1    Jun. 29, 2017

Related U.S. Application Data

(60) Provisional application No. 62/096,518, filed on Dec. 23, 2014, provisional application No. 61/971,749, filed on Mar. 28, 2014.

(51) Int. Cl.
*A61B 34/10* (2016.01)
*A61B 34/32* (2016.01)
(Continued)

(52) U.S. Cl.
CPC .......... *A61B 34/10* (2016.02); *A61B 1/00009* (2013.01); *A61B 1/04* (2013.01);
(Continued)

(58) Field of Classification Search
None
See application file for complete search history.

(56) References Cited

U.S. PATENT DOCUMENTS 5,704,897 A   1/1998   Truppe
5,749,362 A   5/1998   Funda et al.
(Continued)

FOREIGN PATENT DOCUMENTS

CA   2859998 A1   5/2013
CN   1874734 A    12/2006
(Continued)

OTHER PUBLICATIONS

Extended European Search Report for Application No. EP15769289.8, dated Dec. 12, 2017, 11 pages.
(Continued)

*Primary Examiner* — Eileen M Adams
(74) *Attorney, Agent, or Firm* — Schwegman Lundberg & Woessner, P.A.

(57) ABSTRACT

A system to produce a replacement anatomical structure, comprising: a quantitative three-dimensional (Q3D) endoscope disposed to image a structure within a field of view that includes target tissue; at least one processor configured to: produce a first Q3D model of an anatomical structure that includes target tissue; produce a second Q3D model of the anatomical structure that includes remainder tissue in a location from which the target has been tissue removed; and produce a third Q3D model of a replacement structure based at least in part upon the first Q3D model and the second Q3D model.

19 Claims, 38 Drawing Sheets

(51) Int. Cl.

| | |
|---|---|
| *A61B 34/30* | (2016.01) |
| *A61B 34/37* | (2016.01) |
| *H04N 13/254* | (2018.01) |
| *A61B 1/00* | (2006.01) |
| *A61B 1/04* | (2006.01) |
| *A61B 1/06* | (2006.01) |
| *A61B 5/00* | (2006.01) |
| *G02B 23/24* | (2006.01) |
| *G06T 17/00* | (2006.01) |
| *H04N 13/232* | (2018.01) |
| *A61B 34/20* | (2016.01) |
| *H04N 13/30* | (2018.01) |

(52) U.S. Cl.
CPC .............. *A61B 1/06* (2013.01); *A61B 5/4851* (2013.01); *A61B 34/30* (2016.02); *A61B 34/32* (2016.02); *A61B 34/37* (2016.02); *G02B 23/2415* (2013.01); *G02B 23/2484* (2013.01); *G06T 17/00* (2013.01); *H04N 13/232* (2018.05); *H04N 13/254* (2018.05); *A61B 34/20* (2016.02); *A61B 2034/105* (2016.02); *A61B 2034/2059* (2016.02); *H04N 13/30* (2018.05)

(56) References Cited

U.S. PATENT DOCUMENTS

| | | |
|---|---|---|
| 5,833,633 A | 11/1998 | Sarvazyan et al. |
| 6,346,940 B1 | 2/2002 | Fukunaga |
| 6,491,702 B2 | 12/2002 | Heilbrun et al. |
| 6,503,195 B1 | 1/2003 | Keller et al. |
| 6,522,906 B1 | 2/2003 | Salisbury, Jr. et al. |
| 6,650,927 B1 | 11/2003 | Keidar |
| 6,932,610 B2 | 8/2005 | Ono et al. |
| 6,950,550 B1 | 9/2005 | Sumi et al. |
| 7,728,868 B2 | 6/2010 | Razzaque et al. |
| 7,907,166 B2 | 3/2011 | Lamprecht et al. |
| 8,231,522 B2 | 7/2012 | Endo et al. |
| 8,262,559 B2 | 9/2012 | Krattiger |
| 8,334,900 B2 | 12/2012 | Qu et al. |
| 8,514,491 B2 | 8/2013 | Duparre |
| 8,861,089 B2 | 10/2014 | Duparre |
| 8,866,920 B2 | 10/2014 | Venkataraman et al. |
| 8,902,321 B2 | 12/2014 | Venkataraman et al. |
| 9,041,829 B2 | 5/2015 | Venkataraman et al. |
| 9,060,142 B2 | 6/2015 | Venkataraman et al. |
| 9,119,552 B2 | 9/2015 | Baumann et al. |
| 9,188,765 B2 | 11/2015 | Venkataraman et al. |
| 9,235,898 B2 | 1/2016 | Venkataraman et al. |
| 9,264,610 B2 | 2/2016 | Duparre |
| 9,485,496 B2 | 11/2016 | Venkataraman et al. |
| 10,052,157 B2 | 8/2018 | Frimer et al. |
| 2001/0051761 A1 | 12/2001 | Khadem |
| 2002/0022765 A1 | 2/2002 | Belson |
| 2002/0049375 A1 | 4/2002 | Strommer et al. |
| 2003/0036714 A1 | 2/2003 | Kuth et al. |
| 2003/0158477 A1 | 8/2003 | Panescu |
| 2003/0181800 A1 | 9/2003 | Bonutti |
| 2003/0220541 A1 | 11/2003 | Salisbury et al. |
| 2005/0151839 A1 | 7/2005 | Ito et al. |
| 2005/0182295 A1 | 8/2005 | Soper et al. |
| 2005/0219205 A1 | 10/2005 | Bailey et al. |
| 2005/0254720 A1 | 11/2005 | Tan |
| 2006/0183992 A1 | 8/2006 | Kawashima et al. |
| 2006/0281971 A1 | 12/2006 | Sauer et al. |
| 2007/0055128 A1 | 3/2007 | Glossop et al. |
| 2007/0060792 A1 | 3/2007 | Draxinger et al. |
| 2007/0083098 A1 | 4/2007 | Stern et al. |
| 2007/0135803 A1 | 6/2007 | Belson |
| 2007/0147707 A1 | 6/2007 | Coste-Maniere et al. |
| 2007/0151391 A1 | 7/2007 | Larkin et al. |
| 2007/0171369 A1 | 7/2007 | Grundig |
| 2007/0236514 A1 | 10/2007 | Agusanto et al. |
| 2007/0276501 A1 | 11/2007 | Betz et al. |
| 2008/0004603 A1 | 1/2008 | Larkin et al. |
| 2008/0009674 A1 | 1/2008 | Yaron et al. |
| 2008/0058593 A1 | 3/2008 | Gu et al. |
| 2008/0071140 A1 | 3/2008 | Gattani et al. |
| 2008/0188716 A1 | 8/2008 | Heckele et al. |
| 2008/0207997 A1 | 8/2008 | Higgins et al. |
| 2009/0043161 A1 | 2/2009 | Doi |
| 2009/0054910 A1 | 2/2009 | Zheng et al. |
| 2009/0076476 A1 | 3/2009 | Barbagli et al. |
| 2009/0088634 A1 | 4/2009 | Zhao et al. |
| 2009/0088897 A1 | 4/2009 | Zhao et al. |
| 2009/0133260 A1* | 5/2009 | Durbin .............. A61C 13/0004 29/896.11 |
| 2009/0157059 A1 | 6/2009 | Allen et al. |
| 2009/0189749 A1 | 7/2009 | Salada et al. |
| 2009/0192524 A1 | 7/2009 | Itkowitz et al. |
| 2009/0221908 A1 | 9/2009 | Glossop et al. |
| 2009/0259102 A1* | 10/2009 | Koninckx .......... A61B 1/00181 600/111 |
| 2009/0306474 A1 | 12/2009 | Wilson |
| 2009/0317727 A1 | 12/2009 | Beck |
| 2010/0111389 A1 | 5/2010 | Strobel et al. |
| 2010/0149183 A1 | 6/2010 | Loewke et al. |
| 2010/0169815 A1 | 7/2010 | Zhao et al. |
| 2010/0249506 A1 | 9/2010 | Prisco et al. |
| 2010/0281370 A1 | 11/2010 | Rohaly et al. |
| 2010/0312096 A1 | 12/2010 | Guttman et al. |
| 2010/0312129 A1 | 12/2010 | Schecter et al. |
| 2011/0032088 A1 | 2/2011 | Kim et al. |
| 2011/0044521 A1 | 2/2011 | Tewfik et al. |
| 2011/0122229 A1 | 5/2011 | Cinquin et al. |
| 2011/0163946 A1 | 7/2011 | Tartz et al. |
| 2011/0193938 A1 | 8/2011 | Oderwald et al. |
| 2011/0282143 A1* | 11/2011 | Matsumoto .............. A61B 1/05 600/109 |
| 2011/0282151 A1 | 11/2011 | Trovato et al. |
| 2012/0041345 A1 | 2/2012 | Rajamani et al. |
| 2012/0063644 A1 | 3/2012 | Popovic et al. |
| 2012/0101370 A1 | 4/2012 | Razzaque et al. |
| 2012/0139828 A1 | 6/2012 | Lok et al. |
| 2012/0155731 A1 | 6/2012 | Weersink et al. |
| 2012/0182294 A1 | 7/2012 | Cordon et al. |
| 2012/0265062 A1 | 10/2012 | Sliwa et al. |
| 2012/0289777 A1 | 11/2012 | Chopra et al. |
| 2013/0035583 A1 | 2/2013 | Park et al. |
| 2013/0038689 A1 | 2/2013 | McDowall |
| 2013/0079620 A1 | 3/2013 | Kuth et al. |
| 2013/0197357 A1 | 8/2013 | Green et al. |
| 2013/0202676 A1* | 8/2013 | Koob .................. A61L 27/3604 424/443 |
| 2013/0211244 A1 | 8/2013 | Nathaniel et al. |
| 2013/0230837 A1 | 9/2013 | Meglan et al. |
| 2013/0250081 A1 | 9/2013 | Pandey |
| 2013/0296872 A1* | 11/2013 | Davison .............. A61B 17/1739 606/87 |
| 2013/0321262 A1 | 12/2013 | Schecter et al. |
| 2014/0005684 A1 | 1/2014 | Kim et al. |
| 2014/0039527 A1 | 2/2014 | Avelar et al. |
| 2014/0071239 A1 | 3/2014 | Yokota et al. |
| 2014/0163359 A1 | 6/2014 | Sholev et al. |
| 2014/0194896 A1 | 7/2014 | Frimer et al. |
| 2014/0253684 A1 | 9/2014 | Kumar et al. |
| 2014/0276093 A1 | 9/2014 | Zeien et al. |
| 2014/0336501 A1 | 11/2014 | Masumoto |
| 2015/0011894 A1 | 1/2015 | Sarrafzadeh et al. |
| 2015/0025316 A1 | 1/2015 | Hasegawa et al. |
| 2015/0031990 A1 | 1/2015 | Boctor et al. |
| 2015/0049167 A1 | 2/2015 | Suzuki et al. |
| 2015/0062299 A1 | 3/2015 | Brown et al. |
| 2015/0112237 A1 | 4/2015 | Amedi et al. |
| 2015/0134095 A1* | 5/2015 | Hemani .................. G06T 19/00 700/98 |
| 2015/0185849 A1 | 7/2015 | Levesque et al. |
| 2015/0209003 A1 | 7/2015 | Halmann et al. |
| 2015/0230869 A1 | 8/2015 | Shim et al. |
| 2015/0271483 A1 | 9/2015 | Sun et al. |
| 2015/0374210 A1 | 12/2015 | Durr et al. |
| 2016/0151646 A1 | 6/2016 | Bonutti et al. |

(56) References Cited

U.S. PATENT DOCUMENTS

| | | | |
|---|---|---|---|
| 2017/0172662 | A1 | 6/2017 | Panescu et al. |
| 2017/0180704 | A1 | 6/2017 | Panescu et al. |
| 2017/0181808 | A1 | 6/2017 | Panescu et al. |
| 2017/0181809 | A1 | 6/2017 | Panescu et al. |
| 2017/0188011 | A1 | 6/2017 | Panescu et al. |
| 2017/0212723 | A1 | 7/2017 | Atarot et al. |

FOREIGN PATENT DOCUMENTS

| | | | |
|---|---|---|---|
| CN | 101065052 | A | 10/2007 |
| CN | 102046065 | A | 5/2011 |
| CN | 102625670 | A | 8/2012 |
| CN | 102711650 | A | 10/2012 |
| CN | 102781303 | A | 11/2012 |
| CN | 102908158 | A | 2/2013 |
| CN | 103108602 | A | 5/2013 |
| CN | 103269430 | A | 8/2013 |
| CN | 103315696 | A | 9/2013 |
| CN | 103596521 | A | 2/2014 |
| EP | 1826726 | A1 | 8/2007 |
| EP | 2043499 | A1 | 4/2009 |
| EP | 2444006 | A2 | 4/2012 |
| EP | 2548495 | A1 | 1/2013 |
| EP | 2641561 | A1 | 9/2013 |
| JP | H04176429 | A | 6/1992 |
| JP | H04325147 | A | 11/1992 |
| JP | H0630896 | A | 2/1994 |
| JP | H06160087 | A | 6/1994 |
| JP | H07240945 | A | 9/1995 |
| JP | H0998985 | A | 4/1997 |
| JP | H11309 | A | 1/1999 |
| JP | 2000065532 | A | 3/2000 |
| JP | 2002027502 | A | 1/2002 |
| JP | 2002171537 | A | 6/2002 |
| JP | 2003235785 | A | 8/2003 |
| JP | 2005087468 | A | 4/2005 |
| JP | 2005091265 | A | 4/2005 |
| JP | 2006109939 | A | 4/2006 |
| JP | 2006305332 | A | 11/2006 |
| JP | 2009204991 | A | 9/2009 |
| JP | 2010085240 | A | 4/2010 |
| JP | 2011200515 | A | 10/2011 |
| JP | 2012518517 | A | 8/2012 |
| JP | 2013515959 | A | 5/2013 |
| WO | WO-2006080076 | A1 | 8/2006 |
| WO | WO-2007047782 | A2 | 4/2007 |
| WO | WO-2010122145 | A1 | 10/2010 |
| WO | WO-2010147729 | A1 | 12/2010 |
| WO | WO-2012059253 | A1 | 5/2012 |
| WO | WO-2012136223 | A1 | 10/2012 |
| WO | WO-2012155152 | A1 | 11/2012 |
| WO | WO-2013027201 | A2 | 2/2013 |
| WO | WO-2013038403 | A2 | 3/2013 |
| WO | WO-2013134782 | A1 | 9/2013 |
| WO | WO-2014002849 | A1 | 1/2014 |

OTHER PUBLICATIONS

Partial Supplementary European Search Report for Application No. 15767964.8, dated Dec. 13, 2017, 17 pages.
Eltaib, M.E.H., et al., "Tactile Sensing Technology for Minimal Access Surgery—a Review," Mechatronics, Pergamon Press, Oxford, GB, vol. 13(10), Dec. 1, 2003 (Dec. 1, 2003), pp. 1163-1177, XP004448741, DOI: 10.1016/S0957-4158(03)00048-5.
Extended European Search Report for Application No. 15769234.4, dated Oct. 17, 2017, 11 pages.
Garcia O., et al., "Real-time 3D Modeling from Endoscope Image Sequences," ICRA 2009 Workshop—Advanced Sensing and Sensor Integration in Medical Robotics, May 13, 2009 (May 13, 2009), Retrieved from the Internet: URL: http://webdiis.unizar.es/~jcivera/papers/garcia_etal_icra09.pdf [retrieved on Oct. 5, 2017], 3 pages, XP055412801.
Office Action dated Sep. 1, 2017 for Chinese Application No. 201580024436.7 filed Mar. 28, 2015, 25 pages.
Oosten J.V., "Understanding the View Matrix—3D Game Engine Programming 3D Game Engine Programming," Jul. 6, 2011 (Jul. 6, 2011), Retrieved from the Internet: URL: http://www.3dgep.com/understanding-the-view-matrix/ [retrieved on Oct. 14, 2015], 34 pages, XP055220667.
Partial Supplementary European Search Report for Application No. 15770100.4, dated Oct. 18, 2017, 17 pages.
Partial Supplementary European Search Report for Application No. EP15770259.8, dated Oct. 24, 2017, 20 pages.
Rigel, D. S., et al., "The Evolution of Melanoma Diagnosis: 25 Years Beyond the ABCDs," CA Cancer J Clin, vol. 60 (5), Jul. 29, 2010 (Jul. 29, 2010), pp. 301-316, XP055384411, ISSN: 0007-9235, DOI: 10.3322/caac.20074.
Thormahlen T., et al., "Three-Dimensional Endoscopy," Falk Symposium, vol. 124, Jan. 1, 2002, (Jan. 1, 2002), 6 pages, XP055413139, ISBN: 078-0-7923-8774-9.
Wu C., "3D Reconstruction of Anatomical Structures from Endoscopic Images," CMU-R1-TR-10-04, Jan. 1, 2010 (Jan. 1, 2010), Retrieved from the Internet: URL:https://www.cs.cmu.edu/-ILIM/publications/PDFs/W-THESIS09.pdf [retrieved on Oct. 5, 2017], pp. 1-113, XP055412730.
Agus M., et al., "Real-time Cataract Surgery Simulation for Training," In Eurographics Italian Chapter Conference, Eurographics Association, 2006, 5 pages.
Coelho M., et al., "Shape-Changing Interfaces," Personal and Ubiquitous Computing, M. Coelho, et al., MIT Media Lab, 75 Amherst St., E14-548H, Cambridge, MA, USA, Springer-Verlag, published online Jul. 29, 2010, vol. 15 (2), pp. 161-173.
Cotin S., et al., "Real-time Elastic Deformations of Soft Tissues for Surgery Simulation," IEEE Transactions on Visualization and Computer Graphics, 1999, vol. 5, pp. 62-73.
Culijat M., et al., "Pneumatic Balloon Actuators for Tactile Feedback in Robotic Surgery," Industrial Robot: An International Journal, 2008, vol. 35 (5). pp. 449-455.
Delingette H., "Simplex Meshes: A General Representation for 3D Shape Reconstruction," Technical Report 2214, INRIA, Mar. 1994, 59 pages.
Follmer S., et al., "inFORM: Dynamic Physical Affordances and Constraints through Shape and Object Actuation," Proceedings of the 26th Annual ACM Symposium on UIST, ACM, 2013,New York, NY, USA, vol. 13, pp. 417-426.
Hassanfiroozi A., et al., Liquid Crystal Lens Array for 3D Endoscope Application, in: Three-Dimensional Imaging, Visualization, and Display, Javidi B., et al., eds., Proceedings of SPIE, vol. 9117 91170E 1-7, 7 pages, [online], [retrieved Aug. 21, 2014]. Retrieved from the Internet:<URL: http://proceedings.spiedigitallibrary.org/>.
Howe, Robert D. et al., "Remote Palpation Technology," IEEE Engineering in Medicine and Biology, 1995, pp. 318-323, vol. 14—Issue 3, IEEE.
International Search Report and Written Opinion for Application No. PCT/US2015/23212, dated Jun. 30, 2015, 8 pages.
International Search Report and Written Opinion for Application No. PCT/US2015/23213, dated Jul. 14, 2015, 13 pages.
International Search Report and Written Opinion for Application No. PCT/US/5123211, dated Jul. 1, 2015, 13 pages.
International Search Report and Written Opinion for Application No. PCT/US15/23217, dated Jun. 29, 2015, 12 pages.
International Search Report and Written Opinion for Application No. PCT/US2015/023214, dated Jun. 29, 2015, 10 pages.
International Search Report and Written Opinion for Application No. PCT/US15/23210, dated Jun. 29, 2015, 17 pages.
Iwata H., et al., "Project FEELEX: Adding Haptic Surface to Graphics," SIGGRAPH'01, 2001, pp. 469-476.
J. Montagnat and H. Delingette, "Volumetric Medical Images Segmentation Using Shape Constrained Deformable Models," Proceedings of CVRMed-MRCAS '97, Grenoble, France,J. Troccaz, E. Grimson, and R. Mosges, eds. Mar. 1997, pp. 13-22.
K. Chinzei and K. Miller, "Compression of Swine Brain Tissue; Experiment in Vitro," Journal of Mechanical Engineering Laboratory, Jul. 1996, vol. 50(4), pp. 106-115.

(56) References Cited

OTHER PUBLICATIONS

Killebrew J.H., et al., "A Dense Array Stimulator to Generate Arbitrary Spatia-Temporal Tactile Stimuli," Journal of Neuroscience Methods, 2007, vol. 161 (1), pp. 62-74.

Laks Raghupathi, Laurent Grisoni, Fran?ois Faure, Damien Marchal, Marie-Paule Cani, Christophe Chaillou, "An Intestinal Surgery Simulator: Real-Time Collision Processing and Visualization," IEEE Transactions on Visualization and Computer Graphics, vol. 10, No. 6, pp. 708-718, Nov./Dec. 2004.

Monserrat C., et al., "GeRTiSS: A Generic Multi-model Surgery Simulator," Springer-Verlag Berlin Heidelberg, IS4TM 2003, LNCS 2673, 2003, pp. 59-66.

Moore M., et al., "Collision Detection and Response for Computer Animation," Computer Graphics, SIGGRAPH, 1988, vol. 22 (4), pp. 289-298.

Moy G., et al., "A Compliant Tactile Display for Teletaction," Proceedings of ICRA in Robotics and Automation, 2000, IEEE, vol. 4, 7 pages.

Okamura A.M., "Haptic Feedback in Robot-Assisted Minimally Invasive Surgery," Current Opinion in Urology, 2009, vol. 19 (1), pp. 102-107.

Ottermo M.V., et al., "Electromechanical Design of a Miniature Tactile Shape Display for Minimally Invasive Surgery," Proceedings of the First Joint Eurohaptics Conference and Symposium on Haptic Interfaces for Virtual Environment and Teleoperator Systems, IEEE, 2005, 2 pages.

Rasmussen M.K., et al., "Shape-Changing Interfaces: A Review of the Design Space and Open Research Questions," Proceedings of the SIGCHI Conference on Human Factors in Computing Systems on CHI, ACM, 2012, pp. 735-744.

Reiley, Carol E. et al., "Effects of visual force feedback on robot-assisted surgical task performance," Journal of Thoracic and Cardiovascular Surgery, Jan. 2008, vol. 35 (1), pp. 196-202.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP15768409.3, dated Feb. 26, 2018, 9 pages.

Extended European Search Report for Application No. EP15770100.4, dated Feb. 16, 2018, 14 pages.

Extended European Search Report for Application No. EP15770259.8, dated Feb. 21, 2018, 18 pages.

Office Action dated Jul. 4, 2018 for Chinese Application No. 201580024439.0 filed Mar. 28, 2015, 13 pages.

Extended European Search Report for Application No. EP15767964.8, dated Apr. 24, 2018, 19 pages.

U.S. Appl. No. 15/300,255, filed Sep. 28, 2016, Quantitative Three-Dimensional Imaging of Surgical Scenes.

U.S. Appl. No. 15/300,258, filed Sep. 28, 2016, Quantitative Three-Dimensional Visualization of Instruments in a Field of View.

U.S. Appl. No. 15/300,263, filed Sep. 28, 2016, Surgical System with Haptic Feedback Based Upon Quantitative Three-Dimensional Imaging.

U.S. Appl. No. 15/300,265, filed Sep. 28, 2016, Quantitative Three-Dimensional Imaging of Surgical Scenes From Multiport Perspectives.

\* cited by examiner

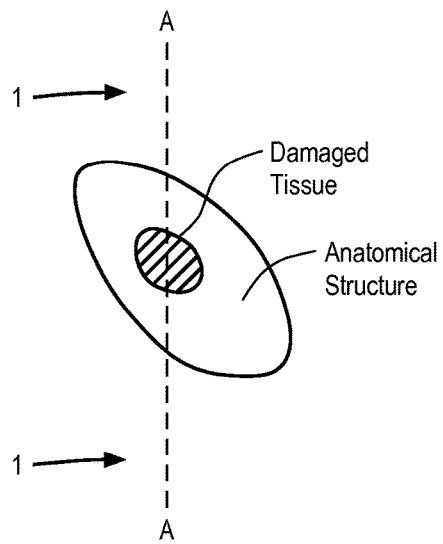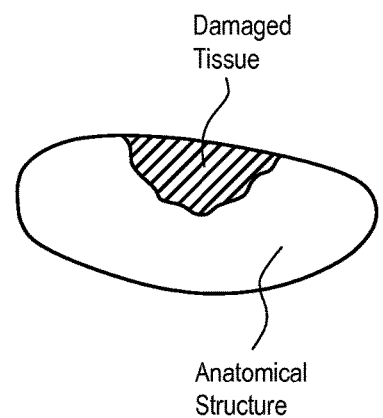
FIG. 25A  FIG. 25B
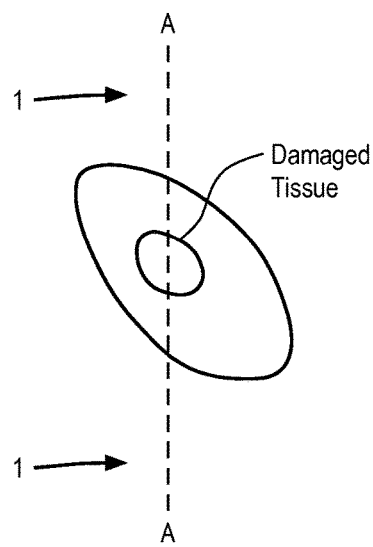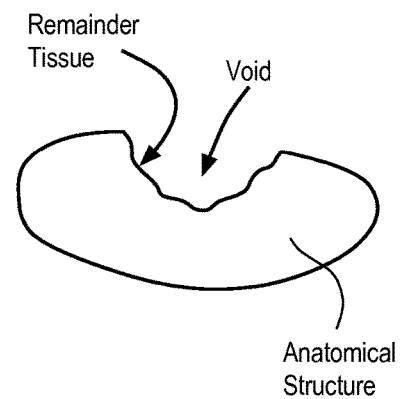
FIG. 26A  FIG. 26B

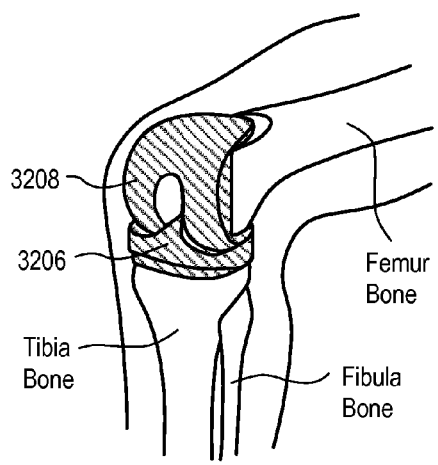
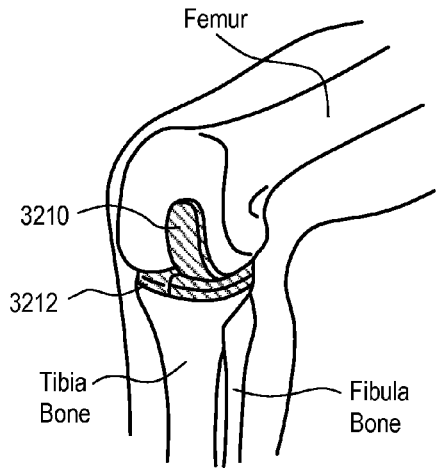
FIG. 31A
FIG. 31B
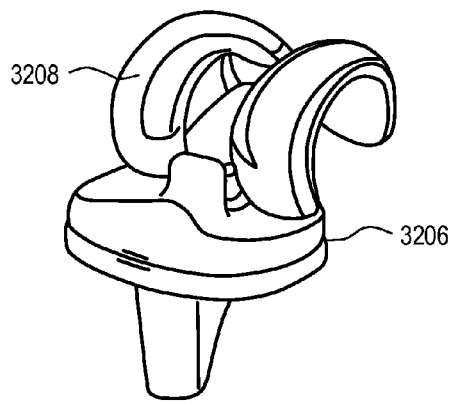
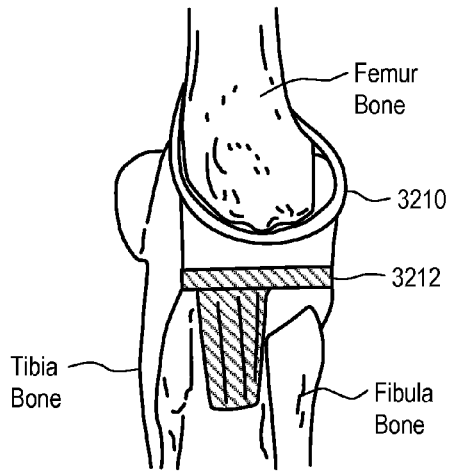
FIG. 32A
FIG. 32B

| Variable | (n = 12) |
|---|---|
| Mean lumen diameter (mm) | 3.17 ± 0.7 |
| Maximum lumen diameter (mm) | 3.4 ± 0.8 |
| Minimum lumen diameter (mm) | 2.9 ± 0.6 |
| Mean lumen area (mm$^2$) | 8.3 ± 3.5 |
| Mean stent diameter (mm) | 3.3 ± 0.5 |
| Maximum stent diameter (mm) | 3.4 ± 0.5 |
| Minimum stent diameter (mm) | 3.1 ± 0.5 |
| Mean stent area (mm$^2$) | 8.7 ± 2.6 |
| Mean [stent area – lumen area] (mm$^2$) | 0.36 ± 1.6 |
| Data given as mean ± standard deviation. The difference of the stent area minus the lumen area had positive (when the stent was well apposed) and negative (when the stent malapposed) values. ||

*FIG. 41*

QUANTITATIVE THREE-DIMENSIONAL IMAGING AND PRINTING OF SURGICAL IMPLANTS

RELATED APPLICATIONS

This application is a U.S. National Stage Filing under 35 U.S.C. 371 from International Application No. PCT/US2015/023213, filed on Mar. 28, 2015, and published as WO 2015/149043 A1 on Oct. 1, 2015, which claims the benefit of priority to U.S. provisional patent application No. 61/971,749, filed on Mar. 28, 2014, and entitled "QUANTITATIVE THREE-DIMENSIONAL IMAGING OF SURGICAL SCENES"; and to U.S. provisional patent application No. 62/096,518, filed on Dec. 23, 2014, and entitled "QUANTITATIVE THREE-DIMENSIONAL IMAGING AND PRINTING OF SURGICAL IMPLANTS"; each of which is incorporated herein by reference in its entirety.

FIELD

The invention relates in general to surgical endoscopy systems having associated image sensors, and more particularly, to determining three-dimensional coordinates of physical structures displayed in surgical images.

BACKGROUND

Quantitative three-dimensional (Q3D) vision provides numerical information about the actual physical (x, y, z) 3D coordinates of target points in a real world scene. With quantitative 3D vision, a person not only can obtain a three-dimensional perception of a real world scene, but also can obtain numerical information about physical dimensions of objects in the scene and physical distances between objects in the scene. In the past, some Q3D systems have been proposed that use time-of-flight related information or phase information to determine 3D information about a scene. Other Q3D systems have used structured light to determine 3D information about a scene.

The use of time-of-flight information is disclosed in U.S. Pat. No. 6,323,942, entitled, "CMOS-compatible three-dimensional image sensor IC", which discloses a three-dimensional imaging system that includes a two-dimensional array of pixel light sensing detectors fabricated on a common IC using CMOS fabrication techniques. Each detector has an associated high speed counter that accumulates clock pulses in number directly proportional to time-of-flight (TOF) for a system-emitted pulse to reflect from an object point and be detected by a pixel detector focused upon that point. The TOF data provides a direct digital measure of distance from the particular pixel to a point on the object reflecting the emitted light pulse. In a second embodiment, the counters and high speed clock circuits are eliminated, and instead each pixel detector is provided with a charge accumulator and an electronic shutter. The shutters are opened when a light pulse is emitted and closed thereafter such that each pixel detector accumulates charge as a function of return photon energy falling upon the associated pixel detector. The amount of accumulated charge provides a direct measure of round-trip TOF.

The use of time delay information is disclosed in U.S. Pat. No. 8,262,559, entitled, "Apparatus and method for endoscopic 3D data collection", which discloses a modulated measuring beam and a light-transmitting mechanism for conducting the measuring beam onto an area to be observed, where the light-transmitting mechanism includes an illuminating lens, in addition to a light-imaging mechanism for imaging a signal beam from the area to be observed at least onto a phase-sensitive image sensor. Time delays, which may correspond to differences in depth in the millimeter range, result in phase information that makes possible the production of an image that depicts depth and distance information.

The use of structured light to determine physical coordinates of objects in a visual image is disclosed in U.S. Pat. App. Pub. No. 2012/0190923, entitled "Endoscope"; and in C. Schmalz et al., "An endoscopic 3D scanner based on structured light", Medical Image Analysis, 16 (2012) 1063-1072. A triangulation method is used to measure the topography of a surface. Structured light in the form of projection rays, which may have a range of different color spectra, are incident upon and are reflected from a surface. The reflected rays are observed by a camera that is calibrated to use the reflected color spectra information to determine 3D coordinates of the surface. More specifically, the use of structured light typically involves shining a light pattern on a 3D surface, and determining physical distances based upon a deformation pattern of the light due to contours of the physical object.

An imager array camera has been built that includes a plurality of pixel arrays that can be used to compute scene depth information for pixels in the array. High resolution (HR) images are generated from multiple low resolution (LR) images. A reference viewpoint is selected and an HR image is generated as seen by that viewpoint. A parallax processing technique utilizes the effects of aliasing to determine pixel correspondences for non-reference images with respect to the reference image pixels. Fusion and superresolution are utilized to produce the HR image from the multiple LR images. See e.g., U.S. Pat. No. 8,514,491, entitled "Capturing and Processing Images using Monolithic Camera Array with Heterogeneous Imager"; U.S. Pat. App. Pub. No. 2013/0070060, entitled, "Systems and Methods for Determining Depth from multiple Views of a Scene that Include Aliasing using Hypothesized Fusion"; and K. Venkataraman et al., "PiCam: An ultra-Thin high Performance Monolithic Camera Array".

FIG. 1 is an illustrative drawing showing details of a known imager sensor 180 in accordance with some embodiments. The image sensor 180 includes an arrangement of sensors 184. Each sensor in the arrangement includes a two dimensional arrangement of pixels having at least two pixels in each dimension. Each sensor includes a lens stack 186. Each lens stack 186 has a corresponding focal plane 188. Each lens stack 186 creates a separate optical channel that resolves an image onto a corresponding arrangement of pixels disposed in its corresponding focal 188 plane. The pixels act as light sensors, and each focal plane 188 with its multiple pixels acts as an image sensor. Each sensor with its focal plane 188 occupies a region of the sensor arrangement different from regions of the sensor arrangement occupied by other sensors and focal planes.

FIG. 2 is an illustrative drawing showing a simplified plan view of the known arrangement of sensors 184 of FIG. 1 that includes sensors labeled as sensors $S_{11}$ through $S_{33}$. The imager sensor arrangement 184 is fabricated on a semiconductor chip to include a plurality of sensors $S_{11}$ through $S_{33}$. Each of the sensors $S_{11}$ through $S_{33}$ includes a plurality of pixels (e.g., 0.32 megapixels) and is coupled to peripheral circuitry (not shown) that includes independent read-out control and pixel digitization. In some embodiments, the sensors $S_{11}$ through $S_{33}$ are arranged into a grid format as illustrated in FIG. 2. In other embodiments, the sensors are arranged in a non-grid format. For example, the sensors may be arranged in a circular pattern, zigzagged pattern, scattered pattern, or irregular pattern including sub-pixel offsets.

Each individual pixel of the sensors 184 of FIGS. 1-2 includes a microlens pixel stack. FIG. 3 is an illustrative drawing of a known microlens pixel stack of the sensors of FIGS. 1-2. The pixel stack 800 includes a microlens 802, which is positioned above an oxide layer 804. Typically beneath the oxide layer 804 there may be a color filter 806, which is disposed above a nitride layer 808, which is disposed above a second oxide layer 810, which sits atop a silicon layer 812 that includes the active area 814 (typically a photodiode) of the individual pixel. The primary role of the microlens 802 is to gather the light incident on its surface and to focus that light onto the small active area 814. The pixel aperture 816 is determined by the spread of the microlens.

Additional information concerning the above-described known imager sensor arrangement architecture is provided in U.S. Pat. No. 8,514,491 B2 (filed Nov. 22, 2010), and in U.S. Patent Application Pub. No. US 2013/0070060 A1 (filed Sep. 19, 2012).

SUMMARY

In one aspect, systems and methods are provided to produce an artificial replacement anatomical structure, or prosthesis. The system produces a first quantitative three-dimensional (Q3D) model of an anatomical structure that includes target tissue. After removal of damaged or non-healthy tissue, the system produces a second Q3D model of the anatomical structure that includes remainder tissue in a location from which the target tissue has been removed. A third Q3D model of a replacement structure is produced based upon the first Q3D model and the second Q3D model. For example, after alignment, the system subtracts the second Q3D model data from the first Q3D model data in order to produce the third Q3D model. Furthermore, the system can then convert the third Q3D model to a three-dimensional (3D) model of the replacement structure in a format that is suitable for use by a 3D printing machine. A 3D printing machine is configured to receive the 3D model and to produce the replacement structure.

In another aspect, systems and methods are provided to generate an accurate Q3D model of a surgical scene. An anatomical structure is illuminated with a light source. The system positions, or "jitters", a Q3D endoscope at a combination of positions and orientations within a body cavity, in a known and controlled succession, so that multiple different image projections of the anatomical structure are successively acquired. The multiple successive positions and orientations of the Q3D endoscope are selected so that to provide redundant information in the acquired 3D images. The system produces an accurate Q3D model of the structure or scene by stitching together the multiple successive 3D images, based at least in part on the redundant information.

In another aspect, systems and methods for quantitative 3D evaluation of an implant performance are provided. The system comprises a Q3D endoscope and a processor that produces a first Q3D model of the internal anatomical structure targeted to receive a surgical implant. Based at least in part on the first Q3D model, the system produces an output representative of the size of the implant that optimally fits the anatomic structure. With the implant deployed in place, the system produces a different Q3D model of the structure and of the implant. The system produces an output representative of a clinical performance feature of the implant. For example, the output can be configured to be quantitatively representative of the effective 3D coverage length of a stent, of the vessel cross-sectional coverage of a stent, of the 3D dynamic closure of an artificial heart valve, of the 3D motion of a partial knee replacement implant, etc.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 25A is an illustrative drawing showing an example view of an anatomical structure before a surgical procedure in accordance with some embodiments.

FIG. 25B is a side view cross-section view generally along dashed lines A-A from perspective 1-1 in FIG. 25A showing contours of the example damaged portion in greater detail.

FIG. 26A is an illustrative drawing showing an example view of an anatomical structure after the surgical procedure removing damaged or diseased bone tissue and leaving behind a void bounded by remaining healthy tissue in accordance with some embodiments.

FIG. 26B is a side view cross-section view generally along dashed lines A-A from perspective 1-1 in FIG. 26A showing contours of the example healthy or uninjured region after removal of the diseased or damaged bone tissue.

FIG. 31A is an illustrative drawing showing a front elevation view of knee bones with an example total knee bone replacement prosthetic device.

FIG. 31B is an illustrative drawing showing a front elevation view of knee bones with a partial knee replacement prosthetic device.

FIG. 32A is an illustrative drawing showing a prosthetic tibial plate and femoral component of the example total knee bone replacement prosthetic device of FIG. 31A.

FIG. 32B is an illustrative drawing showing a rear view of knee bones with the partial knee replacement prosthetic device of FIG. 31B

FIG. 41 illustrates an example of quantitative criteria that can be used to quantitatively evaluate stent implantation performance.

DESCRIPTION OF EMBODIMENTS

Figure 1:
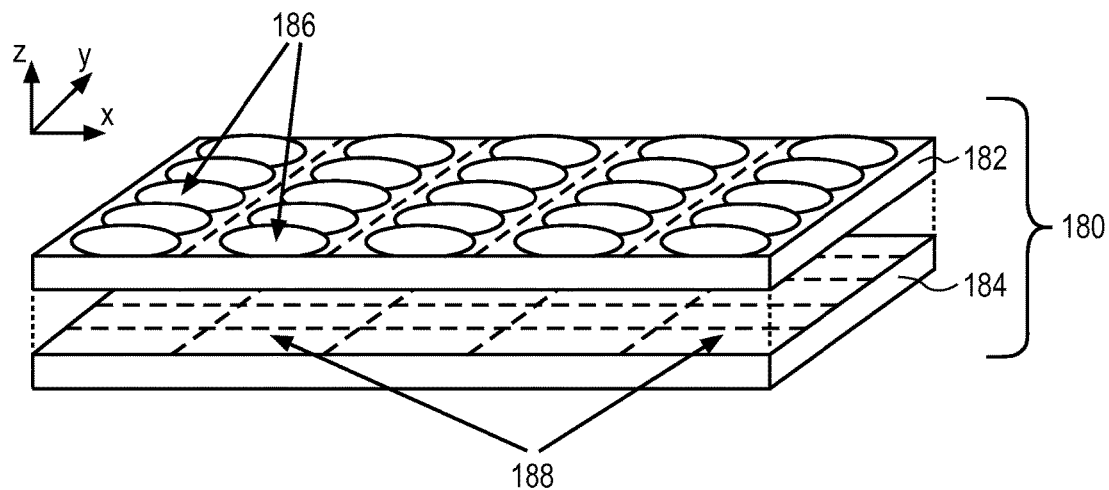
FIG. 1 is an illustrative drawing showing details of a known imager sensor.
Figure 2:
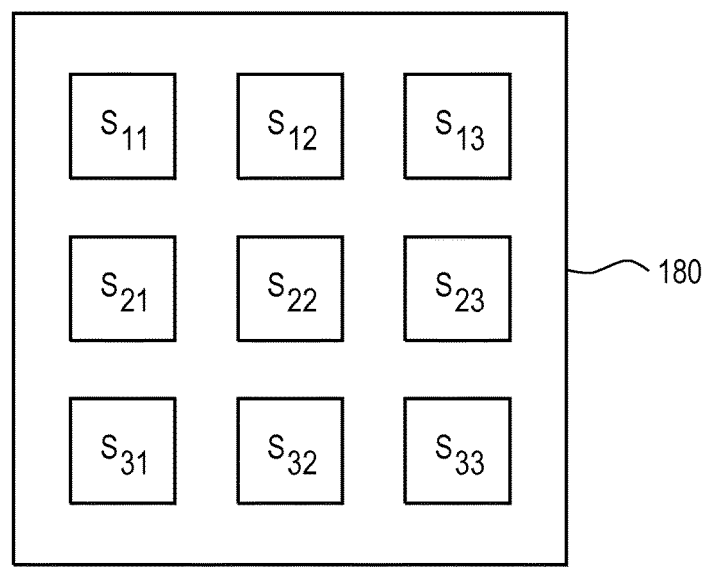
FIG. 2 is an illustrative drawing showing a simplified plan view of a known sensor array of the imager sensor of FIG. 1.
Figure 3:
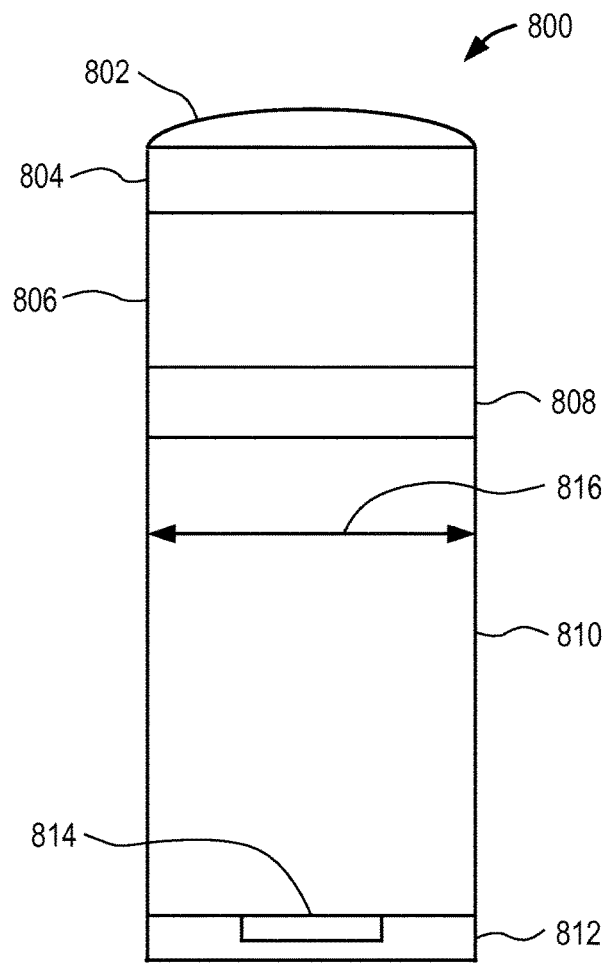
FIG. 3 is an illustrative drawing of a known microlens pixel stack of a pixel within a sensor of the sensor array of FIG. 2.

The following description is presented to enable any person skilled in the art to create and use a surgical endoscopy system having multiple image sensors, each sensor including a pixel array that is separate from pixel arrays of other sensors, so as to determine three-dimensional coordinates of physical structures within a field of view of the image sensors. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. In other instances, well-known machine components, processes and data structures are shown in block diagram form in order not to obscure the disclosure with unnecessary detail. Identical reference numerals may be used to represent different views of the same item in different drawings. Flow diagrams in drawings referenced below are used to represent processes. A computer system may be configured to perform some of these processes. Modules within flow diagrams representing computer implemented processes represent the configuration of a computer system according to computer program code to perform the acts described with reference to these modules. Thus, the inventive subject matter is not intended to be limited to the embodiments shown, but is to be accorded the widest scope consistent with the principles and features disclosed herein.

Brief Overview

In accordance with some embodiments, an imager that includes that includes a sensor array is associated with an endoscope. The image sensor array includes multiple sensors, and each sensor includes an array of pixels. A portion of the endoscope is inserted into a human body cavity, and a target object in a field of view of the image sensor array is illuminated using a light source. A physical location and/or dimensions of the target object is determined based upon images of the target object projected onto individual sensors of the array.

Figure 4:
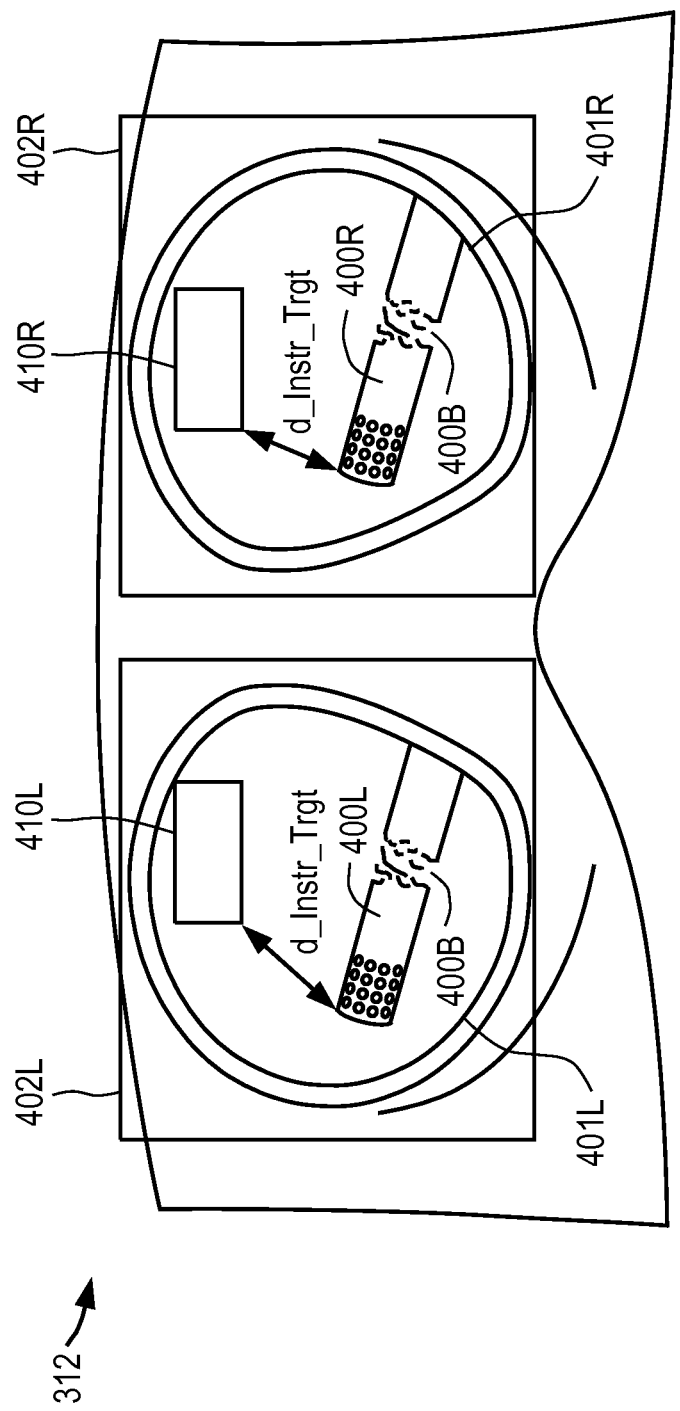
FIG. 4 is an illustrative drawing showing a perspective view of a surgical scene through a viewer in accordance with some embodiments.

FIG. 4 is an illustrative drawing showing a perspective view of a surgical scene through a viewer 312 in accordance with some embodiments. A viewing system having two viewing elements 401R, 401L can provide a good 3D viewing perspective. Numerical values representing physical dimension and/or location information for physical structures in the surgical scene are shown overlaid onto the surgical scene image. For example, a numerical distance value "d_Instr_Trgt" is shown displayed within the scene between instrument 400 and target 410.

Teleoperation Medical System

Teleoperation refers to operation of a machine at a distance. In a minimally invasive teleoperation medical system, a surgeon may use an endoscope that includes a camera to view a surgical site within a patient's body. Stereoscopic images have been captured, which allow the perception of depth during a surgical procedure. A camera system, which is mounted on an endoscope and which includes an imager sensor array, provides quantitative three-dimensional information plus color and illumination data that can be used to generate three-dimensional images in accordance with some embodiments.

Figure 5:
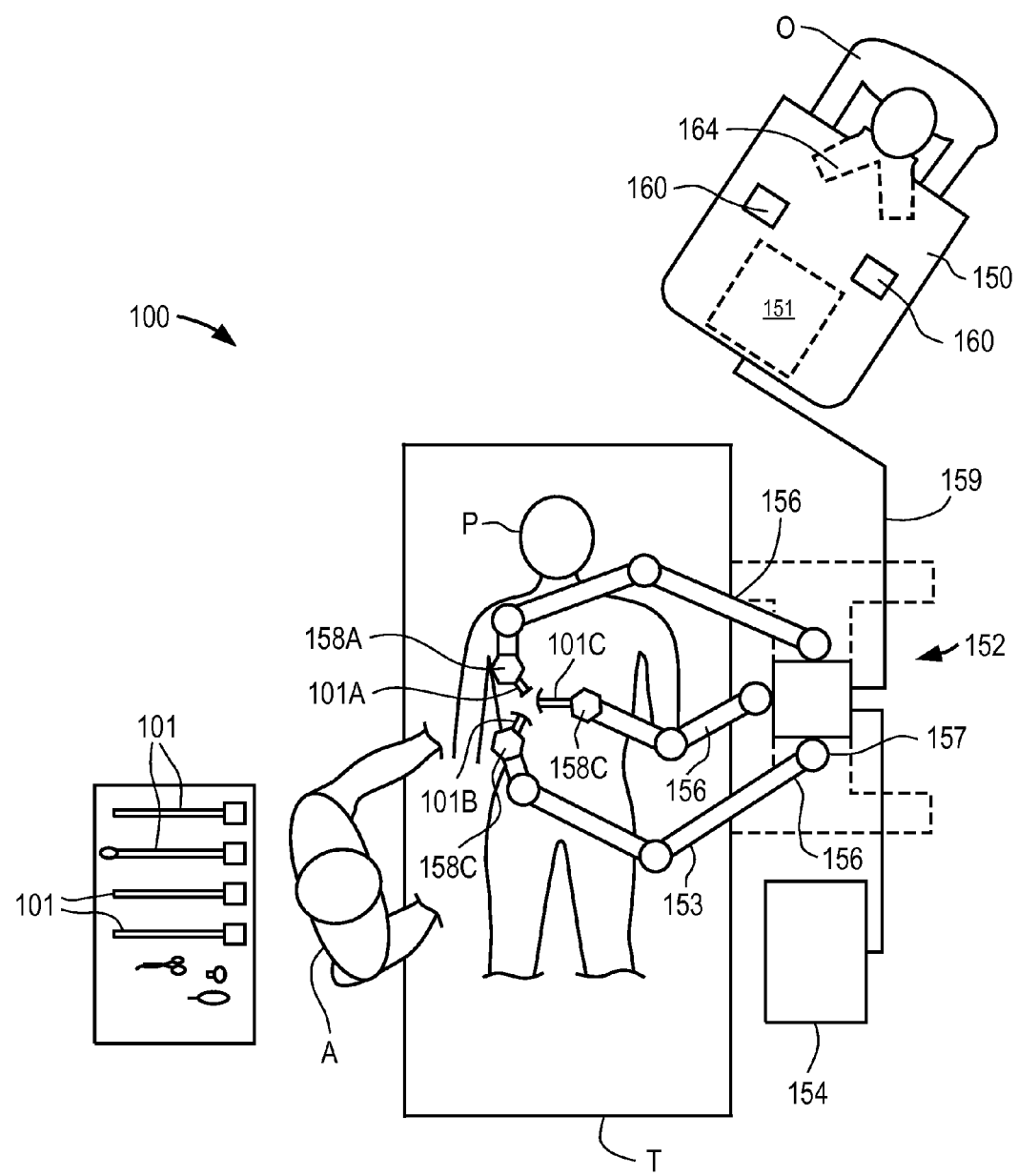
FIG. 5 is an illustrative block diagram of a teleoperation surgery system to perform minimally invasive surgical procedures using one or more mechanical arms in accordance with some embodiments.

FIG. 5 is an illustrative block diagram of a teleoperation surgery system 100 to perform minimally invasive surgical procedures using one or more mechanical arms 158 in accordance with some embodiments. Aspects of system 100 include telerobotic and autonomously operating features. These mechanical arms often support an instrument. For instance, a mechanical surgical arm (e.g., the center mechanical surgical arm 158C) may be used to support an endoscope with a stereo or three-dimensional surgical image capture device 101C, such as an endoscope associated a Q3D image sensor array. The mechanical surgical arm 158C may include a sterile adapter, or a clamp, clip, screw, slot/groove, or other fastener mechanism to mechanically secure an endoscope that includes the image capture device 101C to the mechanical arm. Conversely, the endoscope with image capture device 101C may include physical contours and/or structures complementary to those of the mechanical surgical arm 158C so as to securely interfit with them.

A user or operator O (generally a surgeon) performs a minimally invasive surgical procedure on patient P by manipulating control input devices 160 at a master control console 150. The operator can view video frames of images of a surgical site inside a patient's body through a stereo display device 164, which includes the viewer 312 described above with reference to FIG. 4. A computer 151 of the console 150 directs movement of teleoperationally controlled endoscopic surgical instruments 101A-101C via control lines 159, effecting movement of the instruments using a patient-side system 152 (also referred to as a patient-side cart).

The patient-side system 152 includes one or more mechanical arms 158. Typically, the patient-side system 152 includes at least three mechanical surgical arms 158A-158C (generally referred to as mechanical surgical arms 158) supported by corresponding positioning set-up arms 156. The central mechanical surgical arm 158C may support an endoscopic camera 101C suitable for capture of Q3D information for images within a field of view of the camera. The mechanical surgical arms 158A and 158B to the left and right of center may support instruments 101A and 101B, respectively, which may manipulate tissue.

Figure 6:
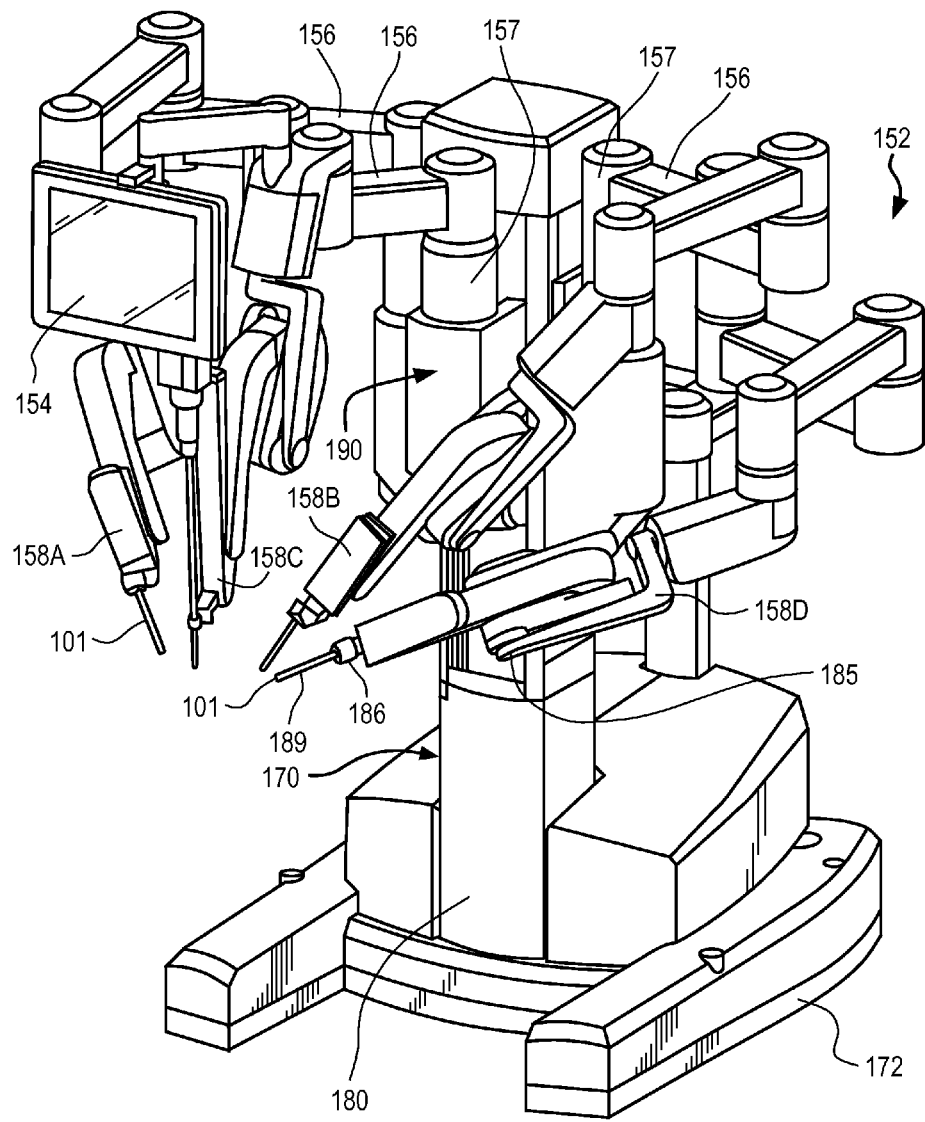
FIG. 6 is an illustrative perspective view of a patient-side system of the system of FIG. 5 in accordance with some embodiments.

FIG. 6 is an illustrative perspective view of the patient-side system 152 in accordance with some embodiments. The patient-side system 152 comprises a cart column 170 supported by a base 172. One or more mechanical insertion surgical arms/links 158 are respectively attached to one or more set-up arms 156 that are a part of the positioning portion of the patient-side system 152. Situated approximately at a central location on base 172, the cart column 170 includes a protective cover 180 that protects components of a counterbalance subsystem and a braking subsystem from contaminants.

Excluding a monitor arm 154, each mechanical surgical arm 158 is used to control instruments 101A-101C. Moreover, each mechanical surgical arm 158 is coupled to a set-up arm 156 that is in turn coupled to a carriage housing 190 in one embodiment of the invention. The one or more mechanical surgical arms 158 are each supported by their respective set-up arm 156, as is illustrated in FIG. 6.

The mechanical surgical arms 158A-158D may each include one or more displacement transducers, orientational sensors, and/or positional sensors 185 to generate raw uncorrected kinematics information to assist in initial acquisition by a tracking system and tracking of instruments. The instruments may also include a displacement transducer, a positional sensor, and/or orientation sensor 186 in some embodiments of the invention. Moreover, one or more instruments may include a marker 189 to assist in acquisition and tracking of the instruments.

Additional information about a teleoperation medical system is provided in U.S. Patent Application Pub. No. US 2012/0020547, (filed Sep. 30, 2011).

Endoscopic Imager System

Figure 7A:
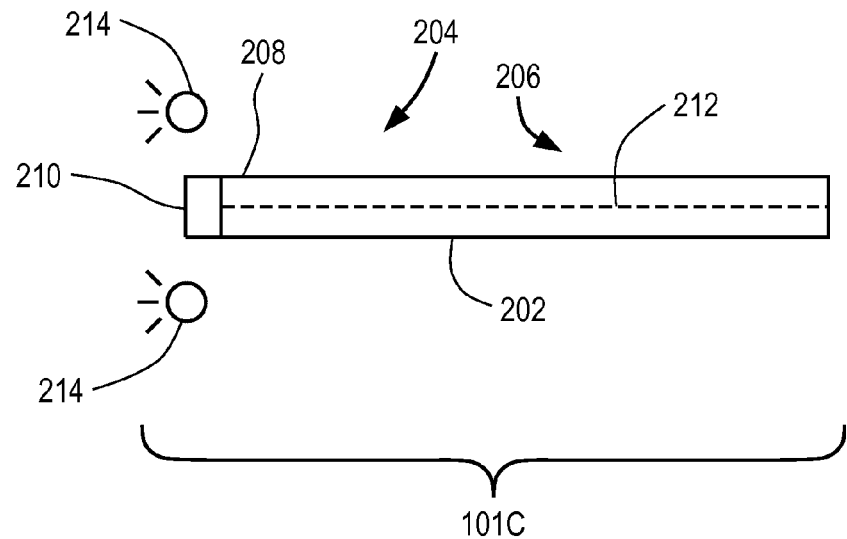
FIG. 7A is an illustrative drawing of a first endoscope that includes a first image capture system in accordance with some embodiments.

FIG. 7A is an illustrative drawing of a first endoscope with a first image capture system 101C in accordance with some embodiments. The image capture system 101C includes an endoscope that includes elongated portion 202, which includes a first end portion 204 and a second end portion 206 and a tip portion 208 of the first end portion 204. The first end portion 204 is dimensioned to be inserted into a human body cavity. A sensor array 210, which includes multiple image sensors (not shown), is coupled at the tip portion 208 of the first end portion 204. In accordance with some embodiments, each sensor in the sensor array 210 includes an array of pixels. The elongated portion 202 has a length sufficient to position the tip portion 208 close enough to a target object within the body cavity so that the object can be imaged by the imager sensor array 210. In accordance with some embodiments, the second end portion 206 may include physical contours and/or structures (not shown), as generally described above, so as to securely interfit with a mechanical arm (not shown). The elongated portion 202 also includes one or more electronic signal paths 212 to electronically communicate information with the imager sensor array 210. A light source 214 is disposed to illuminate the object to be imaged. In accordance with some embodiments, the light source 214 can be unstructured light, white light, color filtered light, or light at some selected wavelength, for example. In accordance with some embodiments the light source 214 is located at tip 208, and in other embodiments it is optionally located separately from endoscope 101C.

Figure 7B:
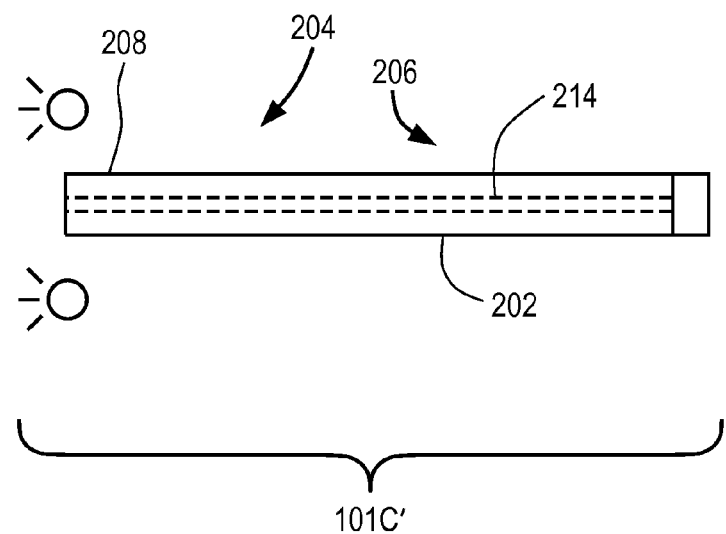
FIG. 7B is an illustrative drawing of a second endoscope that includes a second image capture system in accordance with some embodiments.

FIG. 7B is an illustrative drawing of a second endoscope with a second image capture system 101C2, in accordance with some embodiments. Aspects of the second image capture system 101C2 that are essentially the same as those of the first endoscope with the first image capture system 101C are indicated by identical reference numerals and are not described again. An input to a light pipe input, such as a rod lens, is disposed at the tip portion 208 of the first end portion 204. A light pipe body extends within the elongate portion 202 so as to transmit an image received as the light pipe input to the imager sensor array 210, which is physically displaced from the tip portion 208. In some embodiments, the imager sensor array 210 is displaced far enough from the tip portion 208 so that the imager sensor array 210 is located outside the body cavity during observation of objects within the cavity.

Figure 8:
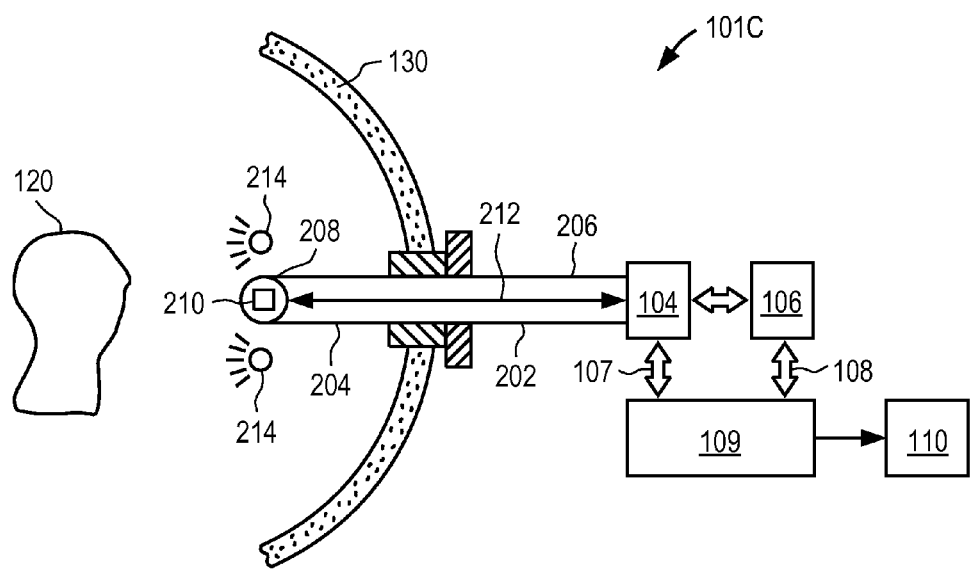
FIG. 8 is illustrative block diagram showing control blocks associated with the first endoscope that includes the first image capture system of FIG. 7A and showing the system in operation, in accordance with some embodiments.

FIG. 8 is illustrative block diagram showing control blocks associated with the first endoscope 101C with the first image capture system 101C of FIG. 7A and showing the system in operation, in accordance with some embodiments. Images captured by the imager sensor array 210 are sent over a data bus 212 to a video processor 104, which communicates via bus 105 with a controller 106. The video processor 104 may comprise a camera control unit (CCU) and a video signal detector (VSD) board. The CCU programs or controls various settings of the imaging sensor 210, such as brightness, color scheme, white balance, etc. The VSD processes the video signal received from the imaging sensor. Alternatively, the CCU and VSD are integrated into one functional block.

In accordance with some embodiments a processor system that includes one or more than one processor is configured to perform processor functions. In some embodiments the processor system includes multiple processors configured to operate together to perform the processor functions described herein. Thus, reference herein to at least one processor configured to perform one or more functions includes a processor system in which the functions may be performed by one processor alone or by multiple processors working together.

In one implementation, the controller 106, which includes a processor and a storage device (not shown) computes the physical quantitative 3D coordinates of the points in a scene adjacent the tip 208 of the elongate portion 202 and drives both the video processor 104 and a 3D display driver 109 to compose 3D scenes, which then can be displayed on a 3D display 110. In accordance with some embodiments, Q3D information about a surgical scene is generated, such as numerical indicia of dimensions of surface contours of objects in a scene or distances from objects within the surgical scene, for example. As explained more fully below, the numerical Q3D depth information can be used to annotate a stereoscopic image of a surgical scene with distance information or surface contour information.

Data buses 107 and 108 exchange information and control signals among the video processor 104, the controller 106, and the display driver 109. In some embodiments, these elements can be integrated with the image sensor array 210 inside the body of the endoscope. Alternatively, they can be distributed internally and/or externally to the endoscope. The endoscope is shown positioned, via a cannula 140, to penetrate body tissue 130 in order to provide visualize access to a surgical scene that includes a target 120. Alternatively, the endoscope and one or more instruments may also pass through a single opening—a single incision or natural orifice—to reach a surgical site. The target 120 can be an anatomic target, another surgical instrument, or any other aspect of the surgical scene inside a patient's body.

An input system 112 receives the 3D visual representation and provide it to processor 106. The input system 112 may include a storage device coupled to an electronic communication bus (not shown) that receives a 3D model such as a CRT or MRI from a system (not shown) that generates the 3D model. Processor 106, for example, can be used to compute the alignment intended between the Q3D model and the 3D visual representation. More particularly, without limitation, input system 112 may include a processor configured to establish an Ethernet communication connection between system 152 and an imaging system (not shown), such as a MRI, CT or ultrasound imaging system. Other imaging systems may be used. Other types of communication connections may be used, such as Bluetooth, WiFi, optical, etc. Alternatively, system 152 and the imaging system may be integrated in one larger system. The result of the alignment process may be saved in the storage device associated with processor 106, provided for further manipulation to external devices or system or displayed as shown in FIG. 25.

Example of Q3D Information Added to an Image of a Scene

Referring once again to FIG. 4 is an illustrative drawing showing a perspective view of a viewer 312 of the master control console 150 of FIG. 5 in accordance with some embodiments. In accordance with some embodiments, to provide a three-dimensional perspective, the viewer 312 includes stereo images for each eye. As shown, a left image 400L and a right image 400R of the surgical site include any instruments 400 and a target 410 respectively in a left viewfinder 401L and a right viewfinder 401R. The images 400L and 400R in the viewfinders may be provided by a left display device 402L and a right display device 402R, respectively. The display devices 402L,402R may optionally be pairs of cathode ray tube (CRT) monitors, liquid crystal displays (LCDs), or other type of image display devices (e.g., plasma, digital light projection, etc.). In the preferred embodiment of the invention, the images are provided in color by a pair of color display devices 402L, 402R; such as color CRTs or color LCDs. To support backward compatibility with existing devices, stereoscopic display devices 402L and 402R may be used with a Q3D system. Alternatively, the Q3D imaging system can be connected to 3D monitors, 3D TVs, or to autostereoscopic displays, such as a display that does not require use of 3D effect eye glasses.

A viewing system having two viewing elements 401R, 401L can provide a good 3D viewing perspective. The Q3D imaging system supplements this viewing perspective with physical dimension information for physical structures in the surgical scene. The stereo viewer 312 used in conjunction with a Q3D endoscopy system, can display Q3D information overlayed onto the stereo image of the surgical scene. For example, as shown in FIG. 4, the numerical Q3D distance value "d_Instr_Trgt" between instrument 400 and target 410 can be displayed within stereo viewer 312.

An explanation of a video stereo viewing system that can be used to overlay physical location and dimension information onto a 3D perspective of a surgical scene is provided in U.S. Patent Application Pub. No. U.S. 2012/0020547, (filed Sep. 30, 2011), paragraphs [0043]-[0053] and corresponding drawings, which is expressly incorporated herein by reference.

Processing Quantitative Three-Dimensional Physical Information

Figure 9:
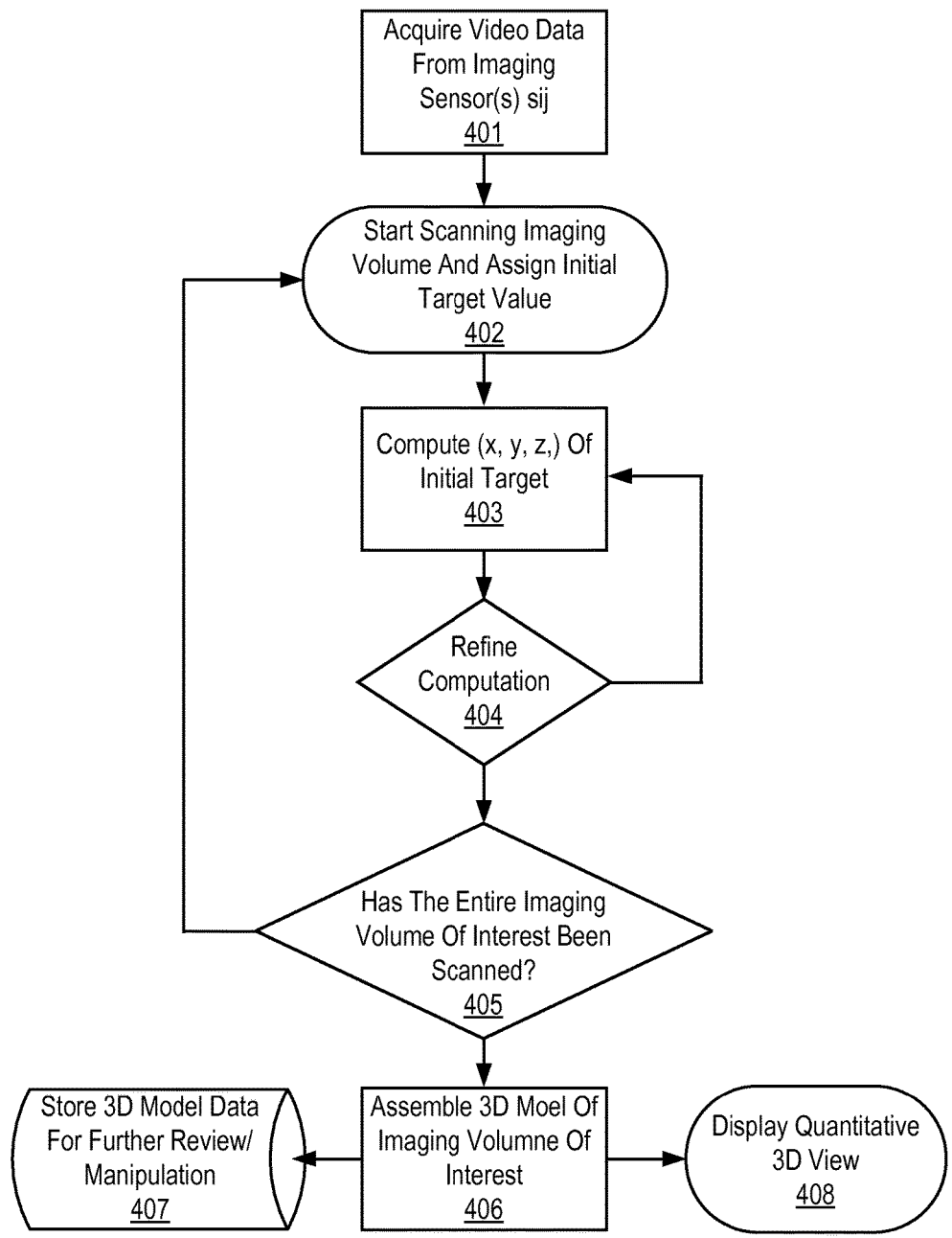
FIG. 9 is an illustrative flow diagram representing a process to determine a quantitative three dimensional location of a physical target in accordance with some embodiments.

FIG. 9 is an illustrative flow diagram representing a process to determine a quantitative three-dimensional location of a physical target in accordance with some embodiments. The process is described with reference to the endoscope with image capture system 101C of the embodiment of FIG. 8. Module 401 configures the controller 106 to acquire video data from imaging sensors $S_{ij}$. It will be appreciated that although the image sensor array 210 "images" an entire field of view, different sensors and different pixels within different sensors in image sensor array 210 may be illuminated by image projections from different object points within the field of view. The video data, for example, may include color and light intensity data. Each pixel of each sensor may provide one or more signals indicative of the color and intensity of an image projected onto it. Module 402 configures the controller to systematically select targets from a selected region of interest in a physical world view. Module 403 configures the controller to commence the computation of the target 3D coordinates (x, y, z) with an initial $(x_0, y_0, z_0)$ set. The algorithm then checks the coordinates for consistency, by using image diversity data from all sensors $S_{ij}$ that receive a projected image of the target. The coordinate computation is refined at decision module 404 until an acceptable accuracy is reached. Decision module 404 also configures the controller to determine whether the currently computed physical location is sufficiently accurate. In response to a determination that the currently computed location is not accurate enough, control flows back to module 403 to try a different possible physical location. In response to a determination that the currently computed location is sufficiently accurate, module 405 configures the controller to determine whether the entire region of interest has been scanned. In response to a determination that the entire region of interest has not been scanned, control flows back to module 402 and a different target is selected. In response to a determination that the entire region of interest has been scanned, control flows to module 406, which configures the controller to assemble a three-dimensional model of the imaging volume of interest. Assembly of a 3D image of a target based upon three-dimensional information indicating the physical position of structures of the target is known to persons of ordinary skill in the art and need not be described herein. Module 407 configures the controller to store the 3D model developed using the physical position information determined for multiple targets for further review and manipulation. For example, the 3D model could be used at a later time for surgical applications, such as sizing an implant for the particular dimensions of a patient's organ. In yet a different example, when a new surgical instrument 101 is installed on the robotic system 152, it may be necessary to call back the 3D model and display it on display 110 in order to reference the new instrument to the previous surgical scene. Module 407 may also store the result of the alignment between the 3D visual representation and the Q3D model. Module 408 configures the controller to use the physical position information determined for multiple targets to display a quantitative 3D view. An example of a Q3D view is the distance value "d_Instr_Trgt" shown in FIG. 4.

It is noted that a stereoscopic display creates the illusion of viewing in three dimensions. However, an actual 3D display presents a 3D image, such as a holographic image or an image projected onto a curved surface. Typically, a 3D display allows the view to move to change viewing perspective.

Figure 10:
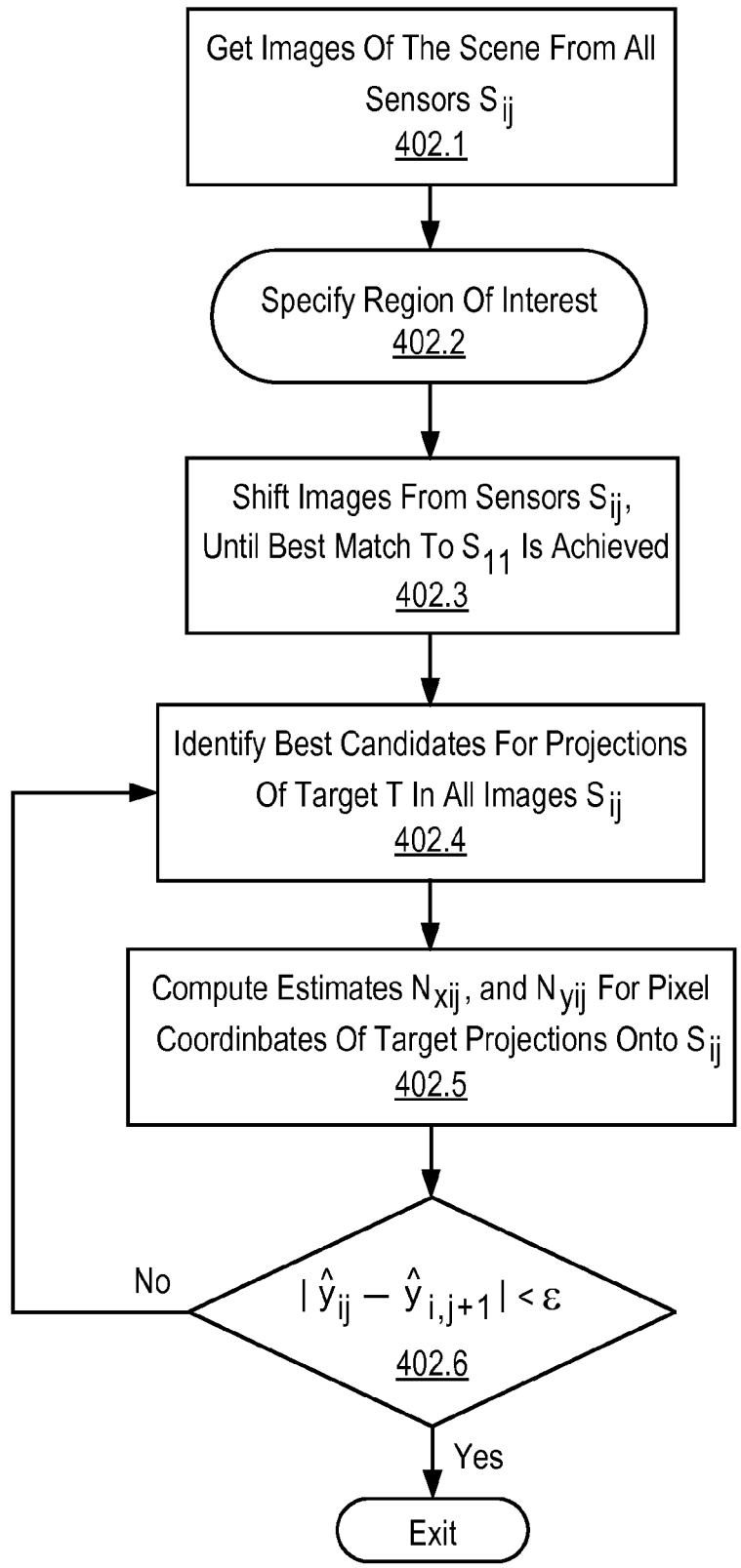
FIG. 10 is an illustrative flow diagram showing certain details of a process generally corresponding to module FIG. 9 to systematically select targets in accordance with some embodiments.

FIG. 10 is an illustrative flow diagram showing certain details of a process generally corresponding to module 402 of FIG. 9 in accordance with some embodiments. Module 402.1 configures the controller to capture images of a physical world scene from all sensors in the sensor array 210. Module 402.2 configures the controller to specify a region of interest from within the captured scene. Module 402.3 configures the controller to search for a best match as between scene images within the region of interest so as to identify pixel locations in different sensors that are illuminated by projections of the same target. As explained later, the best matching may be achieved, without limitation, by shifting the individual images from sensors $S_1$ until maximizing two-dimensional cross-correlation function between the shifted image and a reference image. The reference image, for example, may be the scene image received from sensor $S_{11}$. Module 402.4 configures the controller to identify candidate pixels illuminated by projections from the same target. Module 402.5 configures the controller to compute two or more pixel coordinates $(N_x, N_y)$ coordinates for the selected target to determine whether the candidate pixels are illuminated by a projection from the same target.

Decision module 402.6 determines whether the computed 2D pixel coordinate values indicate that the candidate pixels are illuminated by a projection from the same target. The image diversity caused by viewing the same scene with multiple sensors $S_{ij}$ plays a role in correctly identifying ($N_x$, $N_y$) associated with a specific target in the various individual images $S_{ij}$. For example, in accordance with some embodiments, assuming a simplified scenario where only three sensors are used, $S_{11}$, $S_{12}$ and $S_{13}$, if the triplet of 2D pixel coordinates [($Nx_{11}$, $Ny_{11}$), ($Nx_{12}$, $Ny_{12}$), ($Nx_{13}$, $Ny_{13}$)] are not corresponding to projections of the same target onto [$S_{11}$, $S_{12}$ and $S_{13}$] then the quantities $\hat{y}_{12}$ and $\overline{y}_{13}$ (which are estimates of the projection shift in the y direction) will yield different values. According the equations presented later, $\hat{y}_{12}$ and $\hat{y}_{13}$ should be equal if pixel coordinates ($Nx_{11}$, $Ny_{11}$), ($Nx_{12}$, $Ny_{12}$), ($Nx_{13}$, $Ny_{13}$) come from projections of the same target.

$$\hat{y}_{12} = \frac{Ny_{11}}{Ny_{11} - Ny_{12}} \quad (402.5-1)$$

$$\hat{y}_{13} = 2 \cdot \frac{Ny_{11}}{Ny_{11} - Ny_{13}} \quad (402.5-2)$$

If $\hat{y}_{12}$ and $\hat{y}_{13}$ are not approximately equal then control flows back to module 402.4 and to refine the best candidates for target projections onto sensor planes $S_{ij}$. As mentioned, the above is just a simplified implementation of the algorithm. In general, as shown in FIG. 10 module 402.6, the norm of the difference between $\hat{y}_{i,j}$ and $\hat{y}_{i,j+1}$ should be less than an acceptable tolerance c in order for module 402 to complete its iterations. A similar restriction should be met for the corresponding estimates for the x axis, $\hat{x}_{i,j}$ and $\hat{x}_{i,j+1}$. In response to a determination that the computed 2D pixel coordinate values ($N_x$, $N_y$) do indicate that the candidate pixels are illuminated by a projection from the same target, then control flows to module 403.

It will be appreciated that each pixel directly captures color and intensity information from a world scene. Moreover, in accordance with the above process, each pixel is associated with the (x, y, z) coordinates of the physical object in the world view that is projected onto the pixel. Thus, color information, illumination intensity information and physical location information, i.e. the location of the physical object that projected the color and illumination, can be associated with a pixel in a non-transitory computer readable storage device. The following Table 1 illustrates this association.

TABLE 1

| Pixel Identifier | Color Value | Intensity Value | Location (x, y, z) |
| --- | --- | --- | --- |

Examples of Determining Q3D Information

Example of Projection Matching

Figure 11:
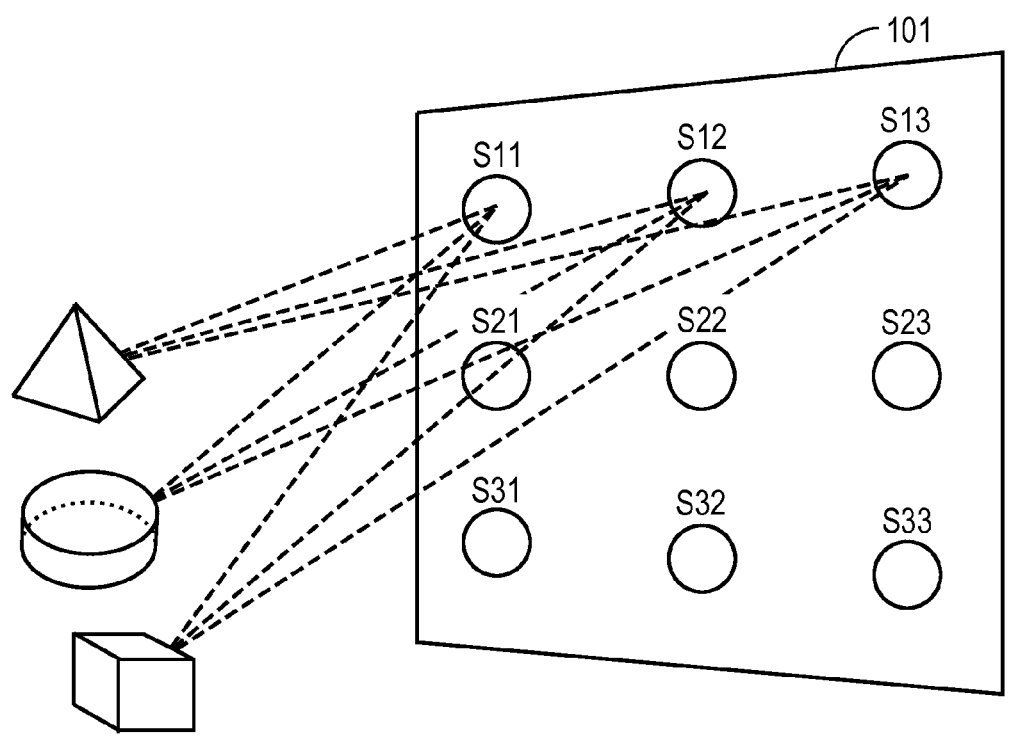
FIG. 11 is an illustrative drawing of an example sensor imager array that includes multiple sensors and that is disposed to have a field of view that encompasses an illustrative three dimensional physical world scene that includes three illustrative objects in accordance with some embodiments.

FIG. 11 is an illustrative drawing of an example sensor array 210 that includes an array of sensors $S_{11}$-$S_{33}$ that is disposed to have a field of view that encompasses an illustrative three-dimensional physical world scene that includes three illustrative objects in accordance with some embodiments. Each sensor $S_{ij}$ in the array includes a two-dimensional arrangement of pixels having at least two pixels in each dimension. Each sensor includes a lens stack that creates a separate optical channel that resolves an image onto a corresponding arrangement of pixels disposed in a focal plane of the lens stack. Each pixel acts as a light sensor, and each focal plane with its multiple pixels acts as an image sensor. Each sensor $S_{11}$-$S_{33}$ with its focal plane occupies a region of the sensor array different from regions of the sensor array occupied by other sensors and focal planes. Suitable known image sensor arrays are disclosed in U.S. Pat. No. 8,514,491 (filed Nov. 22, 2010) and in U.S. Patent Application Pub. No. U.S. 2013/0070060 (filed Sep. 19, 2012), which are described above.

In accordance with some embodiments, the sensors are characterized by a $N_x$ and $N_y$, their total number of pixels in the x and y directions, and by field of view angles, $\theta_x$ and $\theta_y$. In some embodiments, the sensor characteristics for the x and y axes are expected to be the same. However, in alternative embodiments, the sensors have asymmetric x and y axis characteristics. Similarly, in some embodiments, all sensors will have the same total number of pixels and the same field of view angle. The sensors are distributed across the sensor array 210 in a well-controlled manner. For example, the sensors may be at $\delta$ distance apart on the two-dimensional grid shown. The sensor placement pitch $\delta$ may be symmetric or asymmetric across such grid.

In the embodiment shown in FIG. 11, the sensors are arranged in a rectangular grid in which sensors $S_{11}$-$S_{13}$ occupy a top row, sensors $S_{21}$-$S_{23}$ occupy a middle row, and sensors $S_{31}$-$S_{33}$ occupy a bottom row. Each sensor includes N rows of pixels and N columns of pixels. Light rays, indicated by dashed lines, produced by a light source are reflected from each of a triangular-shaped first object, a spherical-shaped second object, and a rectangular-shaped third object, to each sensor of the imager array. For illustration purposes, only rays to sensors $S_{11}$, $S_{12}$ and $S_{13}$ in the top row are shown. The light source may be non-structured white light or ambient light, for example. Alternatively, the light source may provide light at a selected wavelength, such as in the visible or infrared spectrums, or the light may be filtered or split to provide a selected wavelength (e.g., color) or range of wavelengths (e.g., range of colors), for example. It will be appreciated that light rays are similarly reflected from each of the objects to sensors $S_{21}$-$S_{33}$. However, in order to simplify the explanation, these other light rays are not shown.

Figure 12:
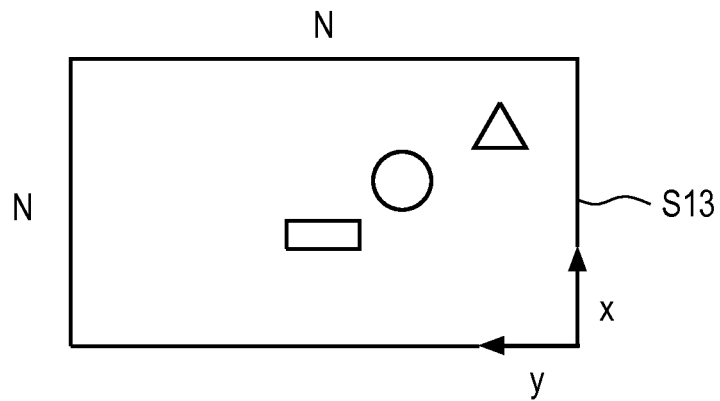
FIG. 12 is an illustrative drawing representing projections of the multiple physical objects of FIG. 11 onto multiple sensors in accordance with some embodiments.
Figure 12:
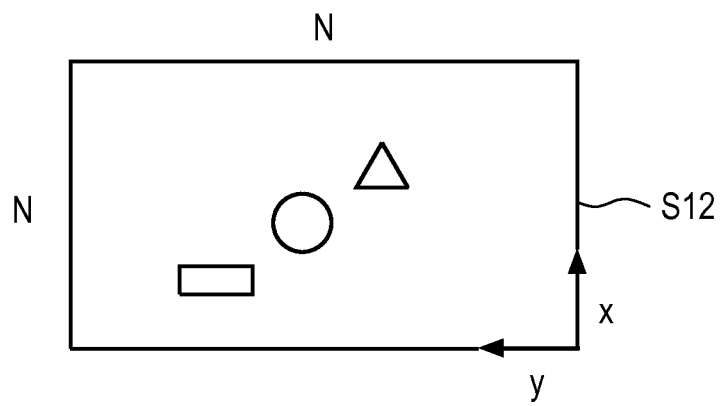
Figure 12:
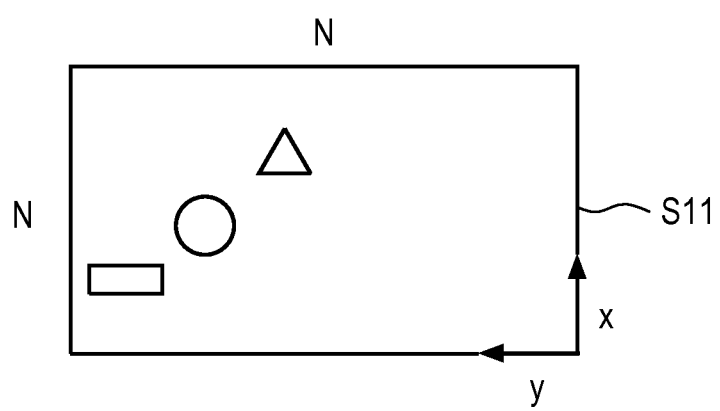

In accordance with modules 401 and 402.1, sensors of the sensor array 210 separately capture images from a world view. FIG. 12 is an illustrative drawing representing projections of the three objects of FIG. 11 onto the sensors $S_{ij}$ (only $S_{11}$, $S_{12}$, and $S_{13}$ are shown) in accordance with some embodiments. A person of ordinary skill in the art will appreciate that the reflected light rays incident upon the sensors project images of the objects that are in the field of view. More specifically, the rays of light reflected from the objects in the field of view that are incident upon multiple different image sensors of the imager array produce multiple perspective projections of the objects from three dimensions to two dimensions, i.e. a different projection in each sensor that receives the reflected rays. In particular, the relative location of projections of the objects is shifted from left to right when progressing from $S_{11}$ to $S_{12}$ to $S_{13}$. Image sensor pixels that are illuminated by incident light rays produce electrical signals in response to the incident light. Accordingly, for each image sensor, a pattern of electrical signals is produced by its pixels in response to the reflected rays that indicates the shape and location of the image projection within that image sensor.

Figure 13:
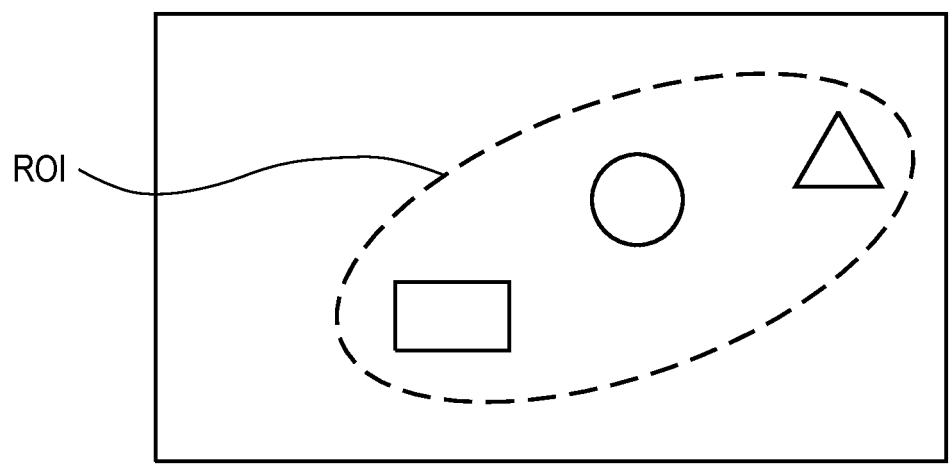
FIG. 13 is an illustrative drawing indicating selection of a region of interest from within a real-world scene in accordance with some embodiments.

In accordance with module 402.2, a region of interest is selected from the world scene. FIG. 13 is an illustrative drawing indicating selection of a region of interest from within the scene. In this example, the triangular-shaped first object, spherical-shaped second object, and rectangular-shaped third object all are in the selected region of interest. This step can be achieved by accepting input from an operator, or it can be automatically performed using a computer configured by software in a prescribed manner, or by combination of operator inputs and automatic software-controlled selection. For example, in some embodiments, the world scene may show an internal cavity of the human anatomy, and the objects may be internal body organs, or surgical instruments, or portions thereof. A surgeon may receive real time visual imagery from within the internal cavity and may see tissue regions of the human anatomy and a portion of the surgical instruments projecting within the body cavity. The surgeon may specify those objects within the field of view for which location information is to be determined through well-known techniques, such as a telestration video marker. Alternatively or in addition to such operator request, an automated process such as an edge detection algorithm can be used to specify a region of interest (ROI).

Figure 14:
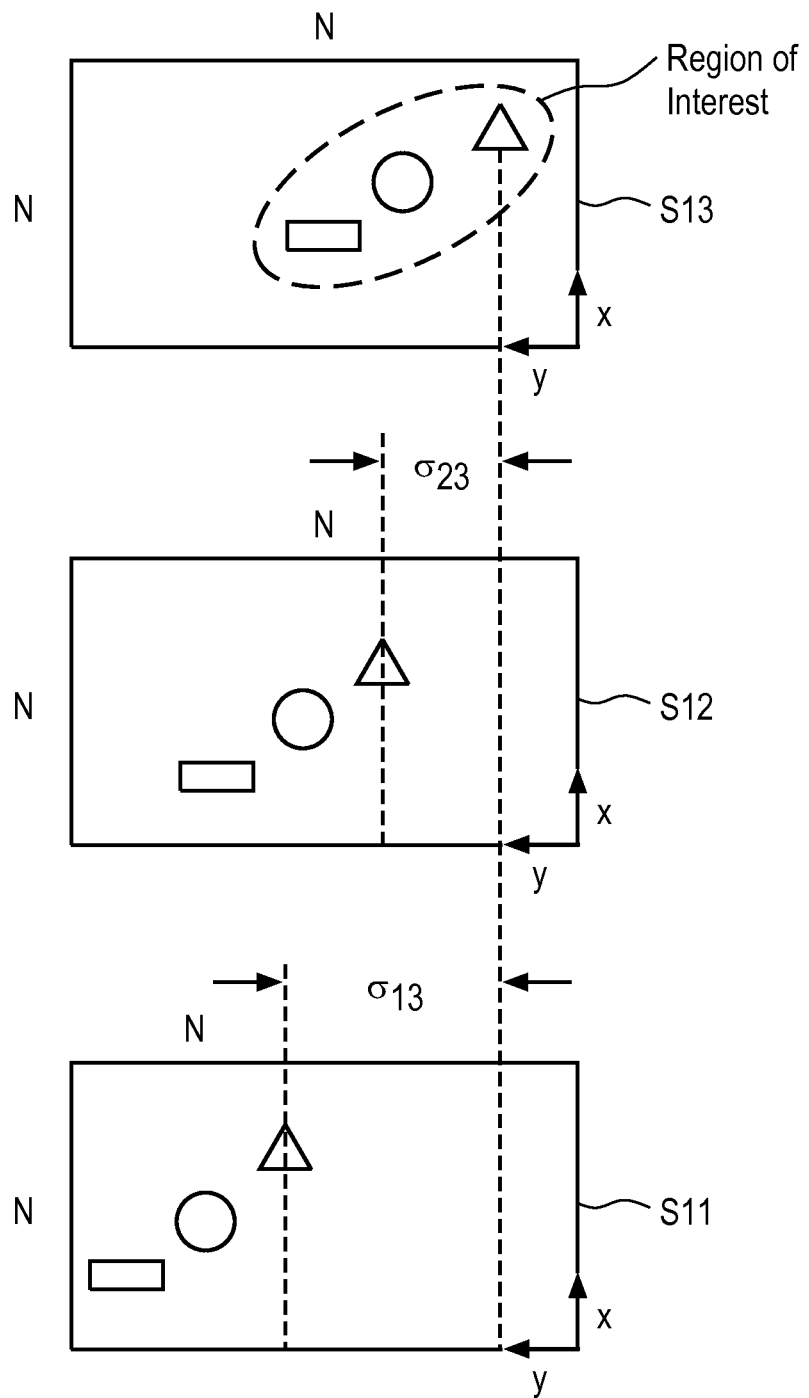
FIG. 14 is an illustrative drawing showing detail as to relative geometric offset of the projected images in sensors multiple sensors in accordance with some embodiments.

In accordance with module 402.3, a best match is determined between scene images within the region of interest so as to identify pixel locations in different sensors that are illuminated by projections of the same target. FIG. 14 is an illustrative drawing showing additional detail about relative geometric offset of the projected images in sensors $S_{11}$, $S_{12}$, and $S_{13}$ in accordance with some embodiments. In accordance with some embodiments, an image from sensor $S_{13}$ is considered to be reference image, and the projections of the objects in the selected ROI are offset to the right by an amount $\sigma_{23}$ pixels in sensor $S_{12}$ relative to their location in sensor $S_{13}$. Similarly, the projections of the objects in the selected ROI are offset to the right by an amount $\sigma_{13}$ pixels in sensor $S_{11}$ relative to their location in sensor $S_{13}$. It will be appreciated that since the FOV viewing axes of sensors $S_{12}$, $S_{11}$ each is offset to the right of the FOV viewing axis of sensor $S_{13}$ (such viewing axes being perpendicular to plane of the sensors), the projected images from ROI are offset to the left in the sensors $S_{13}$ and $S_{11}$ relative to sensor $S_{11}$.

Figure 15:
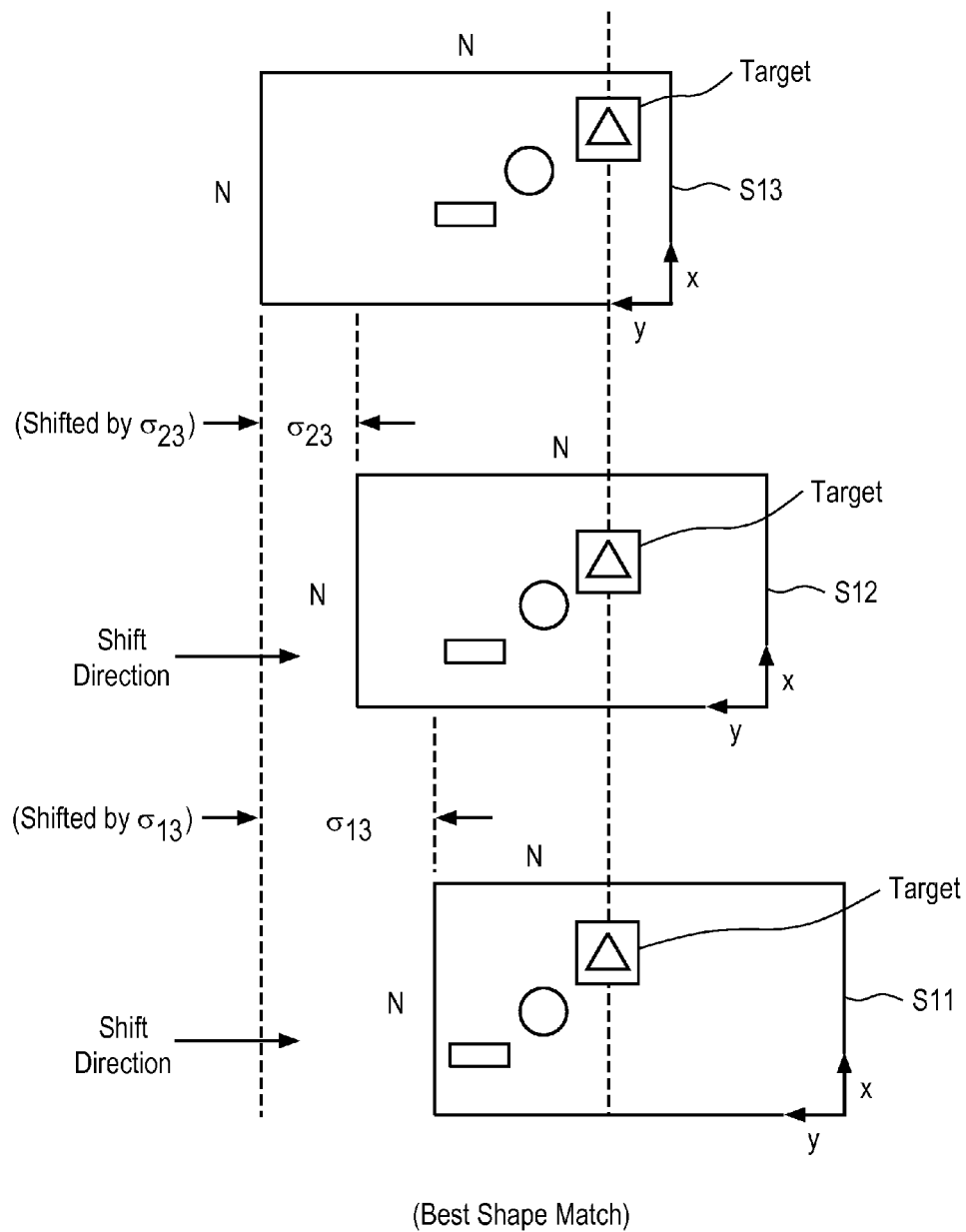
FIG. 15 is an illustrative drawing showing the projected images in certain example sensors within the region of interest (ROI) shifted to the right to align with the projected images in a designated reference sensor within the ROI in accordance with some embodiments.

FIG. 15 is an illustrative drawing showing the projected images in sensors $S_{11}$ and $S_{12}$ within the ROI shifted to the right to align with the projected images in sensor $S_{13}$ within the ROI in accordance with some embodiments. In the current example, sensor $S_{13}$ is designated to act as a reference sensor. It will be appreciated that other sensors can be chosen for use in determining alignment and geometric dimensions. Projections of the objects within the selected ROI are identified in the designated sensor, e.g., sensor $S_{13}$, and projections in the other sensors, e.g., in sensors $S_{11}$ and $S_{12}$, are shifted until they align with the projection in the designated sensor. In this manner, the corresponding projections of objects within the selected ROI can be identified within the other sensors, together with their offsets relative to the location of the projections in the designated sensor.

In particular, for example, the projections of the three example objects are shifted to the right by an amount $\sigma_{23}$ pixels in sensor $S_{12}$, and the projections of the three example objects are shifted to the right by an amount $\sigma_{13}$ pixels in sensor $S_{13}$. In this illustrative example, in order to simplify the explanation, it is assumed that the projections are offset in the y direction only and not in the x direction, although the same principles apply for x direction projection offsets as between sensors. Moreover, although this example shows a linear offsets, a person of ordinary skill in the art can apply other transformations such as rotation, for example, to align projections that have relative offsets in different sensors.

In accordance with some embodiments for example, two-dimensional (2D) cross-correlation techniques or principal component analysis (PCA), can be used to align the projections within the ROI in $S_{13}$ with the projections within the ROI in $S_{12}$ and to align the projections within the ROI in $S_{13}$ with the projections within the ROI in $S_{11}$. In general, the intent is to best match or align the images from sensors $S_{ij}$ with respect to the image from the sensor designated as reference. More specifically, the projected images within the ROI in $S_{12}$ are shifted and cross-correlated with the projected images within the ROI in $S_{13}$ until a highest correlation coefficient is achieved. Likewise, the projected images within the ROI in $S_{11}$ are shifted and cross-correlated with the projected images within the ROI in $S_{13}$ until a highest correlation coefficient is achieved. Thus, alignment of the projections of the ROI is used to identify the locations of the projections of the ROI in sensors $S_{11}$ and $S_{12}$ by determining the offset between the projection of the ROI in $S_{13}$ and the projection of the ROI in $S_{12}$ and by determining the offset between the projection of the ROI in $S_{13}$ and the projection of the ROI in $S_{11}$.

Example of Candidate Pixel Selection and Refinement

In accordance with module 402.4, candidate pixels are identified within different sensors, which according to the best match process, are illuminated by projections from the same target. Once the projections of objects within the ROI have been identified in each of the sensors $S_{11}$, $S_{12}$, and $S_{13}$, the physical (x, y, z) projections of individual target points within the ROI can be determined relative to the imager array. In accordance with some embodiments, for each of a multiplicity of target points within the ROI, one or more pixels within each of multiple sensors is identified that is illuminated by a projection from the target point. For each such target point, a physical (x, y, z) target point location is determined based at least in part upon the geometric relationships among pixels disposed in different sensors that are determined to be illuminated by projections from the target point.

It will be appreciated that a sequence of target points can be chosen automatically by systematically traversing the ROI (e.g., right to left with a certain step size and up to down with a step size), and a physical (x, y, z) target point location can be determined for each selected target point. Since $S_{11}$ and $S_{12}$ are best matched to $S_{13}$, the traversing is performed inside the shifted regions of interest. Selecting a target involves identifying a pixel in each of sensors $S_{11}$, $S_{12}$, and $S_{13}$ that is illuminated by a projection of the target. Thus, candidate pixels in each of $S_{11}$, $S_{12}$, and $S_{13}$ are identified as being the ones illuminated by a projection of the selected target point.

In other words, in order to select a target point T, a pixel is selected in each of the sensors $S_{11}$, $S_{12}$, and $S_{13}$ that is illuminated by a projection of the target point T. It will be appreciated that the (x, y, z) physical location of the target T is unknown at the moment of its selection. Moreover, it will be appreciated that inaccuracy of the above-described alignment process can result in inaccuracy in the determination of which pixels in each sensor are illuminated by the projection of a selected target T. Thus, as explained with reference to FIGS. 17, 18, and 19, a further determination is made as to the accuracy of the determination as to the pixels in each of $S_{11}$, $S_{12}$, and $S_{13}$ that are illuminated by the projection of a currently selected target T.

Figure 16:
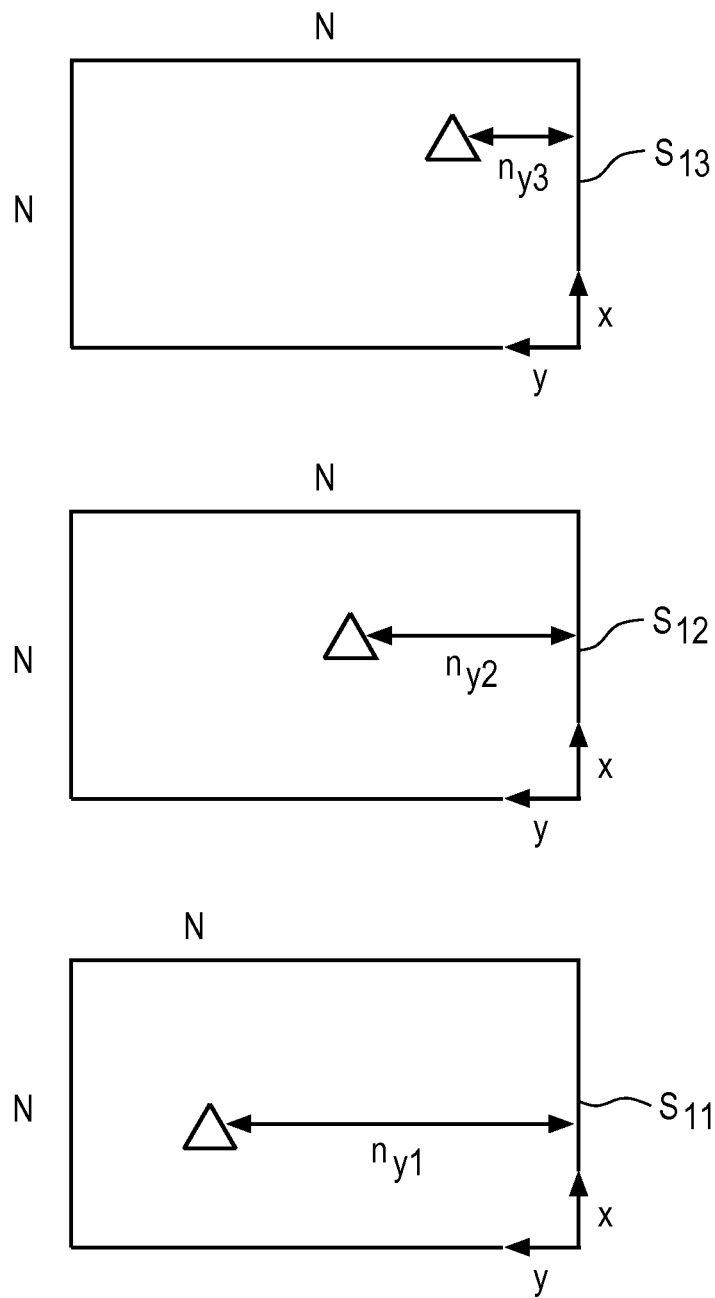
FIG. 16 is an illustrative drawing showing projections of a selected target point onto multiple sensors in accordance with some embodiments.

Continuing with the above example, assume that the triangular-shaped first object is the currently selected target point. FIG. 16 is an illustrative drawing showing projections of the selected triangle shaped target point onto sensors $S_{11}$, $S_{12}$, and $S_{13}$ in accordance with some embodiments. From these projections, the 2D pixel coordinates for target T are determined, [($Nx_{11}$, $Ny_{11}$), ($Nx_{12}$, $Ny_{12}$), ($Nx_{13}$, $Ny_{13}$)]. For simplification, FIG. 16 shows only the y-axis pixel coordinates. Using these 2D pixel coordinates, expressions (402.5-1) and (402.5-2) are applied and $\hat{y}_{12}$ and $\hat{y}_{13}$ computed as part of module 402.5. As part of module 402.6, the norm $|\hat{y}_{12}-\hat{y}_{13}|$ is computed and compared to the acceptable tolerance ε. Similarly, the x-axis pixel coordinates and location estimates are computed and compared against acceptable tolerances. If the condition of module 402.6 is met, then the process proceeds to module 403. Else, it returns to module 402.4 to further refine target candidates.

Figure 17:
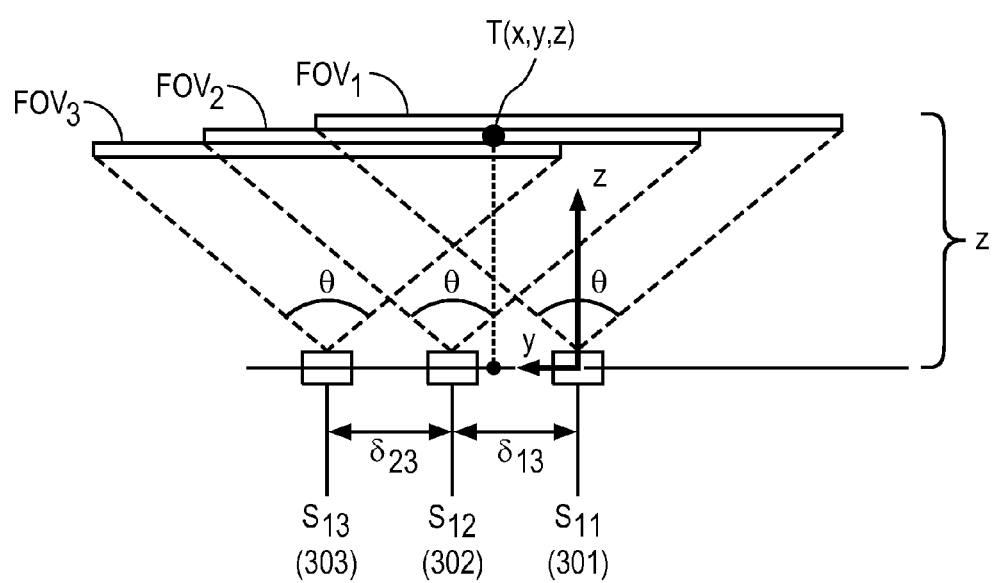
FIG. 17 is an illustrative drawing showing a portion of an imager array that includes the multiple sensors of FIG. 16 and the selected target point T disposed at location in physical space in accordance with some embodiments.

Referring to FIG. 17, there is shown a portion of an imager array that includes sensors $S_{11}$, $S_{12}$, and $S_{13}$ and the selected triangular-shaped first object target point T disposed at location (x, y, z) in physical space. Sensors within an imager array have a known spacing between them, $\delta_{ij}$. The physical position spacing between $S_{11}$ and $S_{12}$ is $\delta_{12}$, and the physical position spacing between $S_{12}$ and $S_{13}$ is $\delta_{23}$. In some embodiments the spacing between all sensors $S_{ij}$ is identical, equal to δ, a constructional specification. Sensors $S_{ij}$ also have a known field of view angle θ.

As explained above, in some embodiments, each sensor is constructed as a 2D imaging element with pixels arranged in a rectangular pattern of rows and columns. Alternatively, pixels can be arranged in a circular pattern, zigzagged pattern, scattered pattern, or an irregular pattern including sub-pixel offsets, for example. The angle and the pixel characteristics of these elements may be identical or, alternatively, may be different from sensor to sensor. However, these characteristics are assumed to be known. In order to simplify the explanation, it is assumed that the sensors are identical, although they may, however, be different.

For simplicity, let us assume that all sensors $S_{ij}$ have N×N pixels. At a distance z from sensor $S_{11}$, the N-pixel width of the sensor expands out to a y-dimension field of view of $S_{11}$ indicated by $FOV_1$. Likewise, at a distance z from sensor $S_{12}$, the y-dimension field of view of sensor $S_{12}$ is indicated by $FOV_2$. Also, at a distance z from sensor $S_{13}$, the y-dimension field of view of sensor $S_{13}$ is indicated by length $FOV_3$. The lengths $FOV_1$, $FOV_2$, and $FOV_3$ overlap each other, signifying that sensors $S_{11}$, $S_{12}$, and $S_{13}$ achieve a 3-way sampling diversity of target T physically located at some (unknown) distance z. Of course, if the sensors are identically built, as assumed in this example, length $FOV_1$, $FOV_2$, and $FOV_3$ will be identical as well. It will be appreciated that the three lengths $FOV_1$, $FOV_2$, and $FOV_3$ all have the same magnitude and are coplanar in that they are at the same (unknown) z-distance from the imager array, although for the purpose of illustration they are portrayed as if they were stacked adjacent to each other.

Figure 18:
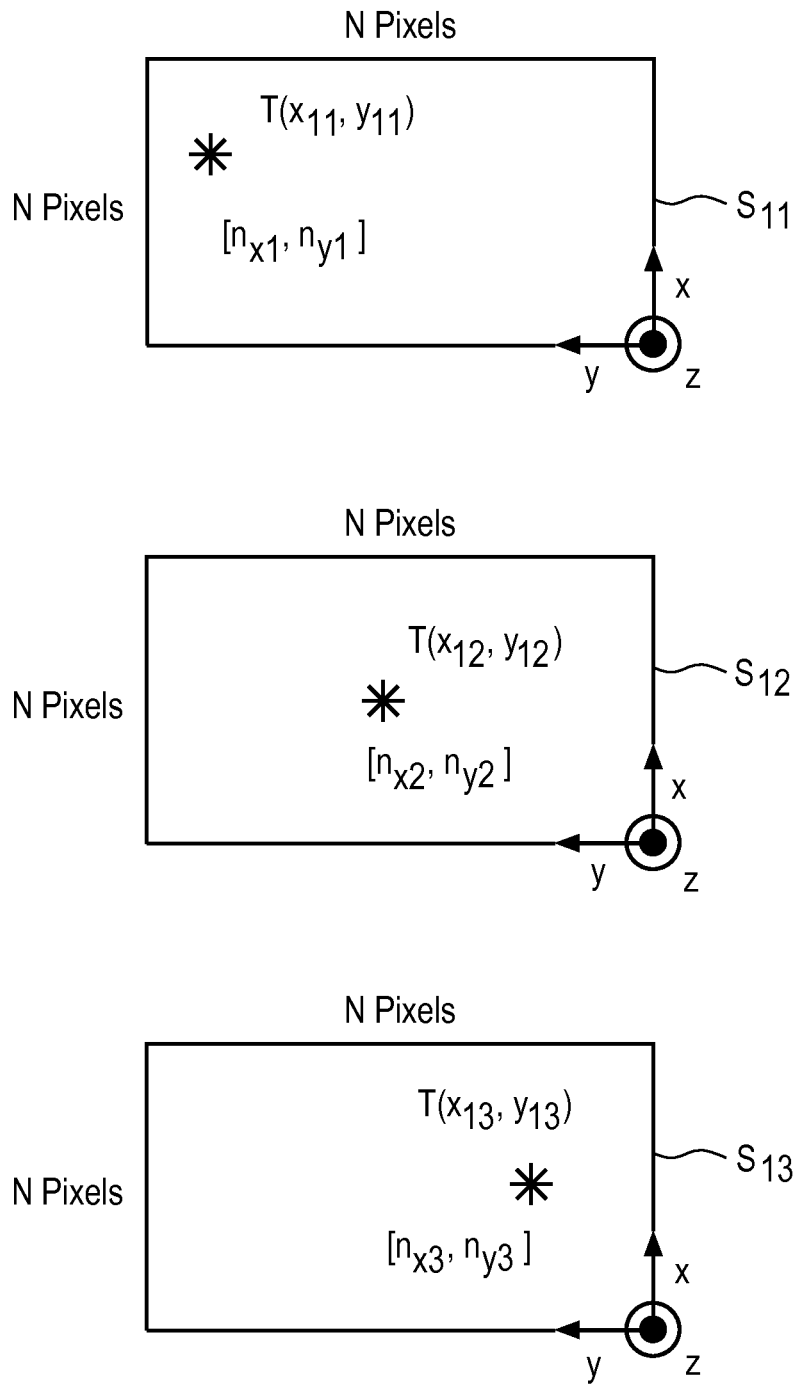
FIG. 18 is an illustrative elevation view of the projection of the currently selected target point T onto the multiple image sensors of FIG. 16 in accordance with some embodiments.

Referring to FIG. 18, there is shown an illustrative elevation view of the projection of the currently selected target point T onto the image sensors $S_{11}$, $S_{12}$, and $S_{13}$. For the sake of simplicity, it is assumed that the sensors include geometrically rectangular pixel arrays of size N×N pixels. It is also assumed that the x coordinates of the target T projections are all equal. In other words, it is assumed that for the projections of target T onto $S_{11}$, $S_{12}$, and $S_{13}$, $n_{x1}=n_{x2}=n_{x3}$. To simplify the explanation, it is also assumed that the geometric field of view angle θ is the same horizontally as it is vertically, $\theta_x=\theta y$. A person of skill in the art would know how to modify the process presented below so that to compute the x, y, and z physical coordinates of target T if any of the above assumptions would change.

Figure 19:
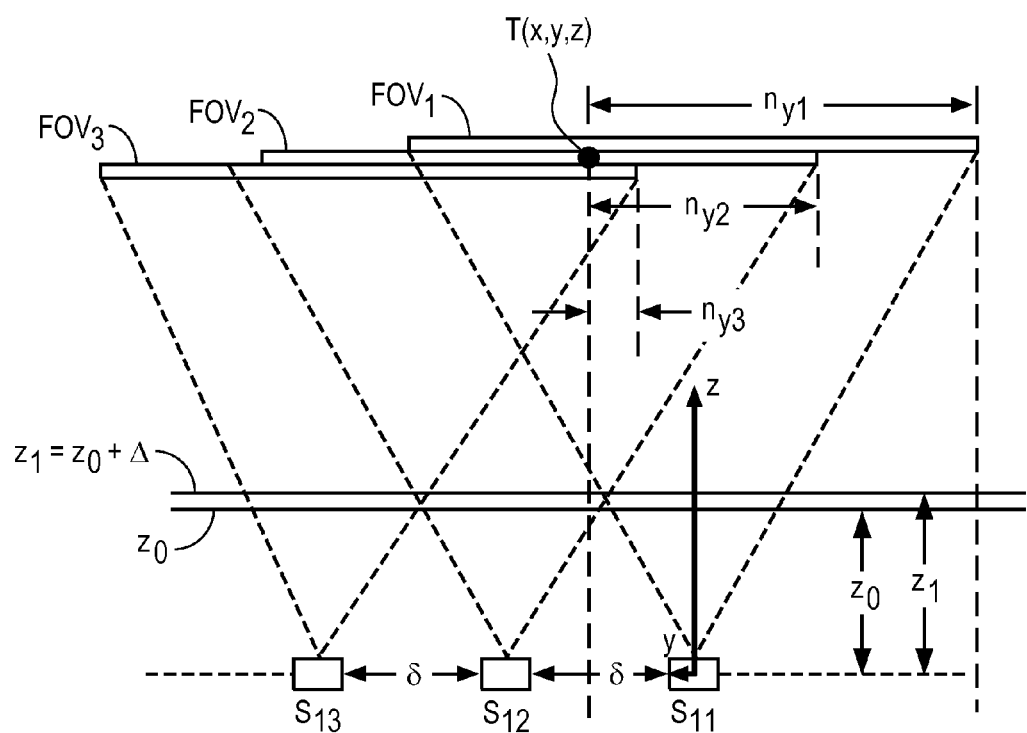
FIG. 19 is an illustrative drawing showing the disposition of a currently selected target relative to the multiple sensors as described above with reference to FIG. 17 and also showing y-direction pixel offsets for the candidate pixel in each of the sensors in accordance with some embodiments.

An image of the target T is projected to a physical point within sensor $S_{11}$ at geometric coordinates ($n_{x1}$, $n_{y1}$), in the plane of the image sensor $S_{11}$. More specifically, the projection of target point T onto sensor $S_{11}$ is located $n_{y1}$ pixels along the y axis, and $n_{x1}$ pixel along the x axis, taken from the origin. An image of the target T is projected to a physical point within sensor $S_{12}$ at geometric coordinates ($n_{x2}$, $n_{y2}$) in the plane of the image sensor $S_{12}$. An image of the target T is projected to a physical point within sensor $S_{13}$ at geometric coordinates ($n_{x3}$, $n_{y3}$) in the plane of the image sensor $S_{13}$. It will be appreciated that pixel locations ($n_{xi}$, $n_{yi}$) within each sensor are determined relative to origin (0, 0) reference coordinates provided for the sensor. As shown in FIG. 17 or FIG. 19, a global system of coordinates (x, y, z) is defined and used to reference the target. For example, the origin of such system of coordinates may be placed, without limitations, at the geometrical center of sensor $S_{11}$.

Referring to both FIG. 16 and FIG. 18, it can be seen that the y pixel distance of the projection of the target is different in each sensor. The projection of a currently selected target T is disposed $n_{y1}$ pixels to the left of the origin in $S_{11}$. The projection of the selected target T is disposed $n_{y2}$ pixels to the left of the origin in $S_{12}$. The projection of the selected target T is disposed $n_{y3}$ pixels to the left of the origin in $S_{13}$. As mentioned above, to simplify the explanation, it is assumed that the projection of the target falls at the same x pixel distance from the origin in all three sensors.

Referring to FIG. 19, there is shown the disposition of the currently selected target T relative to sensors $S_{11}$, $S_{12}$ and $S_{13}$ as described above with reference to FIG. 17 and also showing y-direction pixel offsets for the candidate pixel in each of the sensors. It will be understood that the drawings of FIG. 19 present physical structures and an analytical framework for determining the (x, y, z) physical coordinates of the selected target point T. At an (unknown) distance z from the imager array plane, the y-direction field of view for each sensor extends over a length marked as $FOV_i$. This length, $FOV_i$, corresponds to the maximum pixel width of the sensor, which is N pixels, in some embodiments. Given that the working assumption was that the sensor has a field of view that is symmetric in the x and y directions, the length would also be $FOV_1$ vertically, along the x axis.

Recall that the candidate pixel selections are made based at least in part upon a correlation process that can have a level of uncertainty than can result in inaccuracy in determination of the physical location of the selected target. Thus, a further check of the accuracy of the target projection candidate selections, in accordance with some embodiments, is made as follows.

Example of Determining Target's Physical (x, y) Location and Checking Accuracy of Target Projection Candidate Selection In accordance with module 402.5, two or more two-dimensional ($N_x$, $N_y$) coordinate values are computed for the selected target to determine whether the candidate pixels actually are illuminated by a projection from the same target. Based on the assumptions discussed above and placing the origin of the 3D system of coordinates at the center of sensor $S_{11}$, the imager array and currently selected target T in the example in FIG. 19 have the following relationships:

$$z = \frac{N \cdot \delta}{2 \cdot (n_{y1} - n_{y2}) \cdot \tan\left(\frac{\theta}{2}\right)} \qquad (1)$$

$$y = \frac{2n_{y1} - N}{2(n_{y1} - n_{y2})} \cdot \delta \qquad (2)$$

$$x = \left(\frac{2n_{x1}}{N} - 1\right) \cdot z \cdot \tan\left(\frac{\theta}{2}\right) \qquad (3)$$

Where:

N is the pixel dimension of the imaging sensors;

$n_{x1}$ is the position of a target point T expressed in number of pixels from the origin of the $S_{11}$ plane in the x direction;

$n_{y1}$ is the position of the target point T expressed in number of pixels from the origin of the $S_{11}$ plane in the y direction;

$n_{y2}$ is the position of the target point T expressed in number of pixels from the origin of the $S_{12}$ plane in the y direction; and $n_{y2}$ is the position of the target point T expressed in number of pixels from the origin of the $S_{12}$ plane in the y direction;

θ is the angle of the field of view.

Moreover, if performing the same math using sensors $S_{11}$ and $S_{13}$ and given that the separation between $S_{11}$ and $S_{13}$ is 2δ, we obtain:

$$z = \frac{2 \cdot N \cdot \delta}{2 \cdot (n_{y1} - n_{y3}) \cdot \tan\left(\frac{\theta}{2}\right)} \qquad (4)$$

$$y = \frac{2n_{y1} - N}{2(n_{y1} - n_{y3})} \cdot 2\delta \qquad (5)$$

$$x = \left(\frac{2n_{x3}}{N} - 1\right) \cdot z \cdot \tan\left(\frac{\theta}{2}\right) + 2\delta \qquad (6)$$

Where:

$n_{x3}$ is the position of a target point T expressed in number of pixels from the origin of the $S_{13}$ plane in the x direction; and $n_{y3}$ is the position of the target point T expressed in number of pixels from the origin of the $S_{13}$ plane in the y direction.

Thus, determination of the physical x coordinate of the selected target T can be determined based upon expressions (3) or (6). A determination of the physical y coordinate of the selected target T can be determined based upon expressions (2) or (5). A determination of the physical z coordinate of the selected target T can be determined based upon equations (1) or (4).

More generally, in accordance with module 402.6, a determination is made as to whether the computed 2D coordinate values indicate that the candidate pixels are illuminated by a projection from the same target. It will be appreciated that a more reliable determination of the physical (x, y, z) coordinates of the target T can be obtained through the use of two formulations for each coordinate. For example, the y coordinate for the target T can be determined using both formulations (2) and (5). If the resulting y coordinate values computed using the two formulations differ by more than some acceptable tolerance value, $\varepsilon_y$, then a determination can be made that the matching process failed to resolve the offset between projections in the different sensors with sufficient accuracy, and as result that the candidate pixels do not correspond in that they do not receive projections from the same target T. In the event of a failure of the y computations to match, another iteration of the matching process may be performed in an effort to make an improved selection of candidate pixels within the sensors that each corresponds to a selected target T. It will be appreciated that the computed y values are unlikely to be equal since the different perspective projections onto different sensors can differ due to parallax effects, for example. Therefore, an acceptable tolerance value is prescribed according to the intended application. For surgical imaging applications, an ε of 0.1-0.3 mm typically offers an acceptable Q3D accuracy. A person of skill in the art may define different acceptable tolerance levels without departing from the spirit of this invention.

Given the assumed sensor symmetry around the x and y axes, persons skilled in the art will appreciate that the same kind of determination can be made for the x coordinates of the target T using formulations similar to those in (2) and (5), but using $n_{xi}$ instead of $n_{yi}$. Formulations (3) and (6) cannot be used part of 402.5 and 402.6 because they require knowledge of the z coordinate. However, the essence of modules 402.5 and 402.6 is to determine the correct target projections on the planes of sensors $S_{11}$, $S_{12}$ and $S_{13}$. For this purpose formulations (2) and (5), adjusted for x and y axes, are sufficient. The complete set of coordinates (x, y, z) is computed part of modules 403 and 404, as described below.

Example of Determining Target's Physical z Location

As illustrated in FIG. 19, in accordance with modules 403 and 404, an initial estimate for the z coordinate, $z_0$, is used to initiate the computation process. This initial value is defined automatically, according to the medical application. The medical application defines the intended world view to be visualized. The initial value $z_0$ starts at the edge of the field of view closest to the endoscope. Referring to FIG. 8, for a Q3D application involving surgical endoscopy, $z_0$ can be 1-5 mm off the distal end 208 of the Q3D endoscope 202, for example. Such initial estimate generally is sufficient for this application as it is unlikely to have any tissues or surgical instruments reside in such close proximity to the Q3D endoscope. Next, value $z_0$ is plugged into formulations (3) and (6). Given that the x coordinate of the target is unique, if $z_0$ were the true and correct z coordinate of the target then formulations (3) and (6) would yield identical values, or approximately equal, within an acceptable level of tolerance, $\varepsilon_x$.

$$|x_{(3)} - x_{(6)}| < \varepsilon_x \qquad (7)$$

If (3) and (6) are outside an acceptable tolerance $\varepsilon_x$, then the iteration continues and a new estimate for z is tried, $z_1$. In accordance with some embodiments, the new estimate is defined automatically. For example, $z_1 = z_0 + \Delta$, where $\Delta$ is the size of the iteration step. In general, at $k^{th}$ iteration $z_k = z_{k-1} + \Delta$. The iterative process stops when condition (7) is met. A smaller $\Delta$ yields increased accuracy in determining the correct target coordinates, but it would also require more computational time to complete the process, hence an increased latency. An increased latency may result in delays between surgical instrument movement and its visualization by the operating surgeon. In other words, the surgeon may perceive the system as lagging behind commands. For a surgical viewing space of 20-30 cm of depth, a $\Delta$ of 0.1-0.3 mm may be sufficient. Of course, a person skilled in the art would know to balance the size of Δ against the computational required to complete the iterative process.

The above explanation has been simplified for presentation reasons and, therefore, it included only three sensors, $S_{11}$, $S_{12}$, and $S_{13}$. In general, more sensors can be used to increase the accuracy of Q3D coordinate computations but also to reduce the overall number of iterations. For example, if more than three sensors are used, preferably an array of 3×3 sensors, then methods such as the steepest gradient may be employed to trend the direction of estimation errors made by modules 402.5 and 403. The iterative step size and direction can then be adjusted to match the progression towards the local extreme of the 3D error gradient surface.

Guiding Endoscopic Surgery with Q3D Information

Figure 20:
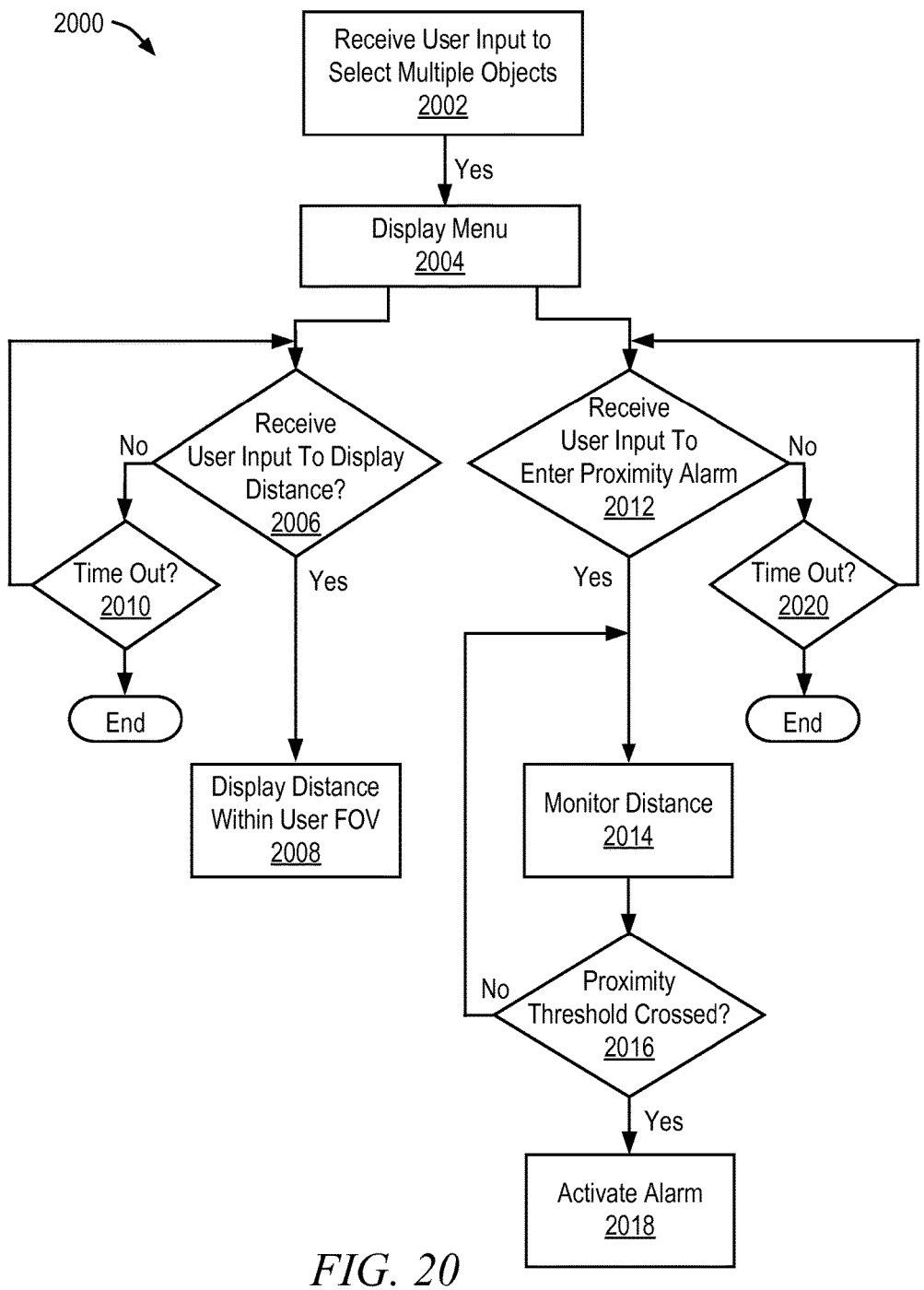
FIG. 20 is an illustrative flow diagram representing a first process to use Q3D information during a surgical procedure in accordance with some embodiments.

FIG. 20 is an illustrative flow diagram representing a first process 2000 to use Q3D information during a surgical procedure in accordance with some embodiments. Computer program code configures the computer 151 to perform the process 2000. Module 2002 configures the computer to receive user input to select at least two objects within a surgeon's field of view when looking into the viewer 312. Module 2004 configures the computer to display a menu on a computer console in response to receipt of a user selection. Decision module 2006 configures the computer to determine whether user input to the menu is received to display a distance. In response to a determination that user input is received to display a distance, module 2008 configures the computer to display a numerical distance within the video image in the surgeon's field of view. Decision module 2010 configures the computer to wait for a prescribed time interval for receipt of user input to select distance display and to end operation of decision module 2006 in response to no receipt of user input within a "time out" interval.

Decision module 2012 configures the computer to determine whether user input to the menu is received to enter a proximity alarm limit. In response to a determination that user input is received to enter a proximity threshold, module 2014 configures the computer to use Q3D information to monitor proximity between two or more objects within the surgeon's field of view. Decision module 2016 determines whether the proximity threshold has been crossed. In response to a determination that the proximity threshold has been crossed, module 2018 configures the computer to activate an alarm. The alarm may include a sound, a visual queue such as a blinking light, locking of instrument movement to avoid collision, or other haptic feedback. In response to a determination that the proximity threshold has not been crossed, control flows back to monitoring module 2014. Decision module 2020 configures the computer to wait for the prescribed time interval for receipt of user input to enter the proximity threshold and to end operation of decision module 2012 in response to no receipt of user input within the "time out" interval.

Figure 21:
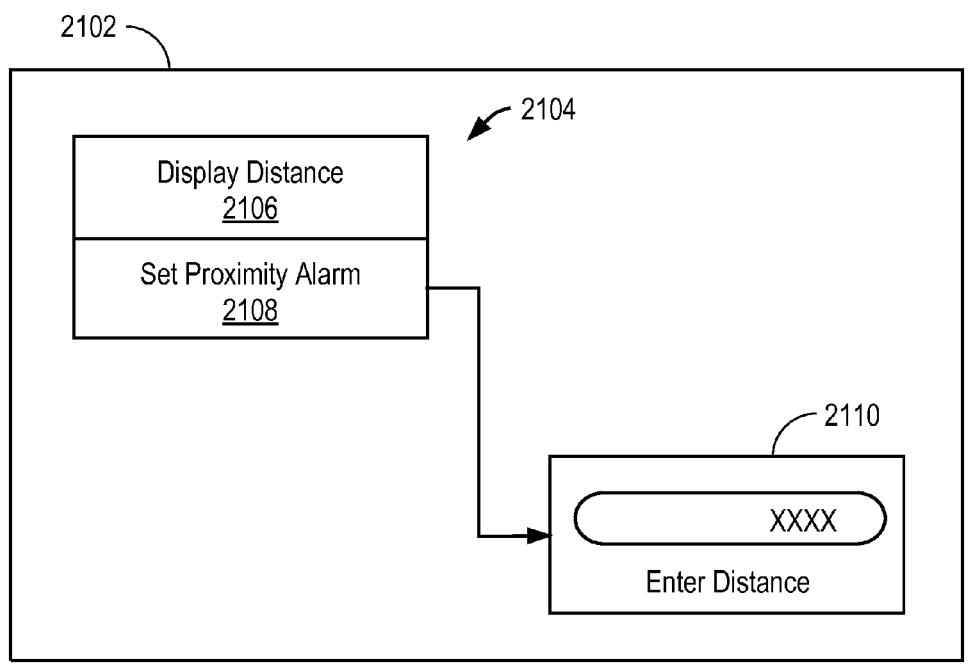
FIG. 21 is an illustrative drawing showing menu selections displayed on a display screen in accordance with the process of FIG. 20 in accordance with some embodiments.

FIG. 21 is an illustrative drawing showing menu selections displayed on a display screen 2102 in accordance with the process of FIG. 20 in accordance with some embodiments. The display screen 2102 includes a viewing monitor associated with the computer 151. Alternatively, the display screen 2102 may include a region of the viewing elements 401R, 401L of the viewer 312. In response to user input, module 2004 causes the display of a menu 2104 that includes a first menu item "Display Distance" 2106 and a second menu item "Set Proximity Alarm" 2108. In response to user input to select the "Display Distance" menu item 2106, module 2008 causes a display of Q3D distance between two or more objects. Referring again to FIG. 4, there is shown a display of a Q3D distance "d_Instr_Trgt" between an instrument 400 and target displayed using module 2008. In response to user input to select the "Set Proximity Alarm" menu item 2108, an "Enter Distance" UI input 2110 is displayed that includes a field in which a user can enter a proximity distance threshold value, e.g., one cm. In an alternative embodiment (not shown), a default proximity threshold may be set in advance for all instruments, and a user may change the proximity threshold using the menu of FIG. 21, for example. In the alternative embodiment, a user can choose to elect the default threshold value rather than enter a threshold value. In some embodiments, a user can select both to display the distance and set a proximity alert.

Figure 22A:
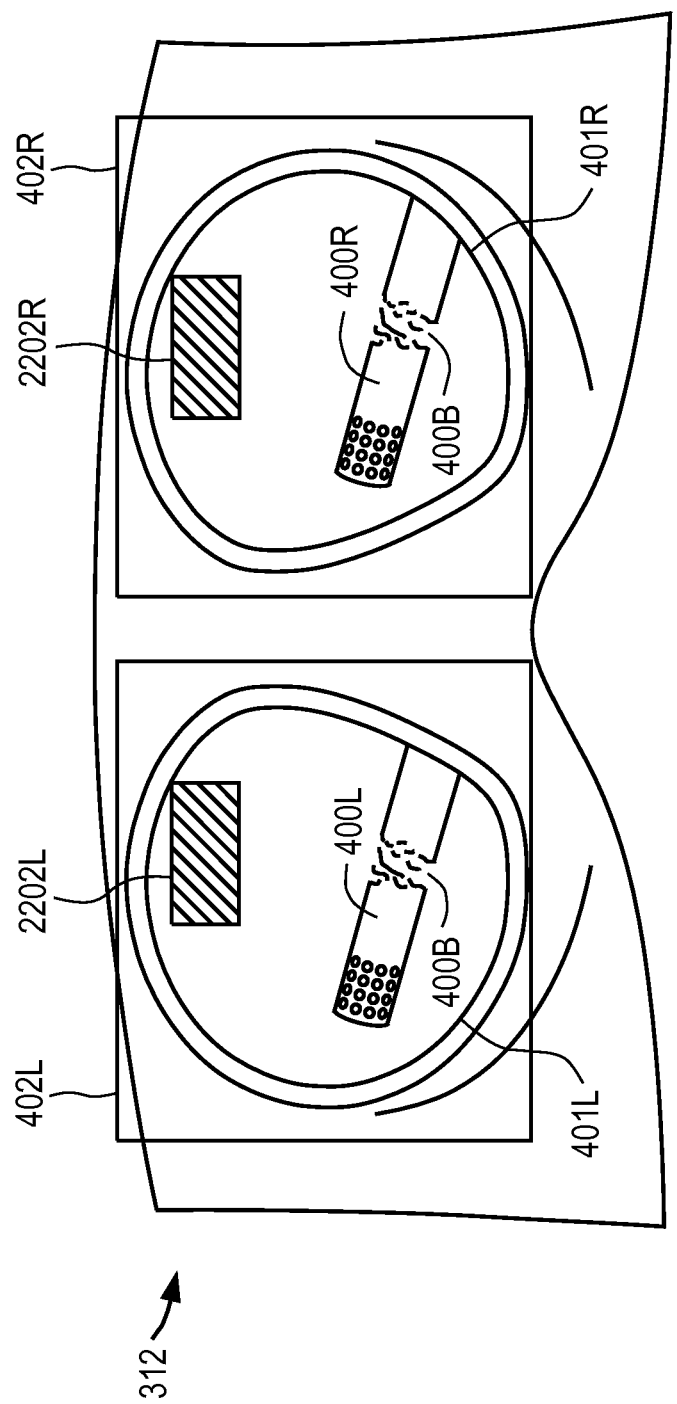
FIGS. 22A-22B are illustrative drawings representing certain details of receiving user input in accordance with the process of FIG. 20 in accordance with some embodiments.
Figure 22B:
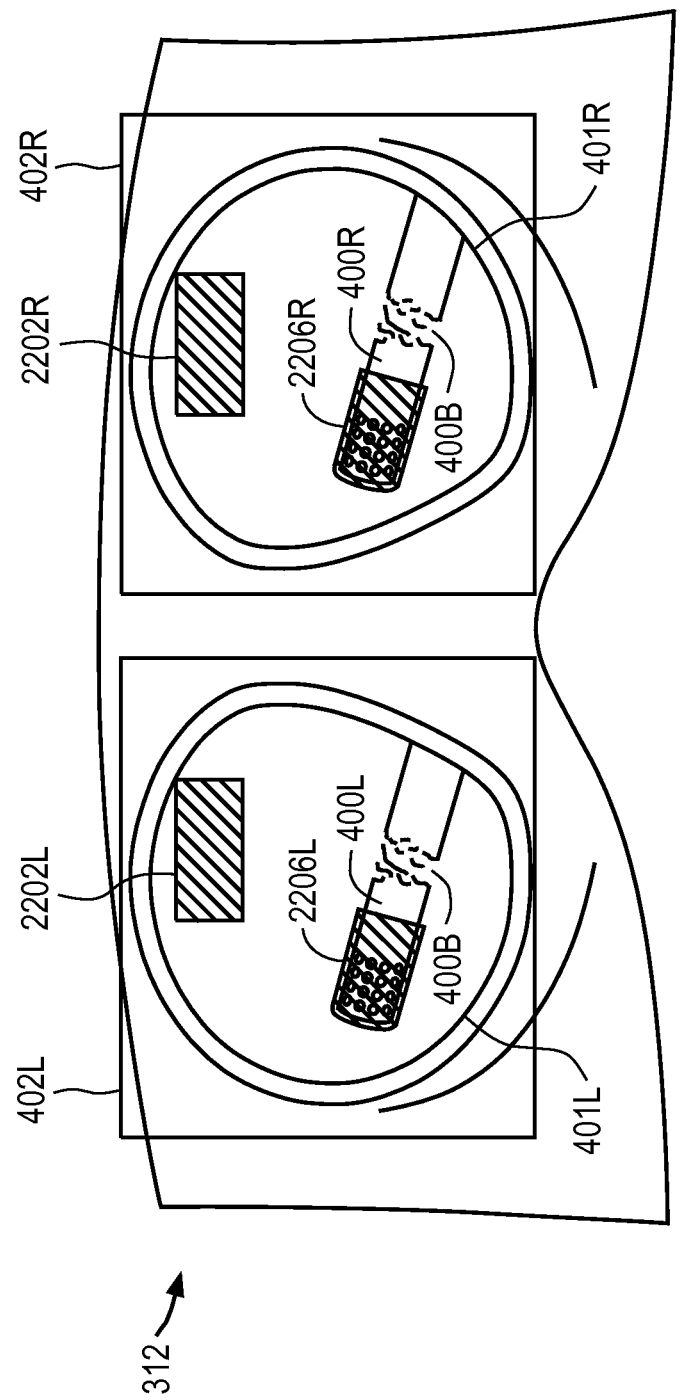

FIGS. 22A-22B are illustrative drawings representing certain details of receiving user input in accordance with the process of FIG. 20 in accordance with some embodiments. FIG. 22A shows example first highlighting areas 2202L, 2202R of a target 410L, 410R, such as body tissue, which can be created using video marker tool, such as telestration, or using the surgeon console manipulating control input devices 160 of FIG. 4. FIG. 22B shows example second highlighting areas 2206L, 2206R of an instrument tip 400L, 400R, which can be created using the video marker tool. In operation in accordance with some embodiments, a user creates the first highlighting areas 2202L, 2202R. Next, the user creates second highlighting areas 2206L, 2206R of the instrument tip 400L, 400R using video marker tool. It will be understood that the order in which items are highlighted is unimportant. The user then actuates a selector (not shown) (e.g., press the ENTER key) to enter the selection. Module 2002 interprets the received user input as selection of the target image 410L, 410R and the instrument image 400L, 400R.

Figure 23:
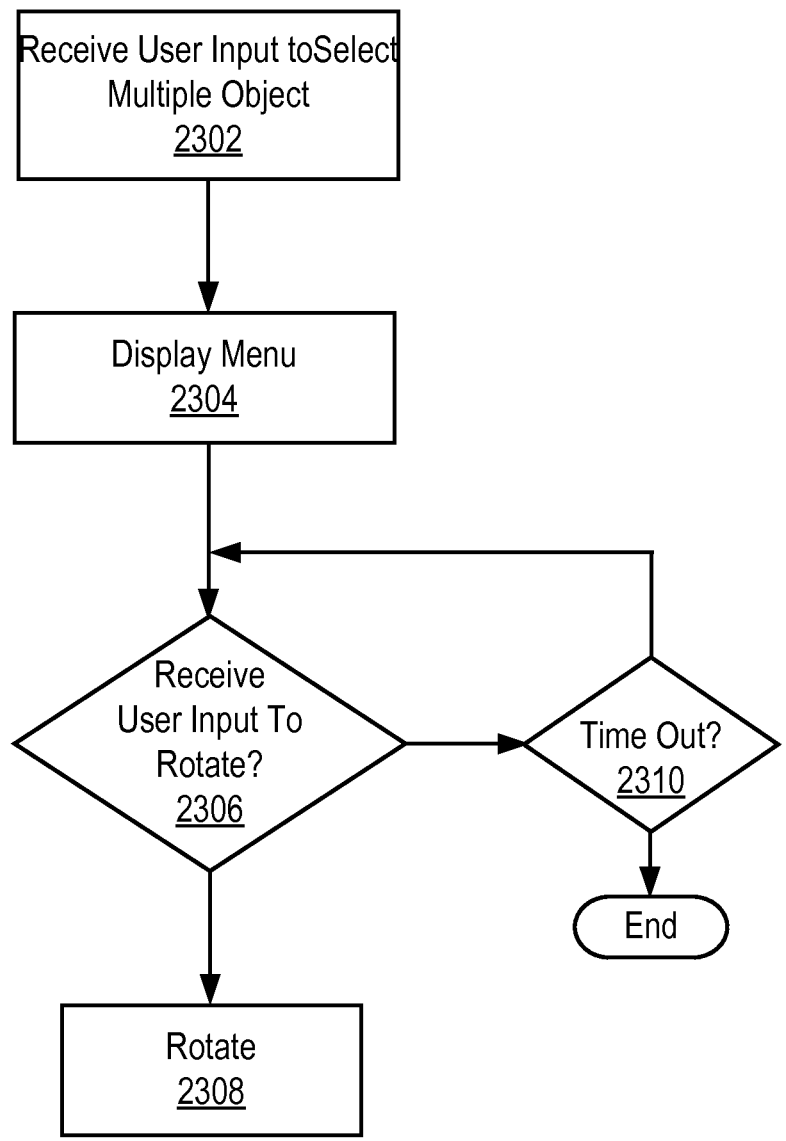
FIG. 23 is an illustrative flow diagram representing a second process to use Q3D information during a surgical procedure in accordance with some embodiments.

FIG. 23 is an illustrative flow diagram representing a second process 2300 to use Q3D information during a surgical procedure in accordance with some embodiments. Computer program code configures the computer 151 to perform the process 2300. Module 2302 configures the computer to receive user input to select an object within a surgeon's field of view when looking in to the viewer 312. For example, referring again to FIG. 22A, user input is shown received to create the second highlighting areas 2206L, 2206R of the instrument tip 400L, 400R using the video marker tool. User input (not shown) is received to actuate a selector (not shown) (e.g., press the ENTER key) to enter the selection of the image of the instrument tip 400L, 400R.

Returning once again to FIG. 23, in response to receipt of a user selection, module 2304 configures the computer to display a menu on a computer console. Decision module 2306 configures the computer to determine whether user input to the menu is received to rotate an image of a selected object. In response to a determination that user input is received to rotate an image, module 2308 configures the computer to display rotate the image to show a different three-dimensional perspective of the object. Decision module 2310 configures the computer to wait for a prescribed time interval for receipt of user input to rotate an image and to end operation of decision module 2306 in response to no receipt of user input within a "time out" interval.

Figure 24:
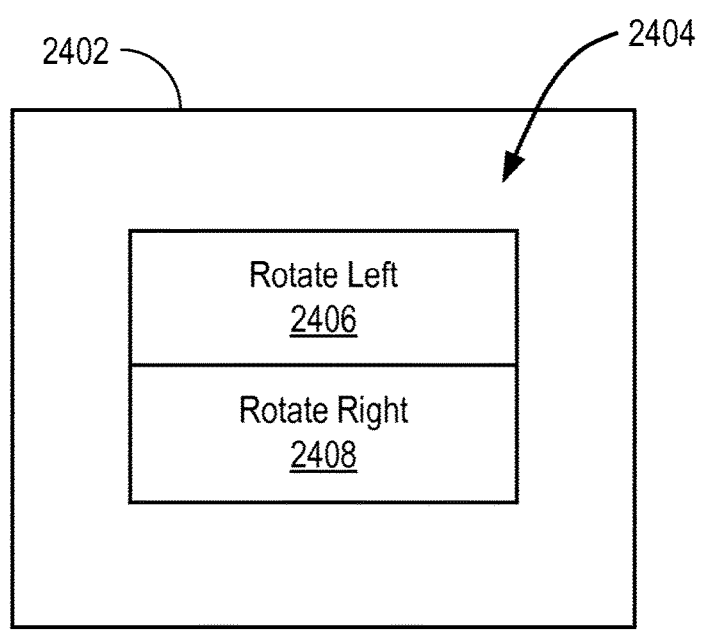
FIG. 24 is an illustrative drawing showing menu selections displayed on a display screen in accordance with the process of FIG. 23 in accordance with some embodiments.

FIG. 24 is an illustrative drawing showing menu selections displayed on a display screen 2402 in accordance with the process of FIG. 23 in accordance with some embodiments. The display screen 2402 includes a viewing monitor associated with the computer 151. Alternatively, the display screen 2402 may include a region of the viewing elements 401R, 401L of the viewer 312. In response to received user input, module 2304 causes the display of a menu 2404 that includes a third menu item "Rotate Left" 2406 and a fourth menu item "Rotate Right" 2408. In response to user input to select one or the other of the third or fourth menu items

2406, 2408, module 2308 uses the causes a rotation of the 3D model created and stored pursuant to module 407 of FIG. 9. It will be appreciated that the amount of rotation may be limited to a few degrees, less than 30 degrees for example, since the sensor imager array 210 has a limited overall field of view.

Q3D Replacement Models & Model Optimization Via Jitter

A surgical procedure may involve removal of damaged or diseased bone tissue and replacement with a prosthetic implant. A portion of the bone is damaged through disease or injury, for example. FIG. 25A is an illustrative drawing showing an example top view of an anatomical structure before a surgical procedure, in accordance with some embodiments. The anatomical structure may be a portion of bone such as a knee, hip, elbow, shoulder, spine, skull, ankle, wrist, foot, palm, etc. bone portion. A portion of the bone is damaged through disease or injury, for example. FIG. 25B is a side view cross-section view generally along dashed cutting plane lines A-A from perspective 1-1 in FIG. 25A showing contours of the example damaged portion in greater detail.

FIG. 26A is an illustrative drawing showing an example top view of an anatomical structure after the surgical procedure removing damaged or diseased bone tissue and leaving behind a void bounded by remaining healthy tissue in accordance with some embodiments. Referring to FIG. 5 for example, it is assumed that a physician may use a teleoperated system 100 to perform a medical procedure involving removal of damaged bone tissue and its replacement with a prosthetic structure, such as repair, partial or total replacement of knee, hip, shoulder, spine, skull, ankle, wrist, foot or palm bone, using a surgical instrument 101A or 101B to remove the damaged portion from the anatomical structure, leaving intact the healthy or uninjured part that defines a void, empty space or gap where the damaged portion had been located previously. Alternatively, a manual instrument may be used. FIG. 26B is a side view cross-section view generally along dashed lines A-A from perspective 1-1 in FIG. 26A showing contours of the example healthy or uninjured region after removal of the diseased or damaged bone tissue.

In accordance with some embodiments, contour and size of a replacement structure that fits snugly within a void left behind by bone tissue removal are determined based upon a Q3D model of contours of the healthy bone tissue, also referred to herein as the "remainder" bone tissue, remaining after removal of the damaged or injured bone tissue. Before removal of the damaged or diseased bone tissue, a Q3D model is produced based upon image information captured from the anatomical structure that represents contour of an external surface of the bone tissue, including the damaged or diseased bone tissue, before removal. After removal of the damaged or diseased bone tissue which has not yet been removed, another Q3D model is produced based upon image information captured from the anatomical structure that represents contour of an external surface of the bone tissue, including the remainder structure, after removal. An endoscope 101C associated with a Q3D sensor is moved to a position in which a Q3D sensor can image externally visible contours of the remaining bone tissue surrounding the void from which damaged or diseased tissue has been removed. In accordance with some embodiments, and as described above with reference to FIGS. 6-19, the Q3D sensor is disposed to capture a Q3D image of the remainder bone tissue surrounding the void region, and a Q3D model of the remainder bone tissue is produced. A prosthetic implant is produced based upon the Q3D model of the "remainder" bone tissue. The prosthetic implant is placed within the void defined by the remainder bone tissue to act as a replacement for the removed bone tissue.

Figure 27A:
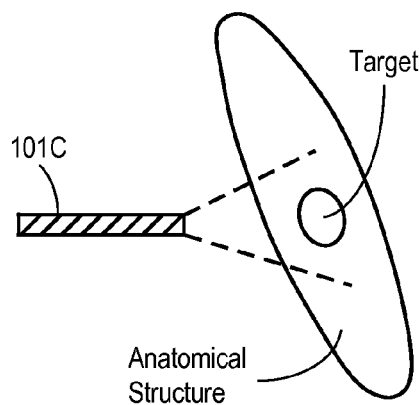
FIGS. 27A-27C are illustrative drawings showing an endoscope in three different example "jitter" positions to capture three different image viewpoints of the target region in accordance with some embodiments.
Figure 27B:
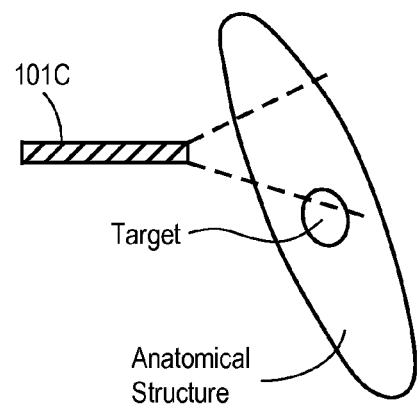
Figure 27C:
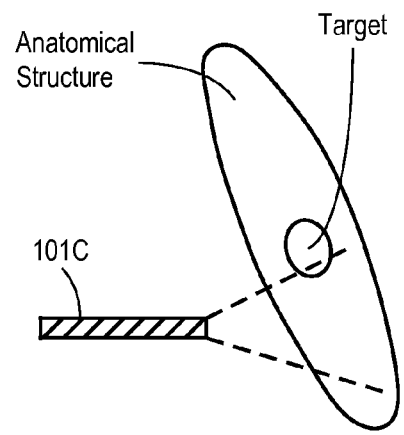

During Q3D image capture in accordance with some embodiments, a viewing perspective of the endoscope 101C used to capture a Q3D image is "jittered"—that is, adjusted or moved between several (two or more) real viewpoints from which it can capture Q3D image information from a target region, such as a damaged tissue before tissue removal or remainder tissue after tissue removal, to be imaged, in order to enhance the resolution and accuracy of a Q3D model produced based upon the captured Q3D image information. FIGS. 27A-27C are illustrative drawings showing an endoscope 101C in three different example "jitter" positions to capture three different image viewpoints of the target region in accordance with some embodiments. To achieve the different jitter positions, the endoscope 101C is moved by known amounts so that the different jitter positions are known relative to each other. The different endoscope positions differ by small distances, for example smaller than 5 mm (e.g., fractions of a sensor pixel width, fractions of a sensor width). These small distances ensure sufficient redundancy in 3D images acquired by endoscope 101C from the different positions. Superresolution image reconstruction is then applied to the captured images to produce an image having a resolution that is enhanced in comparison to each of the captured images.

The controlled jittering of the Q3D endoscope 101C increases the accuracy of the computation of (x, y, z) coordinates for the points within the space volume corresponding to a target region of interest, such as remainder bone tissue. The accuracy is increased because additional data, with sufficient redundancy, from additionally and slightly changed viewing angles, are provided to the processes described above with reference to FIGS. 9-19. Particularly, the controlled jittering helps process of FIG. 9 to find more accurately the target at steps 402-404. Given the increased redundancy in the additional data, this is achieved by improving the accuracy of finding the 'best matches' described at steps 402.3-402.5 in FIG. 10. The fact that the jittering of the Q3D endoscope 101C is controlled offers views of a target scene of interest from slightly different angles. This is equivalent to a "virtual" increase of the distance between sensors $S_{ij}$. The controlled jittering can be achieved by the hardware that controls the robotic arm 158C that supports the Q3D endoscope 101C, in reference to FIG. 5. Alternatively, the jittering may be electronically introduced if Q3D endoscope 101C is built using lens with electronically adjustable optical properties. For example, according to Hassanfiroozi et al., "Liquid crystal lens array for a 3D endoscope", Proceedings SPIE 9117, May 9, 2014, liquid crystal lens arrays can be employed. Such lenses, if used in conjunction with Q3D endoscope 101C, can have their optical properties adjusted by modulation of control voltage signal. Optical jitter can thus be introduced by modifying the control voltage based in a known pattern. For example, the optical axis of such lenses could be adjusted. This action has the equivalent effect of mechanically jittering the orientation of 101C. Either mechanical jittering, through of motion of robotic arm 158C, or electronic jittering, through modulation of a control voltage of liquid crystal lenses, can have the same result of increased accuracy in computing the (x, y, z) of target points.

Figure 28A:
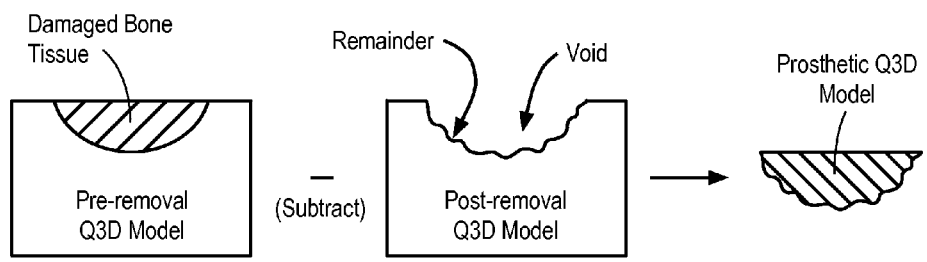
FIGS. 28A-28B are illustrative drawings representing use of a first pre-removal first Q3D model and a post-removal second Q3D model to produce a third Q3D model of a prosthetic implant in accordance with some embodiments.
Figure 28B:
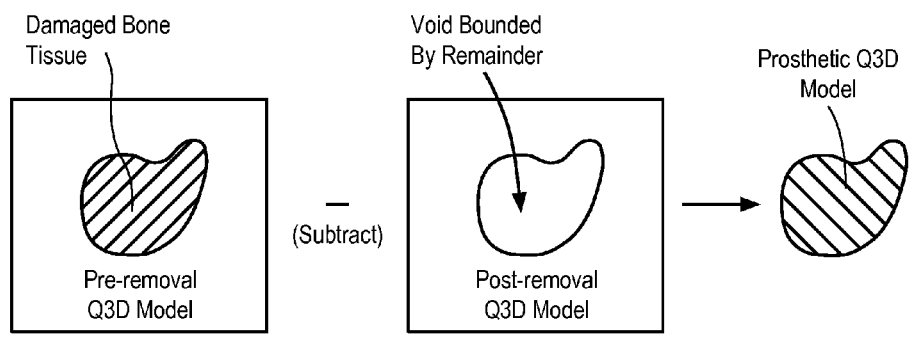

FIGS. 28A-28B are illustrative drawings representing use of a pre-removal first Q3D model and a post-removal second Q3D model to produce a third Q3D model of a prosthetic implant in accordance with some embodiments. FIG. 28A is an illustrative drawing representing cross-sectional views of the pre-removal first Q3D model of the anatomical structure and the post-removal second Q3D model of the anatomical structure and third Q3D model of the prosthetic structure in accordance with some embodiments. FIG. 28B is an illustrative drawing representing top elevation views of the pre-removal first Q3D model of the anatomical structure and the post-removal second Q3D model of the anatomical structure and the third Q3D model of the prosthetic structure in accordance with some embodiments. As shown in FIGS. 28A-28B, the Q3D model of the prosthetic structure is determined by determining one or more differences between the post-removal Q3D model corresponding to the anatomical structure of FIGS. 28A and 28B from the pre-removal first Q3D model of FIGS. 28A and 28B. More particularly, the post-removal second Q3D model includes the remainder, which defines a void or empty region from which the damaged bone tissue has been removed. The third Q3D model represents a replacement structure that is shaped and dimensioned to fit snugly against the remainder structure that defines the void region. In some embodiments, the differences are determined by subtracting the second Q3D model from the first Q3D model. 3D digital subtraction is a technique known to those of skill in the art. For example, it has been previously used in digital angiography, such as presented in U.S. Pat. No. 5,647,360 (filed Jun. 30, 1995), and incorporated herein by reference.

It will be appreciated that Q3D imagining may be used to provide periodic or continuous updates of changes imparted to an anatomical structure as it is being modified during a surgical procedures such as milling a surface of bone, for example, to remove tissue, for example. In this manner, a surgeon can be provided Q3D measurement information indicative of progress of the surgery and can make adjustments accordingly. Furthermore, the Q3D models created in the course of a surgery can be used to create complementary Q3D or 3D models used to produce or select a replacement anatomical object that fits within a tissue void or tissue surface structure produced as a result of the surgery, for example. Therefore, a custom surgical implant can be developed or selected during a surgical procedure, for example.

Figure 29A:
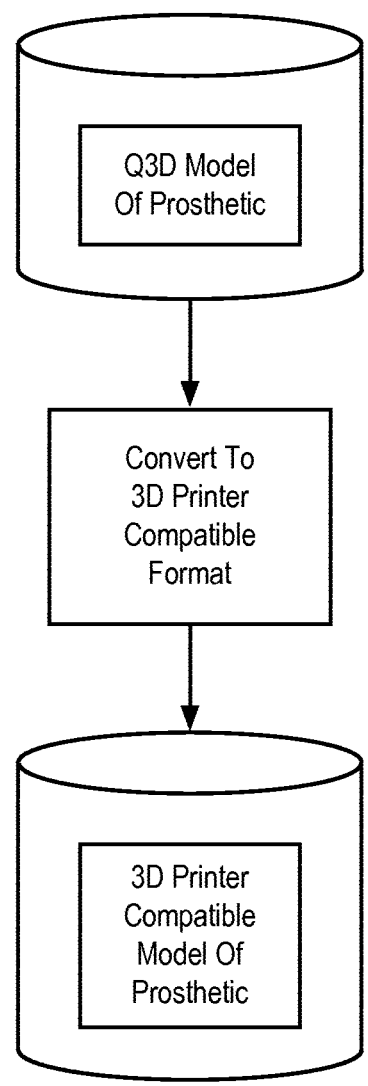
FIG. 29A is an illustrative drawing representing a process to convert a Q3D of a prosthetic structure model to a file structure that is useable by a three-dimensional (3D) printer machine in accordance with some embodiments.

FIG. 29A is an illustrative drawing representing a process to convert a Q3D of a prosthetic structure model to a file structure that is useable by a three-dimensional (3D) printer machine in accordance with some embodiments. 3D printing, also referred to as additive manufacturing, is a well-known process of making three dimensional solid objects from a digital file. The creation of a 3D printed object is achieved using additive processes. In an additive process an object is created by laying down successive layers of material until the entire object is created. A 3D printer typically is configured according to a Computer Aided Design (CAD) model contained in a file and a 3D modeling program to manufacture a structure represented in the model. The 3D modeling program is used to configure the 3D printer for printing, slices the CAD model into hundreds or thousands of horizontal layers. A production file prepared from the CAD model file is uploaded to a 3D printer to configure it to create (e.g., print) the object layer by layer. The 3D printer reads every slice (or 2D image) and proceeds to create the object blending each layer together with no sign of the layering visible, resulting in one three-dimensional object. A computer system (not shown) is configured to implement a file conversion process to convert the Q3D model of the prosthetic structure to a 3D printer compatible file structure. The Q3D model of the prosthetic structure stored in a computer readable storage device acts as an input to a conversion process. A 3D printer readable file that is useable by a 3D printer is an output of the conversion process. For the particular application discussed herein, replacement or repair of bone, the file conversion process produces a file suitable to instruct a 3D printer to produce a structure that has a complementary structure that fits snugly against the remainder bone tissue and fills, or substantially fills, the void such as the example void of FIG. 26 produced by the surgical removal of damaged or injured tissue. Examples of suitable 3D printer formats include standard formats such as .stl, .obj, .ztl, .iges, .mb, .max, and .3ds. Alternatively, proprietary or non-standard 3D printing formats may be used.

Figure 29B:
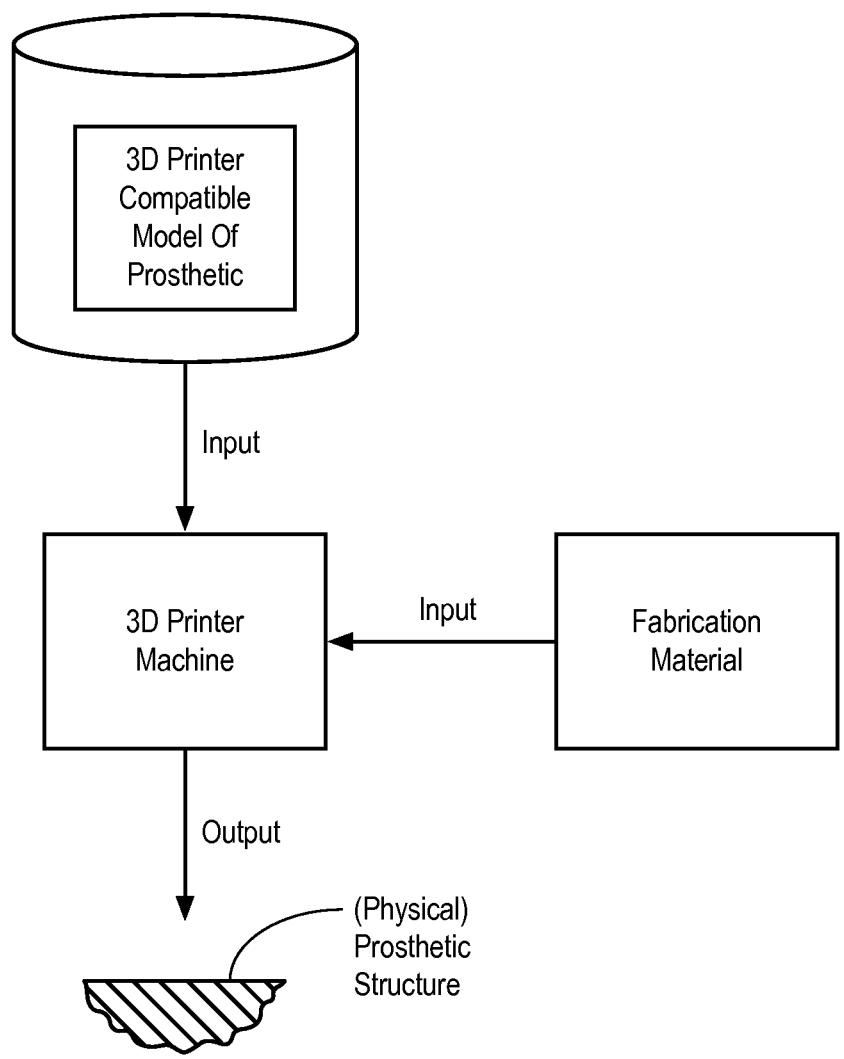
FIG. 29B is an illustrative drawing representing a process using of a 3D printer to produce a prosthetic implant to interfit with the healthy or uninjured region.

FIG. 29B is an illustrative drawing representing a process using of a 3D printer to produce a prosthetic implant to interfit with the healthy or uninjured region. A 3D printer machine receives the 3D printer readable file produced from the Q3D model of the prosthetic structure as the manufacturing input data used to guide the printing process. The 3D printer configured according to the 3D printer readable file converts the fabrication material to a prosthetic implant that is sized to interfit with the remainder healthy or uninjured region. The fabrication material can be biocompatible, suitable for long-term implantation, and it may have material properties required for the specific goal of the clinical procedure. As an example, without limitation, the following is a list of such materials: ceramic, stainless steel, cobalt-chromium alloys, titanium, polyethylene, or zirconium.

Figure 30A:
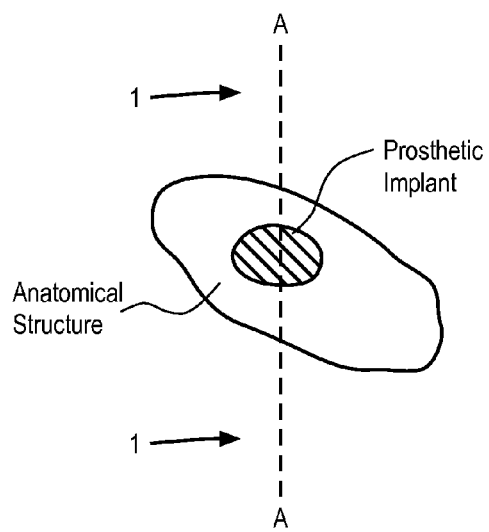
FIG. 30A is an illustrative drawing showing an example view of an anatomical structure after the surgical procedure to snugly interfit the prosthetic implant with the remainder region.
Figure 30B:
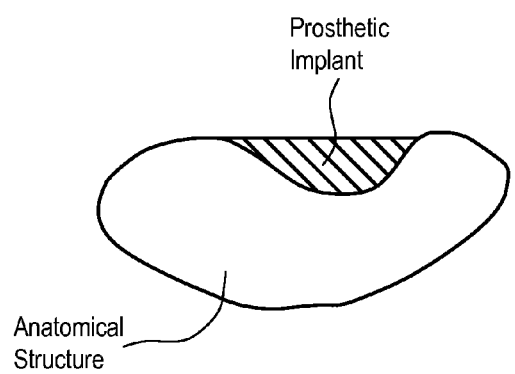
FIG. 30B is a side view cross-section view generally along dashed lines A-A from perspective 1-1 in FIG. 30A showing contours of the example remainder region.

FIG. 30A is an illustrative drawing showing an example top view of an anatomical structure after the surgical procedure to snugly interfit the prosthetic implant with the remainder region. Referring to FIG. 5, a physician may use a surgical instrument 101A or 101B to secure the prosthetic implant to the remainder region. The prosthetic implant may be secured to the remainder healthy or uninjured region using acrylic cement, for example. Alternatively, uncemented fixation may be used. With uncemented fixation, the surface of the implant is composed of a porous, honeycomb-like surface that allows for the in-growth of new bone tissue to help hold the 3D printed implant in place. Thus, it will be appreciated that the Q3D information gleaned using the imaging sensor array is used to produce an implant that fits well with the contours of the remainder region from which the damaged portion has been removed. FIG. 30B is a side cross-section view generally along dashed cutting plane line A-A from perspective 1-1 in FIG. 30A showing contours of the example remainder region.

Alternatively, the Q3D information can be used to select from among pre-made prosthetic implants. The Q3D information can provide dimensions that can be compared with dimensions of multiple pre-made implants (not shown), and an implant with the closest match to the required dimensions is selected. For example, in reference to FIG. 31A and FIG. 32A, if the procedure involves total knee replacement then the Q3D information can be used to select, for example, the appropriate size for the tibial plate 3206 or for the femoral component 3208. For simpler partial knee replacement procedures, such as FIG. 31B, the Q3D information could be used to select from a list of partial femoral components 3210 or partial tibial plates 3212 of FIG. 32B.

Q3D Models for Performance Evaluation

Steerable catheter visualization and tissue manipulation systems are described in U.S. Pat. No. 8,657,805 B2 (filed May 8, 2008); U.S. Patent Application Pub. No. US 2013/0172726 A9 (filed May 12, 2010); and U.S. Patent Application Pub. No. US 2009/0203962 A1 (filed Feb. 6, 2009) (the '962 Publication). The '962 Publication, which is expressly incorporated herein in its entirety by this reference, discloses stent delivery under direct visualization using an imaging hood.

A tissue-imaging and manipulation apparatus described in the '962 Publication is able to provide real-time images in vivo of tissue regions within a body lumen such as a heart chamber, which is filled with blood flowing dynamically through it. The described apparatus is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, and arrhythmogenic focus ablation, among other procedures.

Figure 33A:
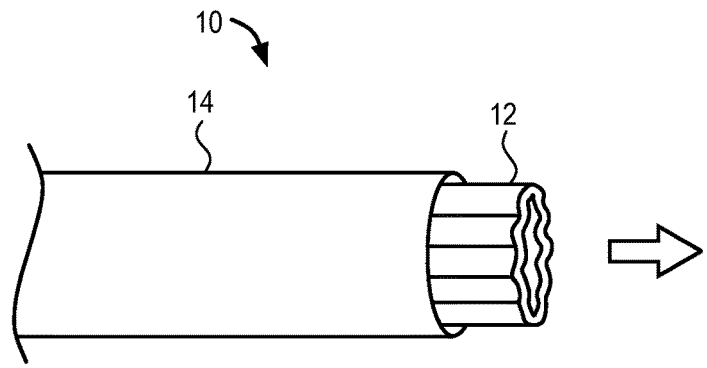
FIG. 33A is an illustrative drawing showing a side view of one variation of a prior art tissue imaging apparatus during deployment from a sheath or delivery catheter.
Figure 33B:
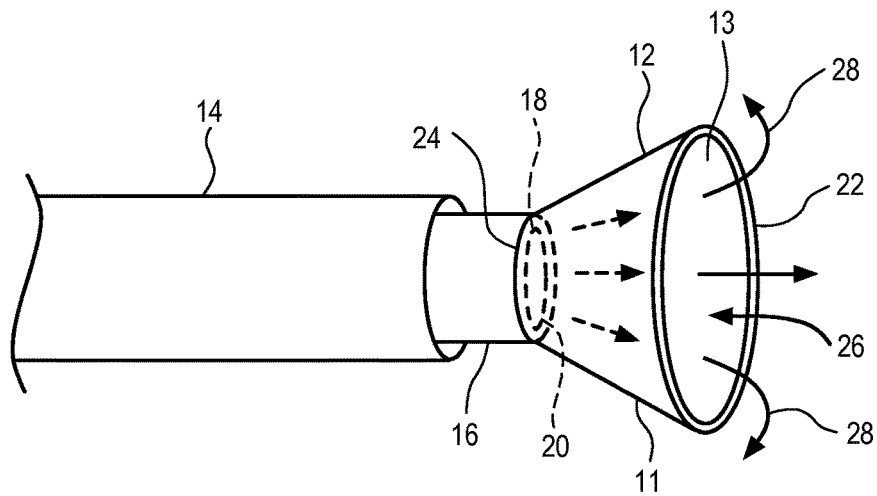
FIG. 33B is an illustrative drawing showing the prior art deployed tissue imaging apparatus of FIG. 33A having an optionally expandable hood or sheath attached to an imaging and/or diagnostic catheter.
Figure 33C:
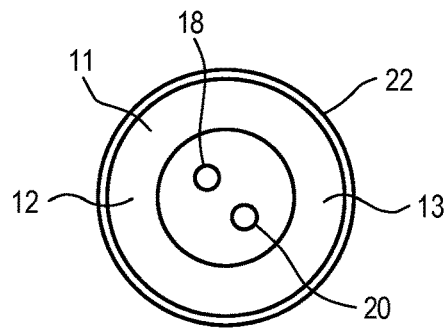
FIG. 33C is an illustrative drawing showing an end view of a prior art deployed imaging apparatus.

One variation of a tissue access and imaging apparatus is shown in the '962 Publication in the detail perspective views of FIGS. 33A to 33C. As shown in FIG. 33A, tissue imaging and manipulation assembly 10 may be delivered intravascularly through the patient's body in a low-profile configuration via a delivery catheter or sheath 14. In the case of treating tissue, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 33B. Imaging hood 12 may be fabricated from a variety of pliable or conformable biocompatible material including but not limited to, e.g., polymeric, plastic, or woven materials. One example of a woven material is Kevlar®, which is an aramid and which can be made into thin (e.g., less than 0.001 in.) materials which maintain enough integrity for applications described in this description. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen, such as a heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical (as shown), semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 33C shows an end view of the imaging hood 12 in its deployed configuration. Also shown are the contact lip or edge 22 and fluid delivery lumen 18 and imaging lumen 20.

Figure 34A:
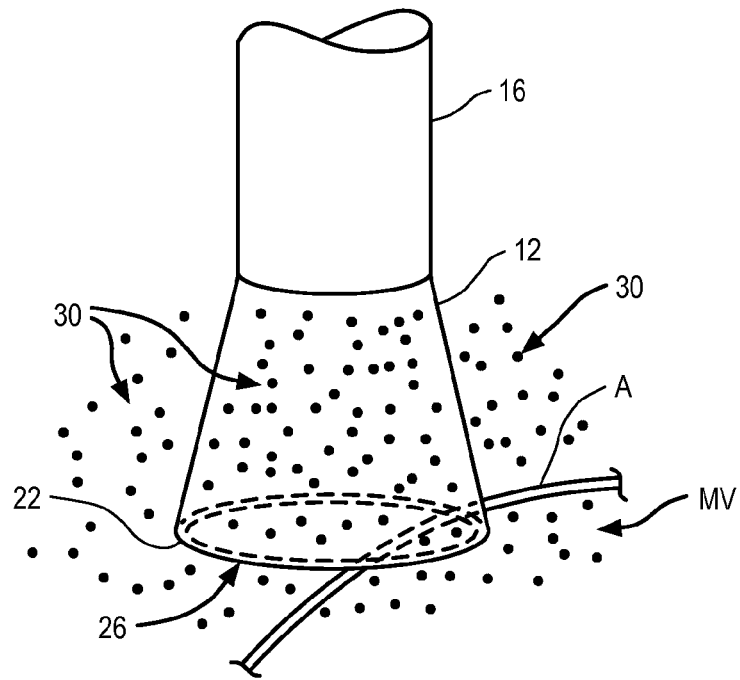
FIGS. 34A-34B are illustrative drawings showing one example of a prior art deployed tissue imager positioned against or adjacent to the tissue to be imaged and a flow of fluid, such as saline, displacing blood from within the expandable hood.
Figure 34B:
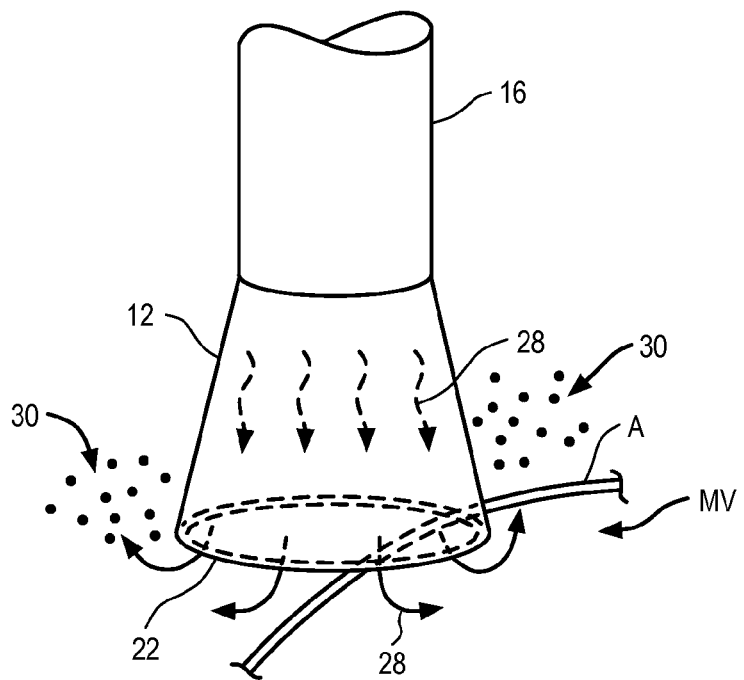

As seen in the example of FIGS. 34A and 34B of the '962 Publication, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 34A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 34B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 35A:
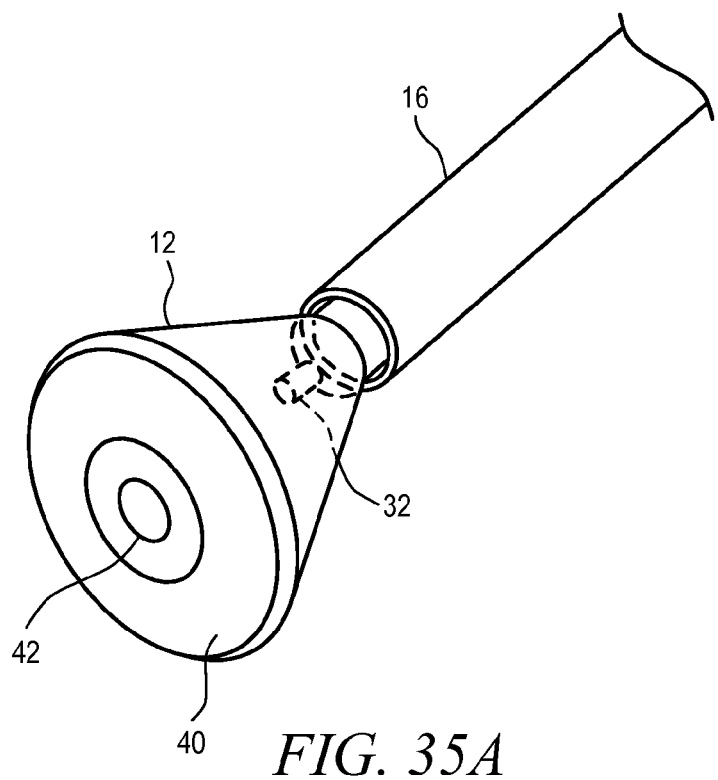
FIGS. 35A-35B are illustrative drawing showing perspective and end views, respectively, of a prior art imaging hood having at least one layer of a transparent elastomeric membrane over the distal opening of the hood.
Figure 35B:
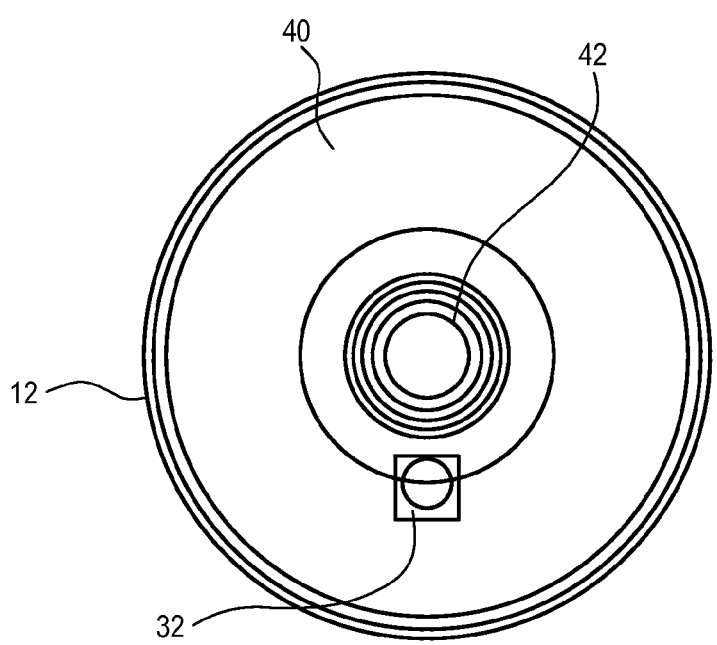

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations. An additional variation of the imaging hood 12 is shown in the perspective and end views, respectively, of FIGS. 35A and 35B of the '962 Publication, where imaging hood 12 includes at least one layer of a transparent elastomeric membrane 40 over the distal opening of hood 12. The '962 Publication discloses one or more optical fiber bundles 32 may be positioned within the catheter and within imaging hood 12 to provide direct in-line imaging of the open area within hood 12. An aperture 42 having a diameter which is less than a diameter of the outer lip of imaging hood 12 may be defined over the center of membrane 40 where a longitudinal axis of the hood intersects the membrane such that the interior of hood 12 remains open and in fluid communication with the environment external to hood 12. Furthermore, aperture 42 may be sized, e.g., between 1 to 2 mm or more in diameter and membrane 40 can be made from any number of transparent elastomers such as silicone, polyurethane, latex, etc. such that contacted tissue may also be visualized through membrane 40 as well as through aperture 42.

Aperture 42 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 42 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 42 may be aligned with catheter 16 such that any instruments (e.g., piercing instruments, guide wires, tissue engagers, etc.) that are advanced into the hood interior may directly access the underlying tissue uninhibited or unrestricted for treatment through aperture 42. In other variations in which aperture 42 is not be aligned with catheter 16, instruments passed through catheter 16 may still access the underlying tissue by simply piercing through membrane 40.

Figure 36:
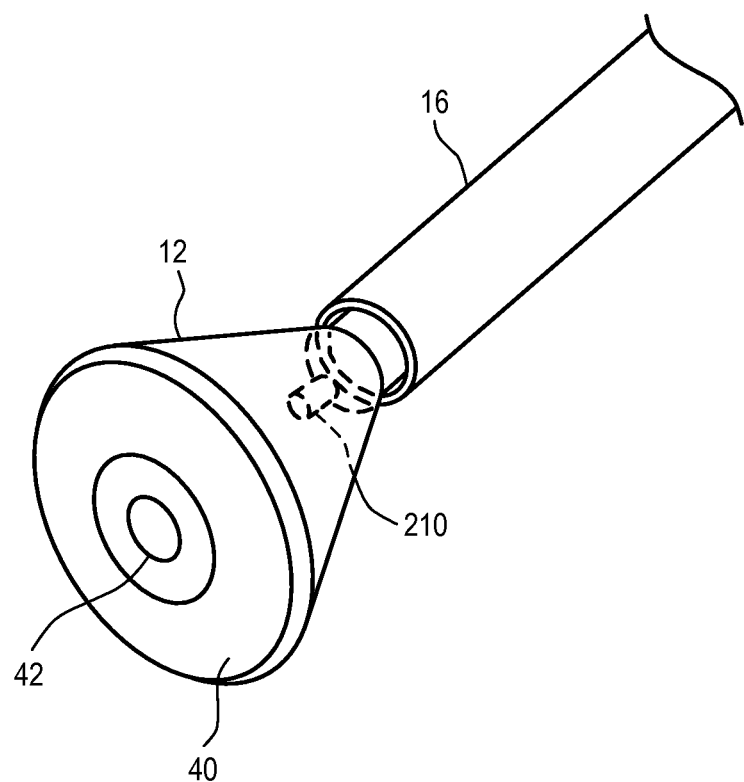
FIG. 36 is an illustrative drawing showing a perspective view of a Q3D endoscope with an imaging hood having at least one layer of a transparent elastomeric membrane over the distal opening of the hood in accordance with some embodiments.

FIG. 36 is an illustrative drawing showing an image sensor array 210, described above with reference to FIGS. 7A-7B and 8, positioned within the instrument and within imaging hood 12 to provide direct in-line Q3D imaging of the open area within hood 12. Alternatively, an image sensor array can be disposed outside the hood, and one or more optical fiber bundles, such as bundles 32 shown in FIG. 35A, can deliver image information to an image sensor array disposed outside the imaging hood 12.

Figure 37:
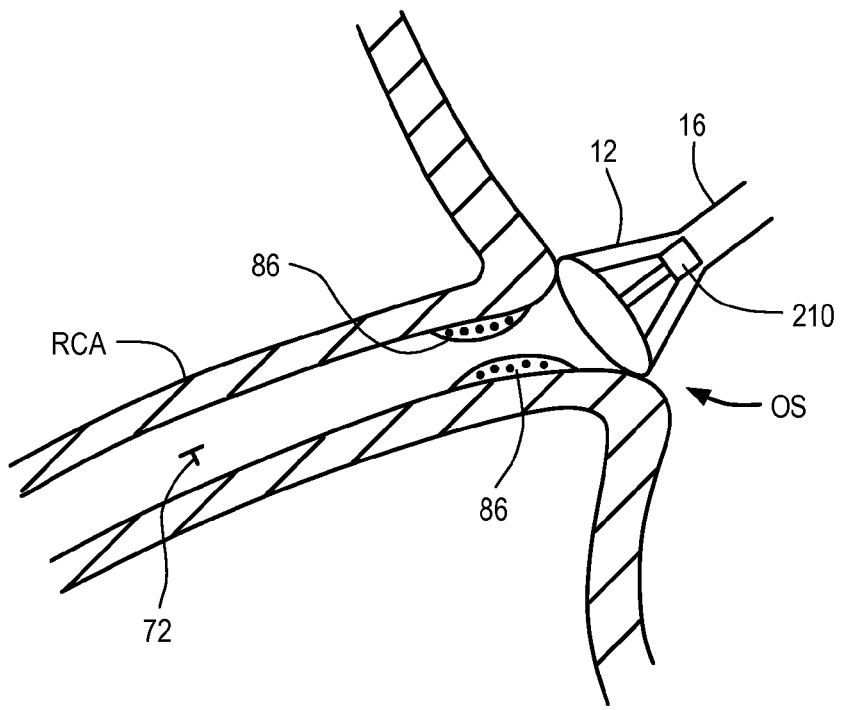
FIG. 37 is an illustrative drawing showing an example use of the hood including an image sensor array in contact against the ostium (OS), which communicates with the right coronary artery (RCA), in accordance with some embodiments.

FIG. 37 is an illustrative drawing showing an example use of the hood 12 including an image sensor array 210 in contact against the ostium (OS), which communicates with the right coronary artery (RCA), in accordance with some embodiments. Once hood 12 is in contact against the ostium OS, the clearing fluid may be introduced within the open area of hood 12 to purge the blood from the hood interior to provide a clear field through which the image sensor array 210 can capture Q3D information. As to contour of tissue surrounding the ostium OS and at least a portion of the vessel wall extending into lumen 72. For example, an ostial lesion 86, which is to be treated, is shown in FIG. 37. The image sensor array 210 may be used to directly capture Q3D image information at least partially into lumen 72 as the purged clearing fluid exits hood 12 and down through lumen 72 to provide an image of the lesion 86 to be treated. Q3D information as to the dimensions of the lesion 86 can be used to size the treatment device intended to be used. Alternatively, the Q3D information can be used to understand the extent of the clinical problem, so that the therapy is tailored more specifically to patient's situation.

Figure 38:
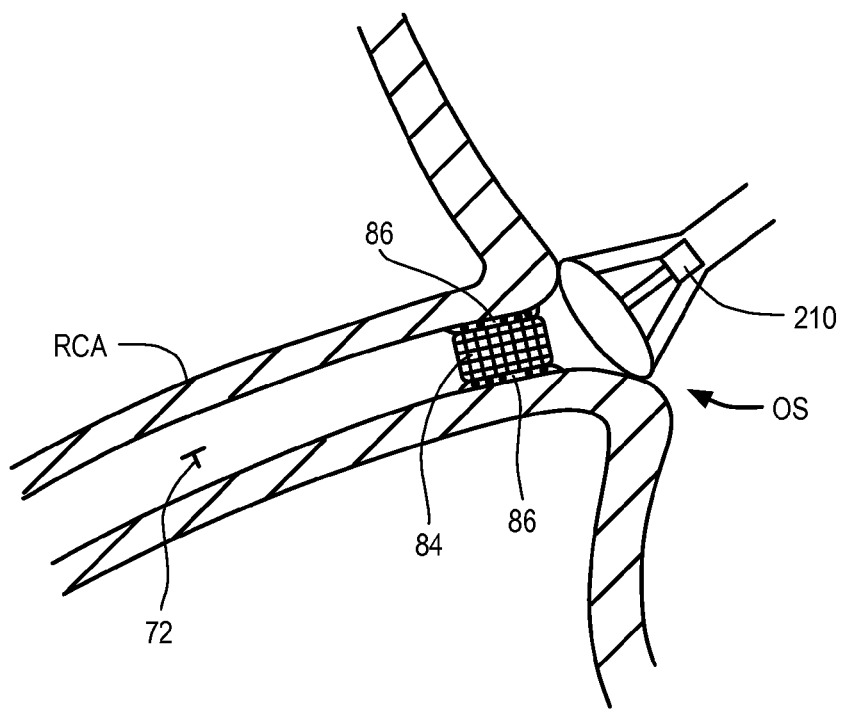
FIG. 38 is an illustrative drawing showing an example use of the hood including image sensor array in contact with the ostium (OS) and in which a stent has been installed in the right ascending artery (RCA), in accordance with some embodiments.

FIG. 38 is an illustrative drawing showing an example use of the hood including image sensor array 210 in contact with the ostium (OS) and in which a stent 84 has been installed in the right ascending artery (RCA), in accordance with some embodiments. The stent 84 is installed over lesion 86. Image sensor array 210 may be used to provide Q3D information to evaluate the deployment and positioning of stent 84 within lumen 72. As an example, without limitations, the Q3D information may be used to size stent 84 according to the size of patient's RCA OS. The Q3D information about the lesion 86 can also be used to size the length of stent 84 appropriately. In yet another embodiment, the Q3D information can be used to check the performance of stent 84 once deployed in place. For example, the Q3D information can show precisely, using quantitative information, the fit of the stent to the inner wall of the RCA. If there is incomplete coverage of the lesion, or if the stent diameter is too large or too small, these conditions can all be quantified based on the Q3D information. FIG. 41 is an illustrative drawing showing an example of quantitative evaluation criteria that can be used to assess the performance of stent coverage of blood vessel. One of the quantitative goals is to minimize the difference between mean stent cross-sectional area and the mean lumen cross-sectional area.

Figure 39:
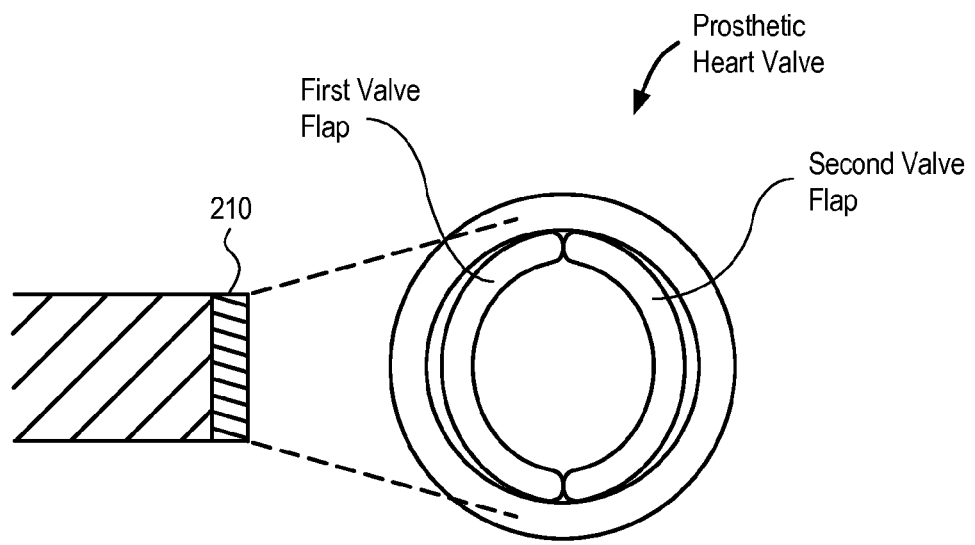
FIG. 39 is an illustrative drawing showing a Q3D endoscope disposed adjacent to a prosthetic heart valve implant, which is in an open position.
Figure 40:
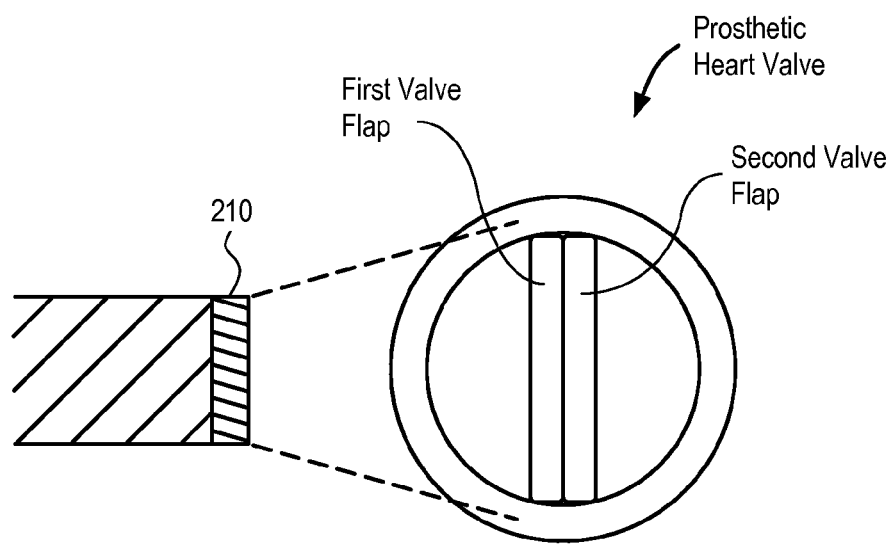
FIG. 40 is an illustrative drawing showing the Q3D endoscope disposed adjacent to the prosthetic heart valve implant, which is in a closed position.

FIG. 39 is an illustrative drawing showing a Q3D endoscope disposed adjacent to a prosthetic heart valve implant, which is in an open position. FIG. 40 is an illustrative drawing showing the Q3D endoscope disposed adjacent to the prosthetic heart valve implant, which is in a closed position. The Q3D endoscope captures a Q3D image using an image sensor array 210. The Q3D endoscope may be disposed within an imaging hood. However, the hood is not shown in order to simplify the description. Referring to FIG. 39, the first and second valve flaps are shown spaced apart indicating that that valve is open and fluid (e.g., blood) can flow through. Referring to FIG. 40, the first and second valve flaps are shown close together indicating that that valve is closed and fluid (e.g., blood) cannot flow through. In accordance with some embodiments, the Q3D endoscope captures a series of Q3D images that collectively provide dimensional information associated with the opening and closing motion of the valve. For example, without limitation, the information provided by the Q3D model associated with FIG. 40 can show whether or not the prosthetic valve closely completely. Incomplete closure of the valve may result in significant regurgitation, which, in turn, reduces the performance of the patient's heart. Similarly, Q3D information associated with FIG. 39 can show whether the prosthetic valve was sized correctly with respect to anatomic details of the patient's heart. If the prosthetic valve in FIG. 39 were an aortic valve, for example and without limitations, then it would be important to quantify the fit to the aortic ostium and to the aortic wall. Similarly important, it would be important to confirm that the valve opens completely, as shown in FIG. 39. If the valve were not opening completely, the patient's cardiac output would be impaired. Also, in time, the patient's blood pressure would be affected, as pressure would start building up upstream from the aortic valve. Similar important information could be provided for mitral, tricuspid or pulmonic valvular procedures.

It should be understood that the use of Q3D information in medical applications are not limited to applications of stents and blood vessels, or to heart valves. The basic principles illustrated above can be modified to include use with various prosthetic devices, such as for size or shape selection, optimal positioning of the device, etc.

The foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

The invention claimed is:

1. A system to produce a replacement anatomical structure, comprising:
 a quantitative three-dimensional (Q3D) endoscope including an imaging sensor array comprising a plurality of imaging sensors, wherein each imaging sensor includes a corresponding lens stack and a two-dimensional arrangement of pixels arranged in a focal plane of the lens stack, wherein at least three of the imaging sensors of the imaging sensor array are disposed to have coplanar fields of view that overlap, and wherein the corresponding lens stack of each imaging sensor creates a separate optical channel that resolves an image of an anatomical structure within a field of view that includes target tissue in a focal plane of the corresponding lens stack;
 at least one processor configured to:
 produce a first Q3D model based upon image information captured from the anatomical structure that represents an external surface of bone tissue including the target bone tissue;
 produce a second Q3D model based upon image information captured from the anatomical structure that represents remainder tissue structure, which defines an empty region in a location of the anatomical structure from which the target tissue has been tissue removed; and
 produce a third Q3D model of a replacement structure that is shaped and dimensioned to fit against the remainder structure that defines the empty region and to substantially fill the empty region based at least in part upon the first Q3D model and the second Q3D model.

2. The system of claim 1,
 wherein producing the third Q3D model includes determining one or more differences between the first Q3D model and the second Q3D model.

3. The system of claim 1,
 wherein producing the third Q3D model includes determining 3D digital subtraction between the first Q3D model and the second Q3D model.

4. The system of claim 1,
 wherein the at least one processor is configured to:
 convert the third Q3D model to a three dimensional (3D) model of the replacement structure in a format that is suitable for use by a 3D printing machine.

5. The system of claim 1,
 wherein the at least one processor is configured to:
 provide an output signal indicative of the size required for said replacement structure.

6. A method of producing a surgical replacement structure comprising:
 using a Q3D endoscope to capture image information from an external surface of bone tissue that includes target bone tissue;
 producing a first quantitative three dimensional (Q3D) model based upon the image information captured from the external surface of the bone tissue that includes the target bone tissue;
 using the Q3D endoscope to capture image information from remainder tissue bone structure, which defines an empty region in a location of the bone tissue from which the target bone tissue has been tissue removed;
 producing a second Q3D model based upon image information captured from the anatomical structure that represents the remainder tissue bone structure, which defines the empty region in the location of the bone tissue from which the target bone tissue has been tissue removed; and
 producing a third Q3D model of a replacement structure shaped and dimensioned to fit against the remainder structure that defines the empty region and to substantially fill the empty region, produced based upon the first Q3D model and the second Q3D model.

7. The method of claim 6 further including:
 wherein producing the third Q3D model includes determining a 3D digital subtraction between the first Q3D model and the second Q3D model.

8. The method of claim 6 further including:
 converting the third Q3D model to a three dimensional (3D) model of the replacement structure in a format that is suitable for use by a 3D printing machine.

9. The method of claim 8 further including using a 3D printing machine configured using the 3D model to produce the replacement structure.

10. The method of claim 6 further including:
 sizing an off-the-shelf replacement structure for use as an implant for replacing said removed tissue based at least in part upon the third Q3D model of the replacement structure.

11. The method of claim 6,
 wherein producing the third Q3D model includes determining one or more differences between the first Q3D model and the second Q3D model.

12. A system for 3D imaging of surgical scenes comprising:
 a Q3D endoscope;
 a manipulator to move the Q3D endoscope by known amounts to successive redundant positions to provide separate viewpoints of a target tissue region;
 means to capture redundant multiple successive Q3D images from said successive positions; and
 a processor configured to produce a Q3D model of the surgical scene based upon the redundant multiple successive Q3D images.

13. A method comprising:
 illuminating an anatomical structure with a light source;
 successively moving a Q3D endoscope by known amounts to each of multiple successive redundant positions to provide separate viewpoints of a target tissue region within a body cavity;
 capturing redundant multiple successive image projections from the target tissue using the Q3D endoscope at the multiple successive redundant positions; and
 producing a Q3D model based upon the redundant multiple successive captured image projections.

14. The method of claim 13, wherein successively moving the endoscope includes successively changing physical position of the endoscope.

15. The method of claim 13, wherein successively moving the endoscope includes successively adjusting optical property of one or more lenses associated with the Q3D endoscope.

16. A system for quantitative evaluation of an implantable device comprising:
 a quantitative three-dimensional (Q3D) endoscope including an imaging sensor array comprising a plurality of imaging sensors, wherein each imaging sensor includes a corresponding lens stack and a two-dimensional arrangement of pixels arranged in a focal plane of the lens stack, wherein at least three of the imaging sensors of the imaging sensor array are disposed to have coplanar fields of view that overlap, and wherein the corresponding lens stack of each imaging sensor creates a separate optical channel that resolves an image a structure within a field of view that is targeted to receive an implantable device in a focal plane of the corresponding lens stack;
 at least one processor configured to:
 produce a first Q3D model of said anatomical structure before implantation; and
 produce an output signal indicative of the size required for implanted device;
 produce a second Q3D model of the anatomical structure after implantation; and
 produce at least one quantitative evaluation output based upon, at least in part, on the second Q3D model.

17. A system for quantitative evaluation of an implantable device comprising:
 a quantitative three-dimensional (Q3D) endoscope including an imaging sensor array comprising a plurality of imaging sensors, wherein each imaging sensor includes a corresponding lens stack and a two-dimensional arrangement of pixels arranged in a focal plane of the lens stack, wherein at least three of the imaging sensors of the imaging sensor array are disposed to have coplanar fields of view that overlap; and wherein the corresponding lens stack of each imaging sensor creates a separate optical channel that resolves an image, of an opening and closing of an anatomical valve within a field of view that is targeted to receive an implantable prosthetic valve device in a focal plane of the corresponding lens stack;
 at least one processor configured to:
 produce one or more a first Q3D models of opening and closing of said anatomical valve before implantation of the prosthetic valve device; and
 produce an output signal indicative of
 opening or closing size required of the prosthetic valve device.

18. A system for quantitative evaluation of an implantable device comprising:
 a quantitative three-dimensional (Q3D) endoscope including an imaging sensor array comprising a plurality of imaging sensors, wherein each imaging sensor includes a corresponding lens stack and a two-dimensional arrangement of pixels arranged in a focal plane of the lens stack, wherein at least three of the imaging sensors of the imaging sensor array are disposed to have coplanar fields of view that overlap, and wherein the corresponding lens stack of each imaging sensor creates a separate optical channel that resolves an image, of an anatomical lumen within a field of view that is targeted to receive an implantable stent device in a focal plane of the corresponding lens stack;
 at least one processor configured to:
 produce one or more a first Q3D models indicating mean cross section area of said anatomical lumen before implantation of the stent device; and
 produce an output signal indicative of mean stent cross-sectional required of the stent device to fit within the anatomical lumen.

19. A system for quantitative evaluation of an implantable device comprising:
 a quantitative three-dimensional (Q3D) endoscope including an imaging sensor array comprising a plurality of imaging sensors, wherein each imaging sensor includes a corresponding lens stack and a two-dimensional arrangement of pixels arranged in a focal plane of the lens stack, wherein at least three of the imaging sensors of the imaging sensor array are disposed to have coplanar fields of view that overlap, and wherein the corresponding lens stack of each imaging sensor creates a separate optical channel that resolves an image, of a stent device within an anatomical lumen within a field of view in a focal plane of the corresponding lens stack;
 at least one processor configured to:
 produce one or more a first Q3D models indicating the stent device within an inner wall of the anatomical lumen anatomical lumen; and
 produce an output signal indicative of fit of the stent to an inner wall of the anatomical lumen.

* * * * *

UNITED STATES PATENT AND TRADEMARK OFFICE
CERTIFICATE OF CORRECTION

PATENT NO. : 10,350,009 B2
APPLICATION NO. : 15/300262
DATED : July 16, 2019
INVENTOR(S) : Panescu et al.

Page 1 of 1

It is certified that error appears in the above-identified patent and that said Letters Patent is hereby corrected as shown below:

In the Claims

In Column 32, Line 65, in Claim 14, after "claim 13,", insert --¶--

In Column 33, Line 1, in Claim 15, after "claim 13,", insert --¶--

In Column 33, Line 38, in Claim 17, delete "overlap;" and insert --overlap,-- therefor In Column 34, Line 1, in Claim 17, after "of", delete "¶"

Signed and Sealed this
Third Day of November, 2020

Andrei Iancu
*Director of the United States Patent and Trademark Office*